(12) United States Patent
Leon et al.

(10) Patent No.: US 12,006,366 B2
(45) Date of Patent: Jun. 11, 2024

(54) METHODS AND COMPOSITIONS FOR PREVENTING TYPE 1 DIABETES

(71) Applicant: Provention Bio, Inc., Red Bank, NJ (US)

(72) Inventors: Francisco Leon, Bethesda, MD (US); Kevan C. Herold, Norwalk, CT (US); Sarah Alice Long, Seattle, WA (US); Peter S. Linsley, Seattle, WA (US)

(73) Assignees: Provention Bio, Inc.; Yale University; Benaroya Research Institure at Virginia Mason

( * ) Notice: Subject to any disclaimer, the term of this patent is extended or adjusted under 35 U.S.C. 154(b) by 0 days.

(21) Appl. No.: 17/345,495

(22) Filed: Jun. 11, 2021

(65) Prior Publication Data

US 2022/0041720 A1    Feb. 10, 2022

Related U.S. Application Data

(60) Provisional application No. 63/192,242, filed on May 24, 2021, provisional application No. 63/037,968, filed on Jun. 11, 2020.

(30) Foreign Application Priority Data

Jan. 26, 2021    (TW) ................................ 110102871

(51) Int. Cl.
  C07K 16/28    (2006.01)
  A61P 3/10    (2006.01)
  G01N 33/68    (2006.01)
  A61K 39/00    (2006.01)

(52) U.S. Cl.
  CPC ............ C07K 16/2809 (2013.01); A61P 3/10 (2018.01); G01N 33/6854 (2013.01); *A61K 2039/505* (2013.01); *A61K 2039/545* (2013.01); *G01N 2800/52* (2013.01)

(58) Field of Classification Search
  CPC . C07K 16/2809; A61P 3/10; A61K 2039/505; A61K 2039/545
  See application file for complete search history.

(56) References Cited

U.S. PATENT DOCUMENTS

| | | | |
|---|---|---|---|
| 5,885,573 A | 3/1999 | Bluestone et al. |
| 6,491,916 B1 | 12/2002 | Bluestone et al. |
| 6,723,538 B2 | 4/2004 | Mack et al. |
| 6,905,685 B2 | 6/2005 | Kwon |
| 6,956,041 B2 | 10/2005 | Blumenkopf et al. |
| 7,041,289 B1 | 5/2006 | Bach et al. |
| 7,091,208 B2 | 8/2006 | Blumenkopf et al. |
| 7,235,641 B2 | 6/2007 | Kufer et al. |
| 7,262,276 B2 | 8/2007 | Huang et al. |
| 7,304,033 B2 | 12/2007 | Larsen et al. |
| 7,395,158 B2 | 7/2008 | Monfre et al. |
| 7,482,327 B2 | 1/2009 | Hagerty et al. |
| 7,563,869 B2 | 7/2009 | Honjo et al. |
| 7,569,569 B2 | 8/2009 | Blumenkopf et al. |
| 7,592,313 B2 | 9/2009 | Zheng et al. |
| 7,612,181 B2 | 11/2009 | Chengbin et al. |
| 7,635,472 B2 | 12/2009 | Kuler et al. |
| 7,714,103 B2 | 5/2010 | Levetan et al. |
| 7,728,114 B2 | 6/2010 | Mach et al. |
| 7,744,863 B1 | 6/2010 | Hall et al. |
| 7,820,166 B2 | 10/2010 | Lanzavecchia |
| 7,883,703 B2 | 2/2011 | Weiner et al. |
| 7,919,089 B2 | 4/2011 | Kufer et al. |
| 7,989,415 B2 | 8/2011 | Levetan et al. |
| 7,998,479 B2 | 8/2011 | Honjo et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,182,812 B2 | 5/2012 | Schuurman et al. |
| 8,211,430 B2 | 7/2012 | Levetan et al. |
| 8,211,440 B2 | 7/2012 | Chang et al. |
| 8,246,955 B2 | 8/2012 | Honjo et al. |
| 8,246,960 B2 | 8/2012 | Chang et al. |
| 8,258,268 B2 | 9/2012 | Wu et al. |
| 8,383,578 B2 | 2/2013 | Levetan et al. |
| 8,394,926 B2 | 3/2013 | Lutterbuse et al. |
| 8,398,995 B2 | 3/2013 | Rottiers et al. |
| 8,420,081 B2 | 4/2013 | Fraunhofer et al. |

(Continued)

FOREIGN PATENT DOCUMENTS

| | | |
|---|---|---|
| EP | 1515749 B1 | 3/2005 |
| EP | 1591527 B1 | 11/2005 |

(Continued)

OTHER PUBLICATIONS

Chamow and Ashkenazi, TIBTECH 14: 52-60, (1996).*
Rudikoff et al., Proc. Natl. Acad. Sci. 79: 1979-1983, (1982).*
Anonymous: "Anti-CD3 Prevention ANTI-CD3 MAB (Teplizumab) for Prevention of Diabetes in Relatives at-risk for type 1 Diabetes Mellitus (Protocol Tn-10)", Type 1 Diabetes TrialNet, Protocol Version Jun. 25, 2014, https://clinicaltrials.gov/ProvidedDocs/61/NCT01030861/Prot_000.
Mannering et al., "The Case for an Autoimmune Aetiology of Type 1 Diabetes", Clinical and Experimental Immunology, Wiley-Blackwell Publishing Ltd., GB, vol. 183, No. 1, pp. 8-15, Oct. 21, 2015.
Noble et al., "Genetics of the HLA Region in the Prediction of Type 1 Diabetes", Current Diabetes Reports, Current Science, Inc., vol. 11, No. 6, pp. 533-542, Sep. 13, 2011.

(Continued)

*Primary Examiner* — Gyan Chandra
(74) *Attorney, Agent, or Firm* — Steptoe LLP; Z. Ying Li; Debashree Chatterjee

(57) ABSTRACT

Provided herein, in one aspect, is a method of preventing or delaying the onset of clinical type 1 diabetes (T1D), comprising: providing a non-diabetic subject who is at risk for T1D; administering a prophylactically effective amount of an anti-CD3 antibody to the non-diabetic subject; and determining, prior to or after the administering step, that the non-diabetic subject has more than about 5% to more than about 10% TIGIT+KLRG1+CD8+ T-cells in all CD3+ T cells, which is indicative of successful prevention or delay of the onset of clinical T1D.

23 Claims, 40 Drawing Sheets

Specification includes a Sequence Listing.

(56) References Cited

U.S. PATENT DOCUMENTS

| | | |
|---|---|---|
| 8,481,022 B2 | 7/2013 | Lodie et al. |
| 8,530,629 B2 | 9/2013 | Chang |
| 8,551,478 B2 | 10/2013 | Mach et al. |
| 8,586,714 B2 | 11/2013 | Ghayur et al. |
| 8,623,830 B2 | 1/2014 | Flier et al. |
| 8,663,634 B2 | 3/2014 | Koenig et al. |
| 8,735,553 B1 | 5/2014 | Li et al. |
| 8,785,400 B2 | 7/2014 | Levetan et al. |
| 8,790,645 B2 | 7/2014 | Kufer et al. |
| 8,808,689 B1 | 8/2014 | Levetan |
| 8,816,047 B2 | 8/2014 | Levetan et al. |
| 8,846,873 B2 | 9/2014 | Xiao et al. |
| 8,883,146 B2 | 11/2014 | Fraunhofer et al. |
| 8,932,586 B2 | 1/2015 | Jones et al. |
| 8,951,518 B2 | 2/2015 | Honjo et al. |
| 8,980,244 B2 | 3/2015 | Mandelboim et al. |
| 8,987,425 B2 | 3/2015 | Lee et al. |
| 9,056,906 B2 | 6/2015 | Koenig et al. |
| 9,079,965 B2 | 7/2015 | Lewyn et al. |
| 9,085,619 B2 | 7/2015 | Fraunhofer et al. |
| 9,089,531 B2 | 7/2015 | Kaufman et al. |
| 9,102,736 B2 | 8/2015 | Hofmeister et al. |
| 9,192,665 B2 | 11/2015 | Zugmaier et al. |
| 9,217,034 B2 | 12/2015 | Li et al. |
| 9,226,962 B2 | 1/2016 | LeGall et al. |
| 9,249,211 B2 | 2/2016 | Schellenberger et al. |
| 9,296,815 B2 | 3/2016 | D'Angelo et al. |
| 9,308,257 B2 | 4/2016 | Sharma et al. |
| 9,315,585 B2 | 4/2016 | Cheung et al. |
| 9,321,812 B2 | 4/2016 | Levetan |
| 9,371,517 B2 | 6/2016 | Jones et al. |
| 9,382,329 B2 | 7/2016 | Chang et al. |
| 9,447,387 B2 | 9/2016 | Jones et al. |
| 9,447,431 B2 | 9/2016 | Thess et al. |
| 9,453,052 B2 | 9/2016 | Gruber et al. |
| 9,474,744 B2 | 10/2016 | Cohen et al. |
| 9,493,563 B2 | 11/2016 | Blein et al. |
| 9,511,110 B2 | 12/2016 | Levetan |
| 9,562,110 B2 | 2/2017 | Zhou et al. |
| 9,574,010 B2 | 2/2017 | Spreter Von Kreudenstein et al. |
| 9,587,021 B2 | 3/2017 | Huang et al. |
| 9,611,325 B2 | 4/2017 | Zhou et al. |
| 9,616,105 B2 | 4/2017 | Paulsen et al. |
| 9,670,286 B2 | 6/2017 | Chang et al. |
| 9,682,143 B2 | 6/2017 | Chang et al. |
| 9,688,772 B2 | 6/2017 | Cheung et al. |
| 9,695,250 B2 | 7/2017 | Lutterbuse et al. |
| 9,701,749 B2 | 7/2017 | Shibayama et al. |
| 9,708,412 B2 | 7/2017 | Baeuerle et al. |
| 9,777,073 B2 | 7/2017 | Shibayama et al. |
| 9,783,609 B2 | 10/2017 | Honjo et al. |
| 9,802,995 B2 | 10/2017 | Ahmed et al. |
| 9,820,955 B2 | 11/2017 | Kaufman et al. |
| 9,850,304 B2 | 12/2017 | Mach et al. |
| 9,879,088 B2 | 1/2018 | Chang et al. |
| 9,982,063 B2 | 5/2018 | Lutterbuse et al. |
| 9,987,356 B2 | 6/2018 | Reimann et al. |
| 10,000,567 B2 | 6/2018 | Ellis et al. |
| 10,000,574 B2 | 6/2018 | Hofmeister et al. |
| 10,010,577 B2 | 7/2018 | Levetan |
| 10,010,578 B2 | 7/2018 | Levetan |
| 10,010,579 B2 | 7/2018 | Levetan |
| 10,010,580 B2 | 7/2018 | Levetan |
| 10,016,482 B2 | 7/2018 | Levetan |
| 10,022,440 B2 | 7/2018 | Wasserfall et al. |
| 10,023,639 B2 | 7/2018 | Li et al. |
| 10,059,767 B2 | 8/2018 | Protzer et al. |
| 10,081,809 B2 | 9/2018 | Monteleone et al. |
| 10,086,046 B2 | 10/2018 | Paulsen et al. |
| 10,093,736 B2 | 10/2018 | Sahin et al. |
| 10,106,623 B2 | 10/2018 | Uhlin et al. |
| 10,111,968 B2 | 10/2018 | Thess et al. |
| 10,118,964 B2 | 11/2018 | Zhou et al. |
| 10,130,638 B2 | 11/2018 | Zugmaier et al. |
| 10,150,812 B2 | 12/2018 | Huang et al. |
| 10,159,710 B2 | 12/2018 | Gruber et al. |
| 10,167,341 B2 | 1/2019 | Cheung et al. |
| 10,191,034 B2 | 1/2019 | Nagorsen |
| 10,239,952 B2 | 3/2019 | Scheinberg et al. |
| 10,251,934 B2 | 4/2019 | Elliman |
| 10,266,608 B2 | 4/2019 | Wu |
| 10,272,050 B2 | 4/2019 | Farokhzad et al. |
| 10,280,425 B2 | 5/2019 | Chen et al. |
| 10,287,365 B2 | 5/2019 | Cheung et al. |
| 10,301,389 B2 | 5/2019 | Ho et al. |
| 10,316,093 B2 | 6/2019 | Cheung et al. |
| 10,329,314 B2 | 6/2019 | Fan et al. |
| 10,329,350 B2 | 6/2019 | Daute et al. |
| 10,369,114 B2 | 8/2019 | Schentag et al. |
| 10,376,518 B2 | 8/2019 | Ellis et al. |
| 10,378,055 B2 | 8/2019 | Ferreri et al. |
| 10,413,605 B2 | 9/2019 | Christen et al. |
| 10,434,078 B2 | 10/2019 | Kaufman et al. |
| 10,443,056 B2 | 10/2019 | Monteleone et al. |
| 10,449,170 B2 | 10/2019 | Venn-Watson |
| 10,465,003 B2 | 11/2019 | Hedrick et al. |
| 10,487,098 B2 | 11/2019 | Fan et al. |
| 10,519,248 B2 | 12/2019 | Cheung et al. |
| 10,548,929 B2 | 2/2020 | Champion et al. |
| 10,556,964 B2 | 2/2020 | Zhou et al. |
| 10,570,103 B2 | 2/2020 | Beaton et al. |
| 10,584,180 B2 | 3/2020 | Gruber |
| 10,590,182 B2 | 3/2020 | Lim et al. |
| 10,633,440 B2 | 4/2020 | Bonvini et al. |
| 10,640,576 B2 | 5/2020 | Jang et al. |
| 10,647,768 B2 | 5/2020 | Johnson et al. |
| 10,647,770 B2 | 5/2020 | Shibayama et al. |
| 10,662,243 B2 | 5/2020 | Nagorsen et al. |
| 10,662,252 B2 | 5/2020 | Chang et al. |
| 10,688,186 B2 | 6/2020 | Shalibhai |
| 10,696,744 B2 | 6/2020 | Zugmaier et al. |
| 10,717,780 B2 | 7/2020 | Sahin et al. |
| 10,730,880 B2 | 8/2020 | Allen et al. |
| 10,730,943 B2 | 8/2020 | Protzer et al. |
| 10,745,478 B2 | 8/2020 | Sirianni et al. |
| 10,752,686 B2 | 8/2020 | Ma et al. |
| 10,772,917 B2 | 9/2020 | Kieffer et al. |
| 10,772,958 B2 | 9/2020 | Yu et al. |
| 10,806,787 B2 | 10/2020 | Kudo et al. |
| 10,849,945 B2 | 12/2020 | Champion et al. |
| 10,858,663 B2 | 12/2020 | Rottiers et al. |
| 10,865,230 B2 | 12/2020 | Liu et al. |
| 10,882,909 B2 | 1/2021 | Ho et al. |
| 10,905,727 B2 | 2/2021 | Rottiers et al. |
| 10,925,972 B2 | 2/2021 | Demetriou et al. |
| 10,940,151 B2 | 3/2021 | Friedman et al. |
| 10,961,315 B2 | 3/2021 | Liu |
| 10,973,889 B2 | 4/2021 | Kjellman et al. |
| 10,975,112 B2 | 4/2021 | Zhao |
| 10,980,890 B2 | 4/2021 | Kim et al. |
| 11,008,601 B2 | 5/2021 | Wang et al. |
| 11,026,994 B2 | 6/2021 | Elliman |
| 11,029,317 B2 | 6/2021 | Sarwal et al. |
| 11,046,745 B2 | 6/2021 | Sahin et al. |
| 11,046,768 B2 | 6/2021 | Cheung et al. |
| 11,052,052 B2 | 7/2021 | Schentag et al. |
| 11,065,343 B2 | 7/2021 | Park et al. |
| 11,066,476 B2 | 7/2021 | Fang et al. |
| 11,084,876 B2 | 8/2021 | Kufer et al. |
| 11,091,547 B2 | 8/2021 | Ferrone et al. |
| 11,098,079 B2 | 8/2021 | Hoang et al. |
| 11,098,115 B2 | 8/2021 | Willemsen et al. |
| 11,123,438 B2 | 9/2021 | Li et al. |
| 11,124,568 B1 | 9/2021 | Ahmed et al. |
| 11,124,578 B2 | 9/2021 | Heusser et al. |
| 11,147,886 B2 | 10/2021 | Ng et al. |
| 11,154,617 B2 | 10/2021 | Baeuerle et al. |
| 11,155,622 B2 | 10/2021 | Brown et al. |
| 11,160,876 B2 | 11/2021 | Markovic et al. |
| 11,161,906 B2 | 11/2021 | Lowman et al. |
| 11,167,040 B2 | 11/2021 | Kim et al. |
| 11,173,214 B2 | 11/2021 | Kim et al. |
| 11,174,323 B2 | 11/2021 | Marasco et al. |
| 11,186,638 B2 | 11/2021 | Snell et al. |

(56) References Cited

U.S. PATENT DOCUMENTS

| | | |
|---|---|---|
| 11,193,155 B2 | 12/2021 | Wang et al. |
| 11,220,551 B2 | 1/2022 | Moffat et al. |
| 11,306,142 B2 | 4/2022 | Nathwani et al. |
| 11,311,631 B2 | 4/2022 | Markovic et al. |
| 11,332,544 B2 | 5/2022 | Davidson et al. |
| 11,339,225 B2 | 5/2022 | Li et al. |
| 11,377,485 B2 | 7/2022 | Wong et al. |
| 11,396,547 B2 | 7/2022 | Bai et al. |
| 11,396,554 B2 | 7/2022 | Soliman |
| 11,413,353 B2 | 8/2022 | Kim et al. |
| 11,414,491 B2 | 8/2022 | Russell et al. |
| 11,419,933 B2 | 8/2022 | Kanapuram et al. |
| 11,427,644 B2 | 8/2022 | Stuhler |
| 11,433,141 B2 | 9/2022 | Akiyama et al. |
| 11,434,291 B2 | 9/2022 | Leon et al. |
| 2001/0044416 A1 | 11/2001 | McCluskie et al. |
| 2002/0006403 A1 | 1/2002 | Yu et al. |
| 2003/0017979 A1 | 1/2003 | Mack et al. |
| 2003/0083472 A1 | 5/2003 | Tamatani et al. |
| 2003/0108548 A1 | 6/2003 | Bluestone et al. |
| 2003/0194403 A1 | 10/2003 | van de Winkel et al. |
| 2003/0216551 A1 | 11/2003 | Delovitch |
| 2003/0235583 A1 | 12/2003 | Sturis et al. |
| 2004/0023885 A1 | 2/2004 | Brand et al. |
| 2004/0024208 A1 | 2/2004 | Das et al. |
| 2004/0037826 A1 | 2/2004 | Michelsen et al. |
| 2004/0054186 A1 | 3/2004 | Das et al. |
| 2004/0072749 A1 | 4/2004 | Zochoer et al. |
| 2004/0073026 A1 | 4/2004 | Das et al. |
| 2004/0077875 A1 | 4/2004 | Das et al. |
| 2004/0082664 A1 | 4/2004 | Won et al. |
| 2004/0170626 A1 | 9/2004 | Schuurman et al. |
| 2004/0204429 A1 | 10/2004 | Yuan |
| 2004/0209801 A1 | 10/2004 | Brand et al. |
| 2004/0229788 A1 | 11/2004 | Tamatani et al. |
| 2005/0009870 A1 | 1/2005 | Sher et al. |
| 2005/0014786 A1 | 1/2005 | Sun et al. |
| 2005/0043233 A1 | 2/2005 | Stefanic et al. |
| 2005/0054659 A1 | 3/2005 | Ellsworth et al. |
| 2005/0080087 A1 | 4/2005 | Pendri et al. |
| 2005/0119269 A1 | 6/2005 | Rao et al. |
| 2005/0143381 A1 | 6/2005 | Yu et al. |
| 2005/0147581 A1 | 7/2005 | Zamiri et al. |
| 2005/0171110 A1 | 8/2005 | Yu et al. |
| 2005/0176028 A1 | 8/2005 | Hofmeister et al. |
| 2005/0191702 A1 | 9/2005 | Mack et al. |
| 2005/0250691 A1 | 11/2005 | Robertson et al. |
| 2006/0002933 A1 | 1/2006 | Bluestone et al. |
| 2006/0057620 A1 | 3/2006 | Krause |
| 2006/0058311 A1 | 3/2006 | Munzert et al. |
| 2006/0062780 A1 | 3/2006 | Zocher et al. |
| 2006/0079563 A1 | 4/2006 | Das et al. |
| 2006/0177896 A1 | 8/2006 | Mach et al. |
| 2006/0183674 A1 | 8/2006 | Brand et al. |
| 2006/0194725 A1 | 8/2006 | Rasmussen et al. |
| 2006/0235201 A1 | 10/2006 | Kischel |
| 2006/0275292 A1 | 12/2006 | Delovitch |
| 2006/0292142 A1 | 12/2006 | Bluestone et al. |
| 2007/0053954 A1 | 3/2007 | Rowe et al. |
| 2007/0065437 A1 | 3/2007 | Elson et al. |
| 2007/0071675 A1 | 3/2007 | Wu et al. |
| 2007/0077246 A1 | 4/2007 | Koenig et al. |
| 2007/0082841 A1 | 4/2007 | Higuchi et al. |
| 2007/0086942 A1 | 4/2007 | Chang et al. |
| 2007/0087971 A1 | 4/2007 | Levetan et al. |
| 2007/0190045 A1 | 8/2007 | Herold et al. |
| 2007/0190052 A1 | 8/2007 | Herold et al. |
| 2007/0249529 A1 | 10/2007 | Hofmeister et al. |
| 2007/0264229 A1 | 11/2007 | Strominger |
| 2007/0292416 A1 | 12/2007 | Rother et al. |
| 2007/0292430 A1 | 12/2007 | Blumenkopf et al. |
| 2008/0009537 A1 | 1/2008 | Sakai |
| 2008/0026378 A1 | 1/2008 | Bottazzo et al. |
| 2008/0044413 A1 | 2/2008 | Hammond et al. |
| 2008/0138339 A1 | 6/2008 | Huang et al. |
| 2008/0171014 A1 | 7/2008 | Wu et al. |
| 2008/0171049 A1 | 7/2008 | Yuan |
| 2008/0207594 A1 | 8/2008 | Mussmann et al. |
| 2008/0213288 A1 | 9/2008 | Michelsen et al. |
| 2008/0248055 A1 | 10/2008 | Robertson et al. |
| 2008/0253991 A1 | 10/2008 | Jevnikar et al. |
| 2008/0254040 A1 | 10/2008 | Stefanic et al. |
| 2008/0287423 A1 | 11/2008 | Mussmann et al. |
| 2009/0041769 A1 | 2/2009 | Peach et al. |
| 2009/0117102 A1 | 5/2009 | Cruz |
| 2009/0142338 A1 | 6/2009 | Levetan |
| 2009/0148389 A1 | 6/2009 | Rottiers et al. |
| 2009/0258001 A1 | 10/2009 | Ponath et al. |
| 2009/0269337 A1 | 10/2009 | Brand et al. |
| 2009/0297524 A1 | 12/2009 | Grant et al. |
| 2009/0324609 A1 | 12/2009 | Lodie et al. |
| 2010/0008929 A1 | 1/2010 | van de Winkel et al. |
| 2010/0008932 A1 | 1/2010 | Bensussan et al. |
| 2010/0015142 A1 | 1/2010 | Koenig |
| 2010/0041602 A1 | 2/2010 | Hagerty et al. |
| 2010/0041632 A1 | 2/2010 | Zhang et al. |
| 2010/0047239 A1 | 2/2010 | Wu et al. |
| 2010/0061984 A1 | 3/2010 | Greene et al. |
| 2010/0076178 A1 | 3/2010 | Ghayur et al. |
| 2010/0129357 A1 | 5/2010 | Garcia-Martinez et al. |
| 2010/0129361 A1 | 5/2010 | Ho et al. |
| 2010/0150829 A1 | 6/2010 | Garcia-Martinez et al. |
| 2010/0183554 A1 | 7/2010 | Mach et al. |
| 2010/0183612 A1 | 7/2010 | Peach et al. |
| 2010/0189773 A1 | 7/2010 | Mortimore et al. |
| 2010/0209437 A1 | 8/2010 | Elson et al. |
| 2010/0247555 A1 | 9/2010 | Self et al. |
| 2010/0260668 A1 | 10/2010 | Ghayur et al. |
| 2011/0002939 A1 | 1/2011 | Melarkode et al. |
| 2011/0020269 A1 | 1/2011 | Strom et al. |
| 2011/0091372 A1 | 4/2011 | Ghayur et al. |
| 2011/0142761 A1 | 6/2011 | Wu et al. |
| 2011/0165066 A1 | 7/2011 | Wu et al. |
| 2011/0165161 A1 | 7/2011 | Lin et al. |
| 2011/0217302 A1 | 9/2011 | Odegard et al. |
| 2011/0250130 A1 | 10/2011 | Benatuil et al. |
| 2011/0256130 A1 | 10/2011 | Schultz et al. |
| 2011/0262440 A1 | 10/2011 | Zugmaier |
| 2011/0263827 A1 | 10/2011 | Ghayur et al. |
| 2011/0280800 A1 | 11/2011 | Wu et al. |
| 2011/0287533 A1 | 11/2011 | Chang |
| 2011/0300142 A1 | 12/2011 | Salford et al. |
| 2012/0014957 A1 | 1/2012 | Ghayur et al. |
| 2012/0045435 A1 | 2/2012 | Deisher |
| 2012/0052065 A1 | 3/2012 | Peach et al. |
| 2012/0076727 A1 | 3/2012 | McBride et al. |
| 2012/0076753 A1 | 3/2012 | Mandelboim et al. |
| 2012/0088678 A1 | 4/2012 | Albani |
| 2012/0195900 A1 | 8/2012 | Ghayur et al. |
| 2012/0201746 A1 | 8/2012 | Liu et al. |
| 2012/0201781 A1 | 8/2012 | Kamath |
| 2012/0230911 A1 | 9/2012 | Hsieh et al. |
| 2012/0237472 A1 | 9/2012 | Kaplin et al. |
| 2012/0258040 A1 | 10/2012 | Exley et al. |
| 2012/0263722 A1 | 10/2012 | Ghayur et al. |
| 2012/0269826 A1 | 10/2012 | McKee et al. |
| 2012/0321623 A1 | 12/2012 | Suciu-Foca et al. |
| 2013/0004416 A1 | 1/2013 | Wu et al. |
| 2013/0039861 A1 | 2/2013 | Regino et al. |
| 2013/0078238 A1 | 3/2013 | Ilan et al. |
| 2013/0095103 A1 | 4/2013 | Baeuerle et al. |
| 2013/0095121 A1 | 4/2013 | Brennan et al. |
| 2013/0115207 A1 | 5/2013 | Faustman |
| 2013/0129723 A1 | 5/2013 | Blankenship et al. |
| 2013/0171142 A1 | 7/2013 | Brennan et al. |
| 2013/0190233 A1 | 7/2013 | Levetan et al. |
| 2013/0225427 A1 | 8/2013 | Albani |
| 2013/0251671 A1 | 9/2013 | Kaufman |
| 2013/0323247 A1 | 12/2013 | Zugmaier et al. |
| 2014/0066600 A1 | 3/2014 | Chang |
| 2014/0088295 A1 | 3/2014 | Smith et al. |
| 2014/0099313 A1 | 4/2014 | Wu et al. |
| 2014/0099318 A1 | 4/2014 | Huang et al. |
| 2014/0112898 A1 | 4/2014 | Mathis |

(56) References Cited

U.S. PATENT DOCUMENTS

| | | |
|---|---|---|
| 2014/0120097 A1 | 5/2014 | Levetan |
| 2014/0134171 A1 | 5/2014 | Ghayur et al. |
| 2014/0141020 A1 | 5/2014 | Pages et al. |
| 2014/0147413 A1 | 5/2014 | Chen et al. |
| 2014/0193399 A1 | 7/2014 | Mach et al. |
| 2014/0212425 A1 | 7/2014 | Chang et al. |
| 2014/0220020 A1 | 8/2014 | Wu et al. |
| 2014/0220029 A1 | 8/2014 | Michelsen |
| 2014/0234405 A1 | 8/2014 | Levetan |
| 2014/0235552 A1 | 8/2014 | Levetan |
| 2014/0242077 A1 | 8/2014 | Choi et al. |
| 2014/0242081 A1 | 8/2014 | Hammond et al. |
| 2014/0255956 A1 | 9/2014 | Lipes et al. |
| 2014/0271464 A1 | 9/2014 | Garcia-Martinez et al. |
| 2015/0004167 A1 | 1/2015 | Wu et al. |
| 2015/0010508 A1 | 1/2015 | Levetan et al. |
| 2015/0018360 A1 | 1/2015 | Halse et al. |
| 2015/0023977 A1 | 1/2015 | Fraunhofer et al. |
| 2015/0044212 A1 | 2/2015 | Xiao et al. |
| 2015/0050238 A1 | 2/2015 | Kamath |
| 2015/0056167 A1 | 2/2015 | Levetan et al. |
| 2015/0079088 A1 | 3/2015 | Lowman et al. |
| 2015/0079093 A1 | 3/2015 | Stuhler |
| 2015/0086548 A1 | 3/2015 | Levetan |
| 2015/0104452 A1 | 4/2015 | Ghayur et al. |
| 2015/0118252 A1 | 4/2015 | Ho et al. |
| 2015/0140007 A1 | 5/2015 | Wang et al. |
| 2015/0166661 A1 | 6/2015 | Chen et al. |
| 2015/0174111 A1 | 6/2015 | Levetan |
| 2015/0175699 A1 | 6/2015 | Ellis et al. |
| 2015/0183875 A1 | 7/2015 | Cobbold et al. |
| 2015/0231241 A1 | 8/2015 | Chang et al. |
| 2015/0252110 A1 | 9/2015 | Hansen et al. |
| 2015/0274844 A1 | 10/2015 | Blankenship et al. |
| 2015/0297598 A1 | 10/2015 | Friedman et al. |
| 2015/0299320 A1 | 10/2015 | Exley et al. |
| 2015/0361170 A1 | 12/2015 | Fraunhofer et al. |
| 2016/0039942 A1 | 2/2016 | Cobbold et al. |
| 2016/0046714 A1 | 2/2016 | Koenig et al. |
| 2016/0046730 A1 | 2/2016 | Ghayur et al. |
| 2016/0090416 A1 | 3/2016 | Gunde et al. |
| 2016/0106710 A1 | 4/2016 | Sun et al. |
| 2016/0122436 A1 | 5/2016 | Kufer et al. |
| 2016/0159921 A1 | 6/2016 | D'Angelo et al. |
| 2016/0206682 A1 | 7/2016 | Levetan |
| 2016/0206683 A1 | 7/2016 | Levetan |
| 2016/0213740 A1 | 7/2016 | Levetan |
| 2016/0213741 A1 | 7/2016 | Levetan |
| 2016/0213746 A1 | 7/2016 | Levetan |
| 2016/0215051 A1 | 7/2016 | Sharma et al. |
| 2016/0272703 A1 | 9/2016 | Hsieh et al. |
| 2016/0287622 A1 | 10/2016 | Chang et al. |
| 2016/0289341 A1 | 10/2016 | Wu |
| 2016/0296632 A1 | 10/2016 | Chipman |
| 2016/0311915 A1 | 10/2016 | Pule et al. |
| 2016/0311919 A1 | 10/2016 | Xiao et al. |
| 2016/0317654 A1 | 11/2016 | Noelle et al. |
| 2016/0324798 A1 | 11/2016 | Han et al. |
| 2016/0347850 A1 | 12/2016 | Benatuil et al. |
| 2016/0361360 A1 | 12/2016 | Chang et al. |
| 2017/0015758 A1 | 1/2017 | Hammond et al. |
| 2017/0021017 A1 | 1/2017 | Chang et al. |
| 2017/0022274 A1 | 1/2017 | Chang et al. |
| 2017/0058027 A1 | 3/2017 | Wu et al. |
| 2017/0058043 A1 | 3/2017 | Solman |
| 2017/0073415 A1 | 3/2017 | Urech et al. |
| 2017/0128493 A1 | 5/2017 | Deisher |
| 2017/0137519 A1 | 5/2017 | Huang et al. |
| 2017/0145115 A1 | 5/2017 | Blein et al. |
| 2017/0173117 A1 | 6/2017 | Paulsen et al. |
| 2017/0216218 A1 | 8/2017 | Farokhzad et al. |
| 2017/0218091 A1 | 8/2017 | Ambrosi |
| 2017/0266199 A1 | 9/2017 | Berger et al. |
| 2017/0283446 A1 | 10/2017 | Fan et al. |
| 2017/0304213 A1 | 10/2017 | Shi et al. |
| 2017/0342151 A1 | 11/2017 | Ferrone et al. |
| 2017/0342160 A1 | 11/2017 | Mertens et al. |
| 2017/0362240 A1 | 12/2017 | Allen et al. |
| 2017/0362299 A1 | 12/2017 | Li et al. |
| 2018/0036285 A1 | 2/2018 | Tunac et al. |
| 2018/0057593 A1 | 3/2018 | Dennis |
| 2018/0117152 A1 | 5/2018 | Lee et al. |
| 2018/0134804 A1 | 5/2018 | Scheinberg et al. |
| 2018/0177880 A1 | 6/2018 | Shalibhai |
| 2018/0193477 A1 | 7/2018 | Ng et al. |
| 2018/0237522 A1 | 8/2018 | Snell et al. |
| 2018/0244778 A1 | 8/2018 | Ellis et al. |
| 2018/0251503 A1 | 9/2018 | Ahmed et al. |
| 2018/0273623 A1 | 9/2018 | Cheung et al. |
| 2018/0280507 A1 | 10/2018 | Yu et al. |
| 2018/0291114 A1 | 10/2018 | Ostrand-Rosenberg et al. |
| 2018/0296699 A1 | 10/2018 | Xie |
| 2018/0318230 A1 | 11/2018 | Chopra et al. |
| 2018/0344845 A1 | 12/2018 | Reimann et al. |
| 2018/0346591 A1 | 12/2018 | Soliman |
| 2018/0355064 A1 | 12/2018 | Blein et al. |
| 2019/0004064 A1 | 1/2019 | Chen et al. |
| 2019/0010242 A1 | 1/2019 | Eckelman et al. |
| 2019/0022154 A1 | 1/2019 | Rottiers et al. |
| 2019/0022205 A1 | 2/2019 | Salih et al. |
| 2019/0038733 A1 | 2/2019 | Campana et al. |
| 2019/0046571 A1 | 2/2019 | Campana et al. |
| 2019/0070248 A1 | 3/2019 | Sahin et al. |
| 2019/0077856 A1 | 3/2019 | Scheinberg et al. |
| 2019/0135894 A1 | 5/2019 | Ma et al. |
| 2019/0135918 A1 | 5/2019 | Ollier et al. |
| 2019/0153471 A1 | 5/2019 | Paul et al. |
| 2019/0169296 A1 | 6/2019 | Russell et al. |
| 2019/0170752 A1 | 6/2019 | Luo et al. |
| 2019/0184026 A1 | 6/2019 | Li et al. |
| 2019/0185511 A1 | 6/2019 | Kanne et al. |
| 2019/0194690 A1 | 6/2019 | Champion et al. |
| 2019/0233534 A1 | 8/2019 | Mehlin et al. |
| 2019/0233536 A1 | 8/2019 | Champion et al. |
| 2019/0248924 A1 | 8/2019 | Wu |
| 2019/0276541 A1 | 9/2019 | Eavarone et al. |
| 2019/0284296 A1 | 9/2019 | Stuhler |
| 2019/0284299 A1 | 9/2019 | Liu et al. |
| 2019/0292551 A1 | 9/2019 | Rottiers et al. |
| 2019/0300526 A1 | 10/2019 | Fan et al. |
| 2019/0300609 A1 | 10/2019 | Zugmaier et al. |
| 2019/0314417 A1 | 10/2019 | Wobma et al. |
| 2019/0330362 A1 | 10/2019 | Moffat et al. |
| 2019/0343964 A1 | 11/2019 | Akiyama et al. |
| 2019/0351056 A1 | 11/2019 | Christen et al. |
| 2019/0352421 A1 | 11/2019 | Adams et al. |
| 2019/0359732 A1 | 11/2019 | Cheung et al. |
| 2019/0382497 A1 | 12/2019 | Poirier et al. |
| 2020/0023076 A1 | 1/2020 | Fotin-Mleczek et al. |
| 2020/0024363 A1 | 1/2020 | Teran et al. |
| 2020/0040056 A1 | 2/2020 | DiPersio et al. |
| 2020/0040099 A1 | 2/2020 | Kufer et al. |
| 2020/0048356 A1 | 2/2020 | Liu |
| 2020/0071397 A1 | 3/2020 | DiPersio et al. |
| 2020/0079854 A1 | 3/2020 | Hsiue et al. |
| 2020/0087412 A1 | 3/2020 | Fang et al. |
| 2020/0113940 A1 | 4/2020 | Maus et al. |
| 2020/0157218 A1 | 5/2020 | Nathwani et al. |
| 2020/0157249 A1 | 5/2020 | Wu |
| 2020/0181260 A1 | 6/2020 | Davila |
| 2020/0181264 A1 | 6/2020 | Rossi et al. |
| 2020/0181288 A1 | 6/2020 | Jang et al. |
| 2020/0199169 A1 | 6/2020 | Leong et al. |
| 2020/0199232 A1 | 6/2020 | Qin et al. |
| 2020/0199248 A1 | 6/2020 | Cheung et al. |
| 2020/0206145 A1 | 7/2020 | Shi et al. |
| 2020/0207851 A1 | 7/2020 | Chen et al. |
| 2020/0216859 A1 | 7/2020 | Champion et al. |
| 2020/0239571 A1 | 7/2020 | Bramson et al. |
| 2020/0261574 A1 | 8/2020 | Reimann et al. |
| 2020/0281976 A1 | 9/2020 | Zeng et al. |
| 2020/0308541 A1 | 10/2020 | Ma et al. |
| 2020/0317809 A1 | 10/2020 | Li |
| 2020/0339679 A1 | 10/2020 | Sirianni et al. |

(56) References Cited

U.S. PATENT DOCUMENTS

| | | |
|---|---|---|
| 2020/0339686 A1 | 10/2020 | Sato et al. |
| 2020/0384107 A1 | 12/2020 | Yu et al. |
| 2020/0399368 A1 | 12/2020 | Leon et al. |
| 2020/0399370 A1 | 12/2020 | Sahin et al. |
| 2020/0407452 A1 | 12/2020 | Michieli |
| 2021/0000957 A1 | 1/2021 | Shailubhai |
| 2021/0009596 A1 | 1/2021 | Fan et al. |
| 2021/0009691 A1 | 1/2021 | Mach et al. |
| 2021/0024639 A1 | 1/2021 | Michieli |
| 2021/0032333 A1 | 2/2021 | Leon et al. |
| 2021/0038646 A1 | 2/2021 | Maus et al. |
| 2021/0046112 A1 | 2/2021 | Campana et al. |
| 2021/0052612 A1 | 2/2021 | Fan et al. |
| 2021/0085735 A1 | 3/2021 | Finer et al. |
| 2021/0087267 A1 | 3/2021 | Miano et al. |
| 2021/0107985 A1 | 4/2021 | Schuurman et al. |
| 2021/0108213 A1 | 4/2021 | Rashid et al. |
| 2021/0113519 A1 | 4/2021 | Whitehead et al. |
| 2021/0113550 A1 | 4/2021 | Khleif et al. |
| 2021/0113709 A1 | 4/2021 | Demetriou et al. |
| 2021/0130464 A1 | 5/2021 | Leon et al. |
| 2021/0139577 A1 | 5/2021 | Dillon et al. |
| 2021/0139851 A1 | 5/2021 | Chuang et al. |
| 2021/0154247 A1 | 5/2021 | Rottiers et al. |
| 2021/0155713 A1 | 5/2021 | Didonato et al. |
| 2021/0163620 A1 | 6/2021 | Granda et al. |
| 2021/0171661 A1 | 6/2021 | Blein et al. |
| 2021/0177755 A1 | 6/2021 | Dumontet et al. |
| 2021/0180072 A1 | 6/2021 | Rottiers et al. |
| 2021/0188983 A1 | 6/2021 | Robert et al. |
| 2021/0198368 A1 | 7/2021 | Daley et al. |
| 2021/0205248 A1 | 7/2021 | Kaufman et al. |
| 2021/0206853 A1 | 7/2021 | Lindhofer et al. |
| 2021/0214440 A1 | 7/2021 | Ganesan et al. |
| 2021/0214458 A1 | 7/2021 | Liu et al. |
| 2021/0236466 A1 | 8/2021 | Roush et al. |
| 2021/0238291 A1 | 8/2021 | Lowman et al. |
| 2021/0238607 A1 | 8/2021 | Fierabracci |
| 2021/0244815 A1 | 8/2021 | Lee et al. |
| 2021/0246211 A1 | 8/2021 | Goldberg et al. |
| 2021/0251954 A1 | 8/2021 | Sun et al. |
| 2021/0253636 A1 | 8/2021 | Yu et al. |
| 2021/0260173 A1 | 8/2021 | Kjellman et al. |
| 2021/0261645 A1 | 8/2021 | Huang et al. |
| 2021/0261646 A1 | 8/2021 | McGinness et al. |
| 2021/0261649 A1 | 8/2021 | Parry et al. |
| 2021/0269525 A1 | 8/2021 | Parry et al. |
| 2021/0269841 A1 | 8/2021 | Parry et al. |
| 2021/0277127 A1 | 9/2021 | Zhang et al. |
| 2021/0284746 A1 | 9/2021 | Liu et al. |
| 2021/0292423 A1 | 9/2021 | Albrecht et al. |
| 2021/0301015 A1 | 9/2021 | Tseng |
| 2021/0309750 A1 | 10/2021 | Sampson et al. |
| 2021/0324079 A1 | 10/2021 | Cheung et al. |
| 2021/0332134 A1 | 10/2021 | Shibayama et al. |
| 2021/0332334 A1 | 10/2021 | McGinness et al. |
| 2021/0338836 A1 | 11/2021 | Yu et al. |
| 2021/0340219 A1 | 11/2021 | McGinness et al. |
| 2021/0348191 A1 | 11/2021 | Pule et al. |
| 2021/0349094 A1 | 11/2021 | Vasu |
| 2021/0353751 A1 | 11/2021 | Kaufman et al. |
| 2021/0363180 A1 | 11/2021 | Hoang et al. |
| 2021/0363270 A1 | 11/2021 | Park et al. |
| 2021/0371927 A1 | 12/2021 | Gysemans et al. |
| 2021/0379046 A1 | 12/2021 | Scheinberg et al. |
| 2021/0382053 A1 | 12/2021 | Vasiljeva et al. |
| 2021/0386680 A1 | 12/2021 | Cui et al. |
| 2021/0388017 A1 | 12/2021 | Park et al. |
| 2021/0388388 A1 | 12/2021 | Song et al. |
| 2021/0393795 A1 | 12/2021 | Park et al. |
| 2021/0395339 A1 | 12/2021 | Alitalo et al. |
| 2021/0402005 A1 | 12/2021 | Markovic et al. |
| 2022/0002398 A1 | 1/2022 | Thiele et al. |
| 2022/0002407 A1 | 1/2022 | Li et al. |
| 2022/0002408 A1 | 1/2022 | Yuan et al. |
| 2022/0002431 A1 | 1/2022 | Li et al. |
| 2022/0008533 A1 | 1/2022 | Shailubhai |
| 2022/0033427 A1 | 2/2022 | Lourenco et al. |
| 2022/0034903 A1 | 2/2022 | Chen et al. |
| 2022/0041720 A1 | 2/2022 | Leon et al. |
| 2022/0041721 A1 | 2/2022 | Zhang et al. |
| 2022/0041724 A1 | 2/2022 | Twitty et al. |
| 2022/0048961 A1 | 2/2022 | Crook et al. |
| 2022/0056132 A1 | 2/2022 | Qin et al. |
| 2022/0057398 A1 | 2/2022 | Sarvetnick et al. |
| 2022/0073640 A1 | 3/2022 | Moffat et al. |
| 2022/0088196 A1 | 3/2022 | Bauerle et al. |
| 2022/0098307 A1 | 3/2022 | Zhang et al. |
| 2022/0098324 A1 | 3/2022 | Weiner et al. |
| 2022/0098329 A1 | 3/2022 | Santich et al. |
| 2022/0105193 A1 | 4/2022 | Li et al. |
| 2022/0118104 A1 | 4/2022 | Park et al. |
| 2022/0119478 A1 | 4/2022 | Spear et al. |
| 2022/0119549 A1 | 4/2022 | Zhang et al. |
| 2022/0125941 A1 | 4/2022 | Ban et al. |
| 2022/0133887 A1 | 5/2022 | Reimann |
| 2022/0135678 A1 | 5/2022 | Chaudary |
| 2022/0135680 A1 | 5/2022 | Tran et al. |
| 2022/0143291 A1 | 5/2022 | Poirier |
| 2022/0144916 A1 | 5/2022 | Maynard et al. |
| 2022/0144947 A1 | 5/2022 | Smith et al. |
| 2022/0152109 A1 | 5/2022 | Coukos et al. |
| 2022/0152216 A1 | 5/2022 | Sanyal |
| 2022/0153840 A1 | 5/2022 | Qui |
| 2022/0153843 A1 | 5/2022 | Liu et al. |
| 2022/0160887 A1 | 5/2022 | Matray et al. |
| 2022/0160891 A1 | 5/2022 | Green et al. |
| 2022/0160895 A1 | 5/2022 | Iles-Somaratne |
| 2022/0162297 A1 | 5/2022 | Basi |
| 2022/0162335 A1 | 5/2022 | Wang et al. |
| 2022/0168433 A1 | 6/2022 | Matray et al. |
| 2022/0177581 A1 | 6/2022 | Cheung et al. |
| 2022/0177583 A1 | 6/2022 | Conklin et al. |
| 2022/0177600 A1 | 6/2022 | Campbell et al. |
| 2022/0184043 A1 | 6/2022 | Sun et al. |
| 2022/0202950 A1 | 6/2022 | Brahmbhatt et al. |
| 2022/0204621 A1 | 6/2022 | Nathwani et al. |
| 2022/0211870 A1 | 7/2022 | Markovic et al. |
| 2022/0218818 A1 | 7/2022 | Szalay |
| 2022/0218840 A1 | 7/2022 | Kim et al. |
| 2022/0220556 A1 | 7/2022 | Khatri et al. |
| 2022/0235115 A1 | 7/2022 | Li et al. |
| 2022/0235143 A1 | 7/2022 | Spriggs et al. |
| 2022/0242970 A1 | 8/2022 | Davidson et al. |
| 2022/0249566 A1 | 8/2022 | Culshaw et al. |
| 2022/0249696 A1 | 8/2022 | Green et al. |
| 2022/0251200 A1 | 8/2022 | Lewis et al. |
| 2022/0251238 A1 | 8/2022 | Li et al. |
| 2022/0257760 A1 | 8/2022 | Cripe et al. |
| 2022/0265595 A1 | 8/2022 | Cooke et al. |
| 2022/0280440 A1 | 9/2022 | Morales et al. |
| 2022/0298242 A1 | 9/2022 | Yang et al. |
| 2022/0306715 A1 | 9/2022 | Schreiber et al. |
| 2022/0306735 A1 | 9/2022 | Dekosky et al. |
| 2022/0315653 A1 | 10/2022 | Kiefer et al. |

FOREIGN PATENT DOCUMENTS

| | | |
|---|---|---|
| EP | 1687066 B1 | 8/2006 |
| EP | 1691833 B1 | 8/2006 |
| EP | 1753783 B1 | 2/2007 |
| EP | 1697370 B1 | 4/2007 |
| EP | 1697371 B1 | 4/2007 |
| EP | 1397153 B1 | 4/2008 |
| EP | 1686130 B1 | 2/2009 |
| EP | 2037961 B1 | 3/2009 |
| EP | 1379270 B1 | 9/2009 |
| EP | 1337527 B1 | 10/2009 |
| EP | 1837031 B1 | 10/2009 |
| EP | 2193142 B1 | 6/2010 |
| EP | 1716178 B1 | 8/2010 |
| EP | 1827492 B1 | 8/2010 |
| EP | 1697421 B1 | 9/2010 |
| EP | 1673398 B1 | 12/2010 |

(56) References Cited

FOREIGN PATENT DOCUMENTS

| | | |
|---|---|---|
| EP | 2270051 B1 | 1/2011 |
| EP | 1451192 B1 | 2/2011 |
| EP | 1798240 B1 | 4/2011 |
| EP | 2397189 B1 | 12/2011 |
| EP | 1879591 B1 | 1/2012 |
| EP | 2288372 B1 | 2/2012 |
| EP | 2096120 B1 | 3/2012 |
| EP | 1578397 B1 | 12/2012 |
| EP | 2119450 B1 | 2/2013 |
| EP | 1973573 B1 | 5/2013 |
| EP | 1797126 B1 | 10/2013 |
| EP | 1613628 B1 | 11/2013 |
| EP | 1740946 B1 | 11/2013 |
| EP | 2164500 B1 | 12/2013 |
| EP | 2408468 B1 | 4/2014 |
| EP | 2714733 B1 | 4/2014 |
| EP | 2755999 B1 | 7/2014 |
| EP | 1976886 B1 | 12/2014 |
| EP | 2814963 B1 | 12/2014 |
| EP | 2344539 B1 | 2/2015 |
| EP | 2892924 B1 | 7/2015 |
| EP | 2342227 B1 | 10/2015 |
| EP | 2551347 B1 | 11/2015 |
| EP | 2295066 B1 | 4/2016 |
| EP | 3024484 B1 | 6/2016 |
| EP | 1957100 B1 | 7/2016 |
| EP | 1976880 B1 | 7/2016 |
| EP | 2292664 B1 | 11/2016 |
| EP | 2029145 B1 | 1/2017 |
| EP | 3464352 B1 | 5/2017 |
| EP | 2066174 B1 | 11/2017 |
| EP | 1629013 B1 | 1/2018 |
| EP | 2854845 B1 | 3/2018 |
| EP | 2793923 B1 | 5/2018 |
| EP | 3024851 B1 | 5/2018 |
| EP | 2835379 B1 | 7/2018 |
| EP | 2764362 B1 | 9/2018 |
| EP | 2878308 B1 | 10/2018 |
| EP | 1629012 B1 | 11/2018 |
| EP | 3129483 B1 | 11/2018 |
| EP | 2968545 B1 | 3/2019 |
| EP | 2982696 B1 | 3/2019 |
| EP | 3330293 B1 | 7/2019 |
| EP | 3087095 B1 | 8/2019 |
| EP | 2993186 B1 | 9/2019 |
| EP | 2793912 B1 | 3/2020 |
| EP | 3044234 B1 | 3/2020 |
| EP | 3083689 B1 | 5/2020 |
| EP | 3186277 B1 | 10/2020 |
| EP | 3227297 B1 | 1/2021 |
| EP | 3791931 A1 | 3/2021 |
| EP | 3318565 B1 | 4/2021 |
| EP | 3402494 B1 | 4/2021 |
| EP | 3402499 B1 | 4/2021 |
| EP | 2819701 B2 | 6/2021 |
| EP | 3310811 B1 | 6/2021 |
| EP | 3504316 B1 | 6/2021 |
| EP | 2242504 B1 | 7/2021 |
| EP | 3268391 B1 | 8/2021 |
| EP | 2742953 B1 | 9/2021 |
| EP | 3297672 B1 | 9/2021 |
| EP | 3389682 B1 | 11/2021 |
| EP | 3439658 B1 | 11/2021 |
| EP | 3194439 B1 | 1/2022 |
| EP | 3230311 B1 | 1/2022 |
| EP | 3703718 B1 | 1/2022 |
| EP | 3434760 B1 | 5/2022 |
| WO | WO2007147090 A2 | 12/2007 |
| WO | WO2014165818 A2 | 10/2014 |
| WO | WO2015073833 | 5/2015 |
| WO | WO2017125897 A1 | 7/2017 |
| WO | WO2017193956 A1 | 11/2017 |
| WO | WO2018037416 A1 | 3/2018 |
| WO | WO2018068652 A1 | 4/2018 |
| WO | WO2018115906 A1 | 6/2018 |
| WO | WO2018120842 A1 | 7/2018 |
| WO | WO2018177371 A1 | 10/2018 |
| WO | WO2018178123 A1 | 10/2018 |
| WO | WO2018237192 A1 | 12/2018 |
| WO | 2019050465 A1 | 3/2019 |
| WO | WO2019091384 A1 | 5/2019 |
| WO | WO2019094669 A2 | 5/2019 |
| WO | WO2019126133 A1 | 6/2019 |
| WO | WO2019133847 A1 | 7/2019 |
| WO | WO2019185864 A1 | 10/2019 |
| WO | WO2019195535 A1 | 10/2019 |
| WO | WO2019204434 A1 | 10/2019 |
| WO | WO2019215772 A1 | 11/2019 |
| WO | WO2019219913 A1 | 11/2019 |
| WO | WO2019222082 A1 | 11/2019 |
| WO | WO2019226894 A1 | 11/2019 |
| WO | WO2019234241 A1 | 12/2019 |
| WO | 2020001344 A1 | 1/2020 |
| WO | 2020006486 A1 | 1/2020 |
| WO | WO2020014097 A1 | 1/2020 |
| WO | WO2020028444 A1 | 2/2020 |
| WO | 2020047176 A1 | 3/2020 |
| WO | 2020056037 A1 | 3/2020 |
| WO | WO2020053301 A1 | 3/2020 |
| WO | WO2020056170 A1 | 3/2020 |
| WO | WO2020081885 A1 | 4/2020 |
| WO | WO2020081886 A1 | 4/2020 |
| WO | WO2020086423 A1 | 4/2020 |
| WO | WO2020089396 A2 | 5/2020 |
| WO | WO2020092743 A2 | 5/2020 |
| WO | 2020112987 A1 | 6/2020 |
| WO | WO2020113164 A1 | 6/2020 |
| WO | WO2020123806 A1 | 6/2020 |
| WO | WO2020124032 A1 | 6/2020 |
| WO | 2020168555 A1 | 8/2020 |
| WO | WO2020160310 A1 | 8/2020 |
| WO | WO2020168554 A1 | 8/2020 |
| WO | WO2020172259 A1 | 8/2020 |
| WO | 2020190217 A2 | 9/2020 |
| WO | WO2020185763 A1 | 9/2020 |
| WO | WO2020186974 A1 | 9/2020 |
| WO | WO2020191344 A1 | 9/2020 |
| WO | 2020206063 A1 | 10/2020 |
| WO | WO2020191486 A1 | 10/2020 |
| WO | WO2020210232 A1 | 10/2020 |
| WO | WO2020210843 A2 | 10/2020 |
| WO | WO2020214928 A1 | 10/2020 |
| WO | WO2020222010 A1 | 11/2020 |
| WO | WO2020222011 A1 | 11/2020 |
| WO | WO2020223279 A1 | 11/2020 |
| WO | WO2020226854 A2 | 11/2020 |
| WO | WO2020227538 A1 | 11/2020 |
| WO | WO2020229553 A1 | 11/2020 |
| WO | WO2020232247 A1 | 11/2020 |
| WO | 2020247867 A1 | 12/2020 |
| WO | 2020247871 A2 | 12/2020 |
| WO | WO2020247385 A1 | 12/2020 |
| WO | WO2021001458 A1 | 1/2021 |
| WO | WO2021016316 A1 | 1/2021 |
| WO | WO2021038975 A1 | 3/2021 |
| WO | WO2021041725 A1 | 3/2021 |
| WO | WO2021041958 A1 | 3/2021 |
| WO | WO2021044008 A1 | 3/2021 |
| WO | WO2021048724 A1 | 3/2021 |
| WO | WO2021060638 A1 | 4/2021 |
| WO | WO2021064069 A1 | 4/2021 |
| WO | WO2021071319 A1 | 4/2021 |
| WO | WO2021072264 A1 | 4/2021 |
| WO | WO2021090321 A1 | 5/2021 |
| WO | WO2021092672 A1 | 5/2021 |
| WO | WO2021110935 A1 | 6/2021 |
| WO | WO2021111185 A1 | 6/2021 |
| WO | WO2021116398 A1 | 6/2021 |
| WO | WO2021119585 A1 | 6/2021 |
| WO | WO2021127489 A1 | 6/2021 |
| WO | WO2021130492 A1 | 7/2021 |
| WO | WO2021138600 A1 | 7/2021 |
| WO | WO2021144315 A1 | 7/2021 |
| WO | WO2021146328 A1 | 7/2021 |

(56) References Cited

FOREIGN PATENT DOCUMENTS

| | | |
|---|---|---|
| WO | WO2021155071 A1 | 8/2021 |
| WO | WO2021165248 A1 | 8/2021 |
| WO | WO2021173783 A1 | 9/2021 |
| WO | WO2021183839 A2 | 9/2021 |
| WO | WO2021188590 A2 | 9/2021 |
| WO | WO2021195067 A1 | 9/2021 |
| WO | WO2021202726 A2 | 10/2021 |
| WO | WO2021202770 A2 | 10/2021 |
| WO | WO2021207828 A1 | 10/2021 |
| WO | WO2021213421 A1 | 10/2021 |
| WO | WO2021216460 A1 | 10/2021 |
| WO | WO2021216972 A1 | 10/2021 |
| WO | WO2021222746 A2 | 11/2021 |
| WO | WO2021222861 A1 | 11/2021 |
| WO | WO2021243206 A1 | 12/2021 |
| WO | WO2021252780 A2 | 12/2021 |
| WO | WO2021252917 A2 | 12/2021 |
| WO | WO2021254574 A2 | 12/2021 |
| WO | WO2022013872 A1 | 1/2022 |
| WO | WO2022018262 A1 | 1/2022 |
| WO | WO2022026439 A2 | 2/2022 |
| WO | WO2022026939 A2 | 2/2022 |
| WO | WO2022027039 A1 | 2/2022 |
| WO | WO2022029438 A1 | 2/2022 |
| WO | WO2022032004 A2 | 2/2022 |
| WO | WO2022033419 A2 | 2/2022 |
| WO | WO2022035888 A2 | 2/2022 |
| WO | WO2022036495 A1 | 2/2022 |
| WO | WO2022037520 A1 | 2/2022 |
| WO | WO2022038365 A2 | 2/2022 |
| WO | WO2022040429 A2 | 2/2022 |
| WO | WO2022040603 A2 | 2/2022 |
| WO | WO2022045247 A1 | 3/2022 |
| WO | WO2022053036 A1 | 3/2022 |
| WO | WO2022058298 A1 | 3/2022 |
| WO | WO2022060832 A1 | 3/2022 |
| WO | WO2022063302 A1 | 3/2022 |
| WO | WO2022067224 A1 | 3/2022 |
| WO | WO2022076898 A1 | 4/2022 |
| WO | WO2022077108 A1 | 4/2022 |
| WO | WO2022083853 A1 | 4/2022 |
| WO | WO2022087149 A2 | 4/2022 |
| WO | WO2022090714 A1 | 5/2022 |
| WO | WO2022090723 A1 | 5/2022 |
| WO | WO2022090724 A1 | 5/2022 |
| WO | WO2022098771 A1 | 5/2022 |
| WO | WO2022099032 A1 | 5/2022 |
| WO | WO2022099076 A1 | 5/2022 |
| WO | WO2022105787 A1 | 5/2022 |
| WO | WO2022115474 A1 | 6/2022 |
| WO | WO2022115719 A1 | 6/2022 |
| WO | WO2022116480 A1 | 6/2022 |
| WO | WO2022125482 A1 | 6/2022 |
| WO | WO2022125566 A1 | 6/2022 |
| WO | WO2022129910 A1 | 6/2022 |
| WO | WO2022132929 A2 | 6/2022 |
| WO | WO2022148736 A1 | 7/2022 |
| WO | WO2022157352 A1 | 7/2022 |
| WO | WO2022159555 A1 | 7/2022 |
| WO | WO2022162192 A1 | 8/2022 |
| WO | WO2022164935 A1 | 8/2022 |
| WO | WO2022167689 A1 | 8/2022 |
| WO | WO2022169825 A1 | 8/2022 |
| WO | WO2022179004 A1 | 9/2022 |
| WO | WO2022183018 A1 | 9/2022 |
| WO | WO2022187586 A1 | 9/2022 |
| WO | WO2022192236 A1 | 9/2022 |
| WO | WO2022194264 A1 | 9/2022 |
| WO | WO2022195241 A1 | 9/2022 |
| WO | WO2022197907 A1 | 9/2022 |
| WO | WO2022199555 A1 | 9/2022 |

OTHER PUBLICATIONS

Wherrett et al., "Prevention of Type 1 Diabetes" Endocrinology and Metabolism Clinics of North America, vol. 38, No. 4, pp. 777-792, Dec. 1, 2009.

Wu et al., "Risk Factors and Primary Prevention Trials for Type 1 Diabetes", International Journal of Biological Sciences, vol. 9, No. 7, pp. 666-679, Jul. 18, 2013.

American Diabetes Association, "2. Classification and Diagnosis of Diabetes: Standards of Medical Care in Diabetes—2019" Diabetes Care, vol. 42, Suppl. 1, pp. S13-S28, Jan. 2019.

Atkinson et al., "The Challenge of Modulating Beta-Cell Autoimmunity in Type 1 Diabetes" Lancet Diabetes Endocrinol, vol. 7, pp. 52-64, 2019.

Bingley et al., "Type 1 Diabetes TrialNet: A Multifaceted Approach to Bringing Disease-Modifying Therapy to Clinical Use in Type 1 Diabetes" Diabetes Care, vol. 41, pp. 653-661, Apr. 2018.

Cox D., "Regression Models and Life Tables" Journal of the Royal Statistical Society, Series B, vol. 34, No. 2, pp. 187-220, 1972.

Demeester et al., "Preexisting Insulin Autoantibodies Predice Efficacy of Otelixizumab in Preserving Residual beta-Cell Function in Recent-Onset Type 1 Diabetes" Diabetese Care, vol. 3, No. 4, pp. 644-651, Apr. 2015.

Diabetes Study Group, "Effects of Insulin in Relatives of Patients with Type 1 Diabetes Mellitus" New England Journal of Medicine, vol. 346, No. 22, pp. 1685-1691, May 30, 2002.

Espluges et al., "Control of TH17 Cells Occurs in the Small Intestine" Nature, vol. 475, pp. 514-520, Jul. 28, 2011.

Gale et al., "European Nicotinamide Diabetes Intervention Trial (ENDIT): A Randomised Controlled Trial of Intervention Before the Onset of Type 1 Diabetes" Lancet, vol. 363, pp. 925-931, Mar. 20, 2004.

Greenbaum et al., "Fall in C-Peptide During First 2 Years from Diagnosis: Evidence of at Least Two Distinct Phases from Composite TrialNet Data" Diabetes, vol. 61, pp. 2066-2073, Aug. 2012.

Hagopian et al., "Teplizumab Preserves C-Peptide in Recent-Onset Type 1 Diabetes—Two-Year Results from the Randomized, Placebo-Controlled Protégé Trial" Diabetes, vol. 62, pp. 3901-3908, Nov. 2013.

Herold et al., "Anti-CD3 Monoclonal Antibody in New-Onset Type 1 Diabetes Mellitus" New England Journal of Medicine, vol. 346, pp. 1692-1698, May 30, 2002.

Herold et al., "A Single Course of Anti-CD3 Monoclonal Antibody hOKT3γ1(Ala-Ala) Results in Improvement in C-Peptide Responses and Clinical Parameters for at Least 2 Years after Onset of Type 1 Diabetes" Diabetes, vol. 54, pp. 1763-1769, Jun. 2005.

Herold et al., Activation of Human T Cells by FcR Nonbinding Anti-CD3 mAb, hOKT3 gamma1 (Ala-Ala), Journal of Clinical Investigation, vol. 111, No. 3, pp. 409-418, Feb. 2003.

Herold et al., "An Anti-CD3 Antibody, Teplizumab, in Relatives at Risk for Type 1 Diabetes" The New England Journal of Medicine, vol. 381, No. 7, pp. 603-613, Aug. 15, 2019.

Herold et al., "Beta Cell Death and Dysfunction During Type 1 Diabetes Development in At-Risk Individuals" Journal of Clinical Investigation, vol. 125, No. 3, pp. 1163-1173, Mar. 2015.

Herold et al., "Teplizumab (Anti-CD3 mAb) Treatment Preserves C-Peptide Responses in Patients With New-Onset Type 1 Diabetes in a Randomized Control Trial" Diabetes, vol. 62, pp. 3766-3774, Nov. 2013.

Herold et al., "Teplizumab Treatment May Improve C-Peptide Responses in Participants with Type 1 Diabetes after the New-Onset Period: A Randomised Controlled Trial", Diabetologia, vol. 6, pp. 391-400, Feb. 2013.

Hippich et al., "Genetic Contribution to the Divergence in Type 1 Diabetes Risk Between Children From the General Population and Children from Affected Families" Diabetes, vol. 68, pp. 847-857, Apr. 2019.

Insel et al., "Staging Presymptomatic Type 1 Diabetes: A Scientific Statement of JDRF, the Endocrine Society, and the American Diabetes Association" Diabetes Care, vol. 38, pp. 1964-1974, Oct. 2015.

(56) References Cited

OTHER PUBLICATIONS

Keymeulen et al., "Insulin Needs After CD3-Antibody Therapy in New-Onset Type 1 Diabetes" Lancet Diabetes Endocrinol, vol. 7, pp. 52-64, 2019.

Kuhn et al., "Therapeutic Anti-CD3 Monoclonal Antibodies: From Bench to Bedside" Immunotherapy, vol. 8, No. 8, pp. 889-906, May 10, 2016.

Lan et al., Discrete Sequential Boundaries for Clinical Trials, Biometrika, vol. 70, No. 3, pp. 659-663, Dec. 1983.

Livingstone et al., "Estimated Life Expectancy in a Scottish Cohort with Type 1 Diabetes" JAMA, vol. 313, No. 1, pp. 37-44, Jan. 6, 2015.

Long et al., "Partial Exhaustion of CD8 T Cells and Clinical Response to Teplizumab in New-Onset Type 1 Diabetes" Science Immunology, vol. 1, No. 5, pp. 1-23, Nov. 18, 2016.

Mantel et al., "Evaluation of Suvival Data and Two New Rank Order Statistics Arising in its Consideration" Cancer Chemotherapy Reports, vol. 50, No. 3, pp. 163-170, Mar. 1966.

Menke et al., "The Prevalence of Type 1 Diabetes in the United States" Epidemiology, vol. 24, No. 5, pp. 773-774, Sep. 2013.

Miller et al., "Current State of Type 1 Diabetes Treatment in the United States" Diabetes Care, vol. 38, pp. 971-978, Jun. 2015.

Perdigoto et al., "Treatment of Type 1 Diabetes with Teplizumab: Clinical and Immunological Follow-Up after 7 Years from Diagnosis" Diabetologia, vol. 62, No. 4, pp. 655-664, Apr. 2019.

Rawshani et al., "Excess Mortality and Cardiovascular Disease in Young Adults with Type 1 Diabetes in Relation to Age at Onset: a Nationwide, Register-Based Cohort Study" Lancet vol. 392, pp. 477-486, Aug. 11, 2018.

Schoenfeld, "Sample-size Formula for the Proportional-Hazards Regression Model" Biometrics, vol. 39, No. 2, pp. 499-503, Jun. 1983.

Sherry et al., "Teplizumab for Treatment of Type 1 Diabetes (Protégé Study): 1-Year Results from a Randomised, Placebo-Controlled Trial" Lancet, vol. 378, Issue 9790, pp. 487-497, Aug. 6, 2011.

Therneau et al., "Modeling Survival Data: Extending the Cox Model". Statistics for Biology and Health. Springer, New York, NY pp. 39-77, 2000. https://doi.org/10.1007/978-1-4757-3294-8_3.

Tooley et al., "Changes in T-Cell Subsets Identify Responders to FcR Non-Binding Anti-CD3 mAb (teplizumab) in Patients with Type 1 Diabetes" European Journal of Immunology, vol. 46, pp. 230-241, Jan. 2016.

Waldron-Lynch et al., "Teplizumab Induces Human Gut-Tropic Regulatory Cells in Humanized Mice and Patients" Science Translational Medicine, vol. 4, Issue 118, pp. 1-29, Jan. 25, 2012.

Wherrett et al., "Defining Pathways for Development of Disease-Modifying Therapies in Children With Type 1 Diabetes: A Consensus Report" Diabetes Care, vol. 38, pp. 1975-1985, Oct. 2015.

Wherry, "T Cell Exhaustion" Nature Immunology, vol. 12, No. 6, pp. 492-498, Jun. 2011.

Wherry et al., "Molecular Signature of CD8+ T Cell Exhaustion During Chronic Viral Infection" Immunity, vol. 27, pp. 670-684, Oct. 2007.

Dayan et al., "Changing the Landscape for Type 1 Diabetes: The First Step to Prevention" Lancet, vol. 394, pp. 1286-1296, Oct. 5, 2019.

Skowera et al., "beta-Cell-Specific CD8 T Cell Phenotype in Type 1 Diabetes Reflects Chronic Autoantigen Exposure", Diabetes, vol. 64, No. 3, pp. 916-926, Mar. 2015.

International Search Report in International Patent Application No. PCT/US2021/037039 dated Nov. 30, 2021.

Provention Bio, Inc., "Recent-Onset Type 1 Diabetes Trial Evaluating Efficacy and Safety of Teplizumab (Protect)", Clinical Trials.gov, https://clinicaltrials.gov/ct2/show/NCT03875729, Nov. 15, 2021.

Wenzlau et al., "The Cation Efflux Transporter ZnT8 (Slc3A8) is a Major Autoantigen in Human Type 1 Diabetes" PNAS, vol. 104, No. 43, pp. 17040-17045, Oct. 23, 2007.

Teplizumab for Prevention of Type 1 Diabetes In Relatives "At-Risk"https://classic.clinicaltrials.gov/ct2/show/study/NCT01030861?term=NCT01030861&draw=2&rank=1 https://classic.clinicaltrials.gov/ct2/history/NCT01030861?V_19=View#StudyPageTop.

* cited by examiner

A. Placebo treated participants

B. Teplizumab treated participants

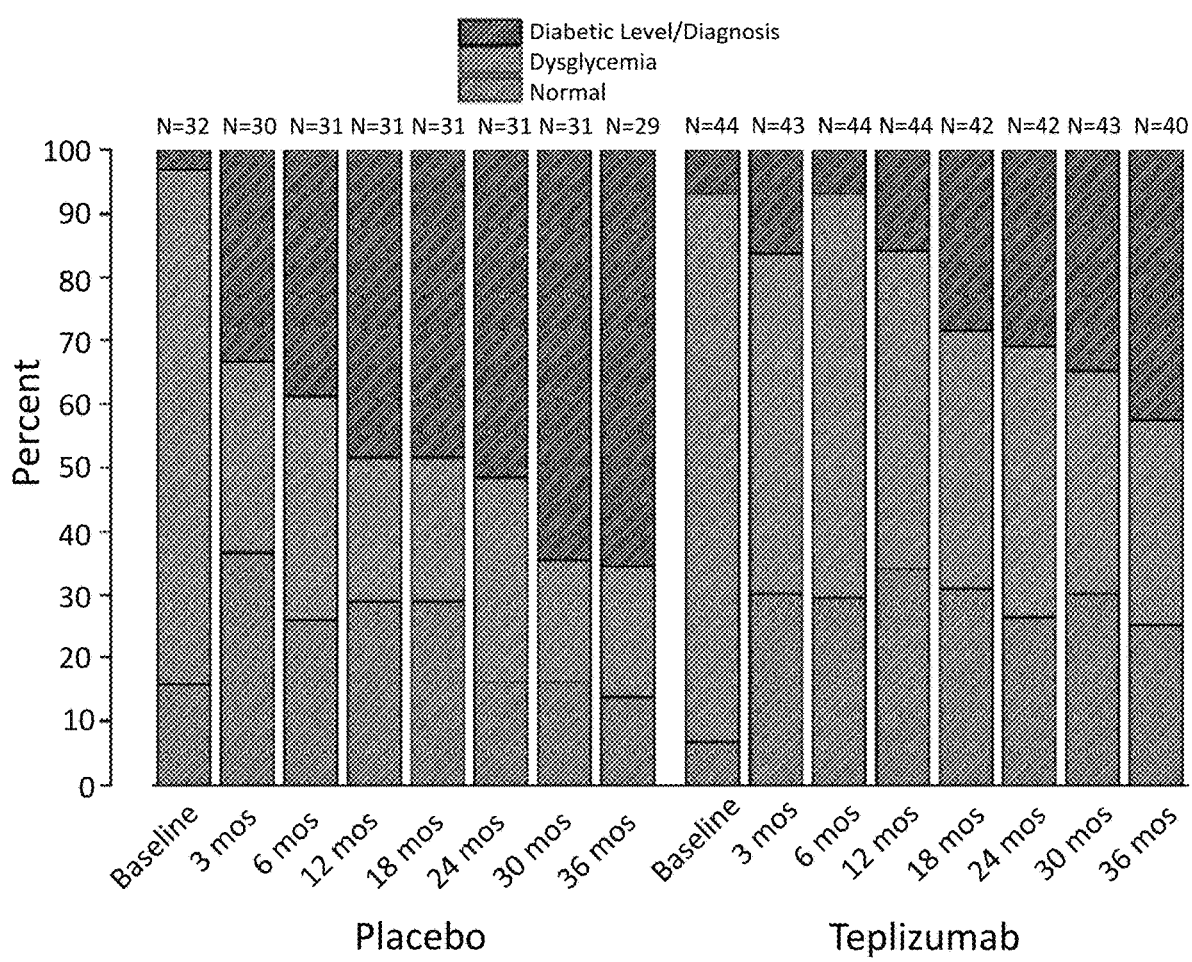

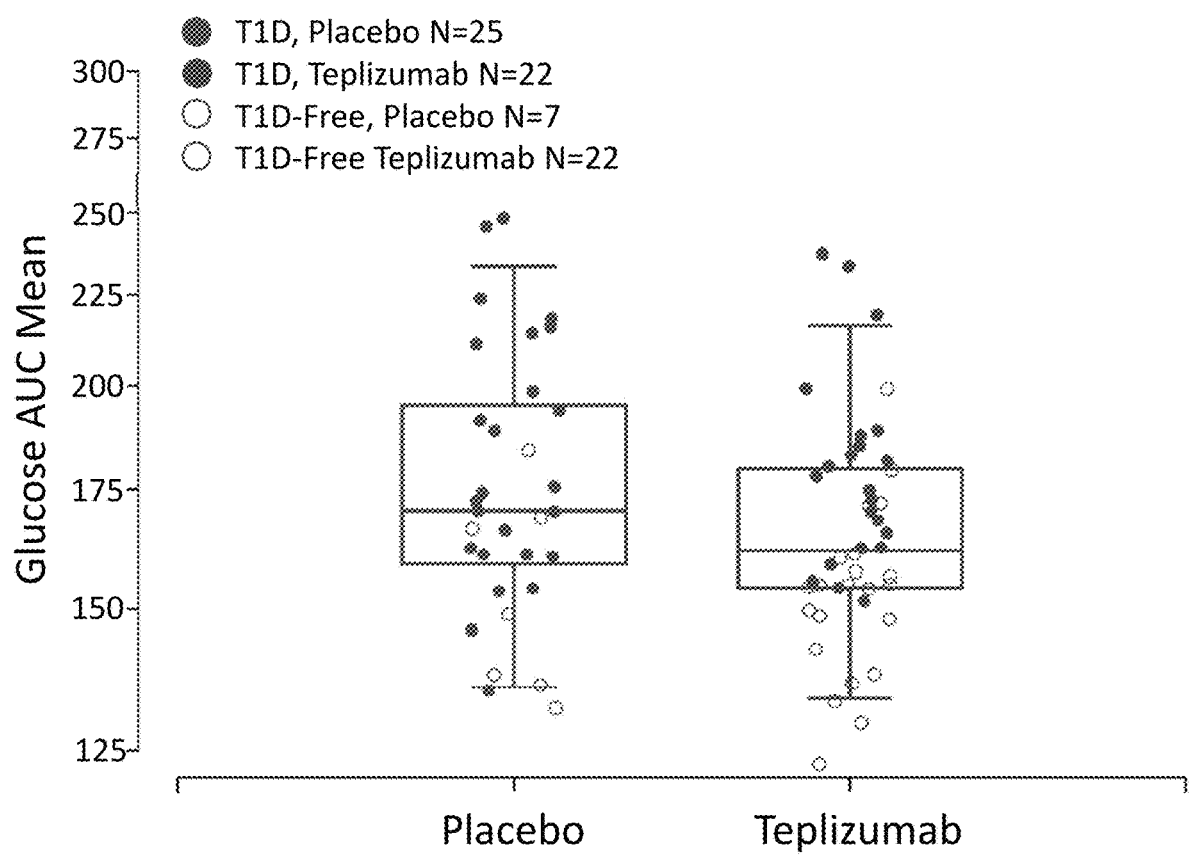

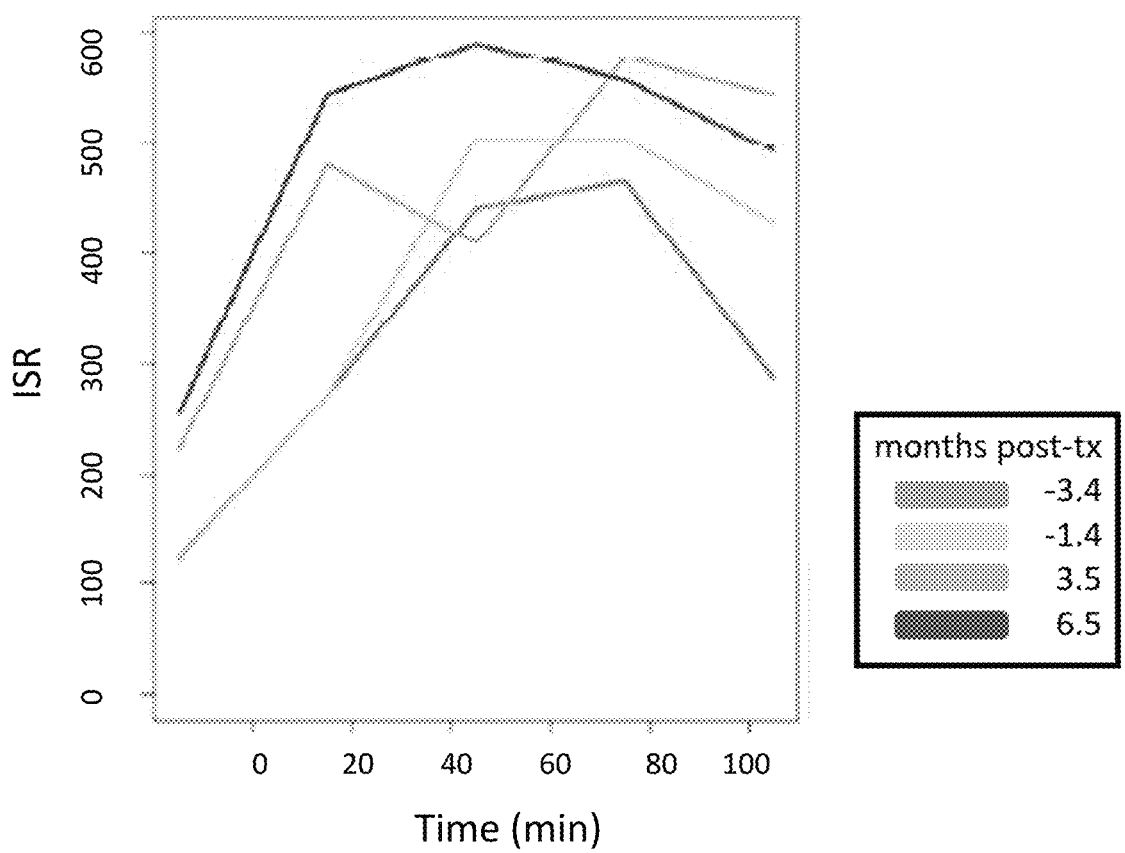

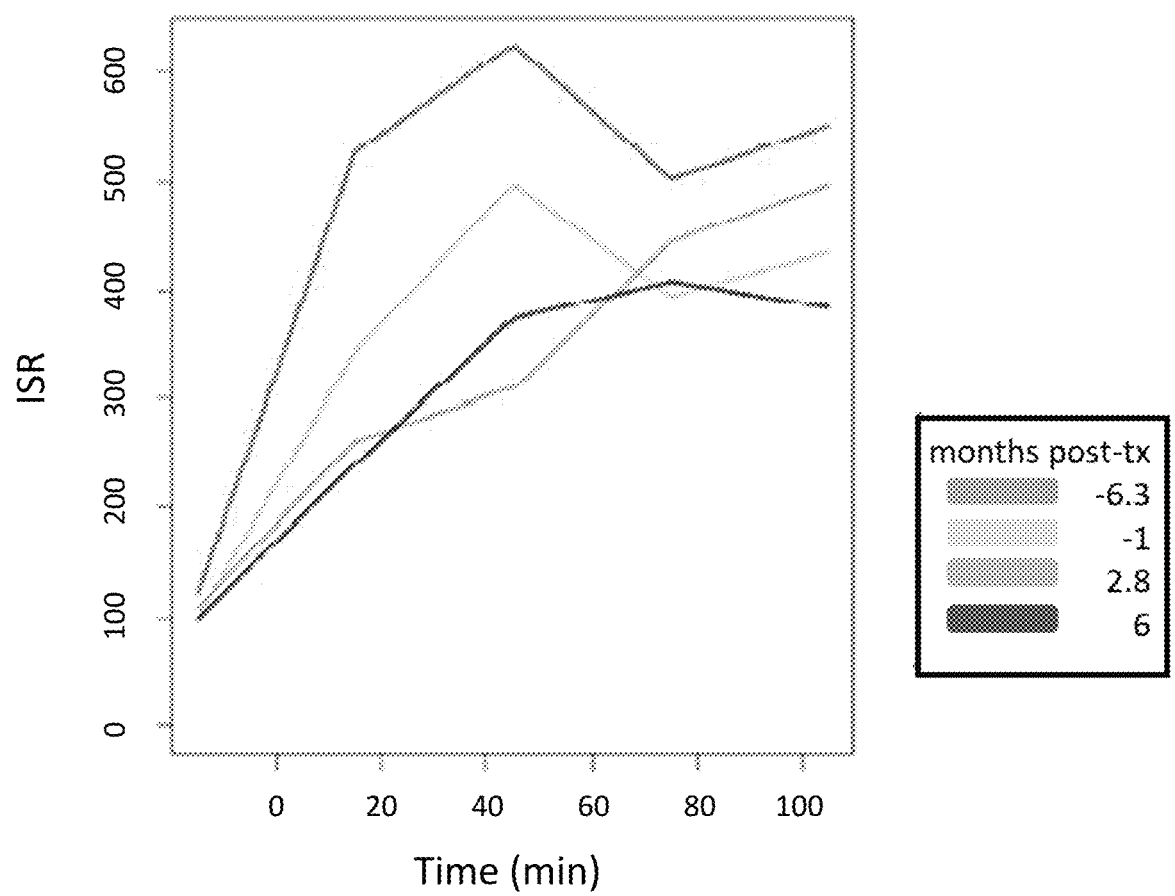

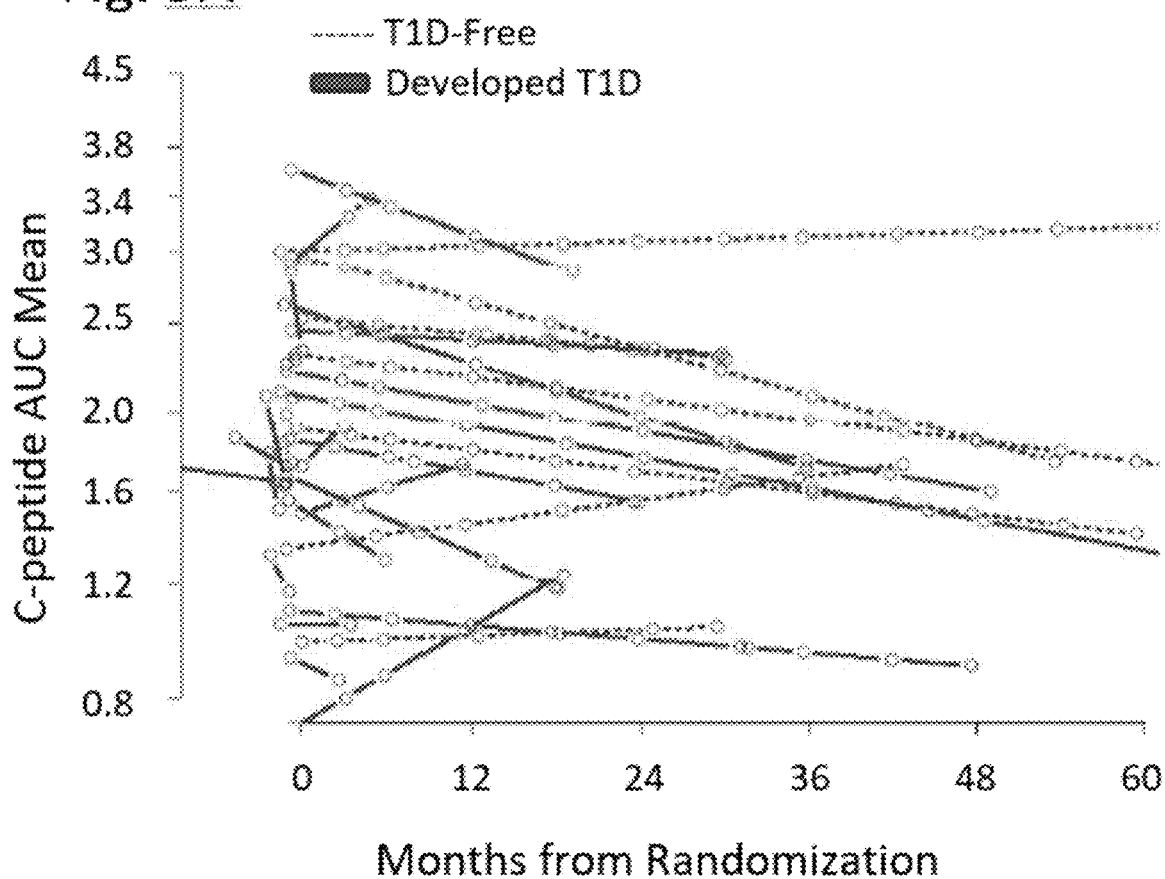

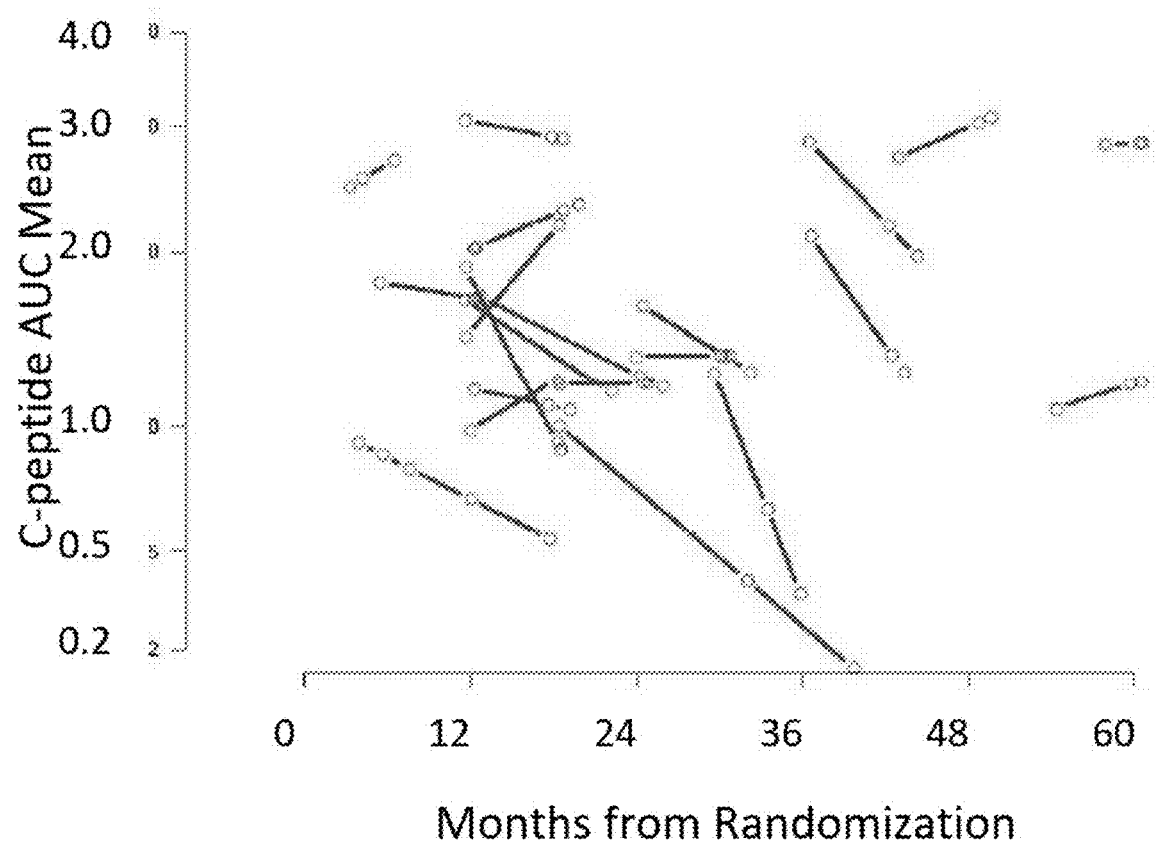

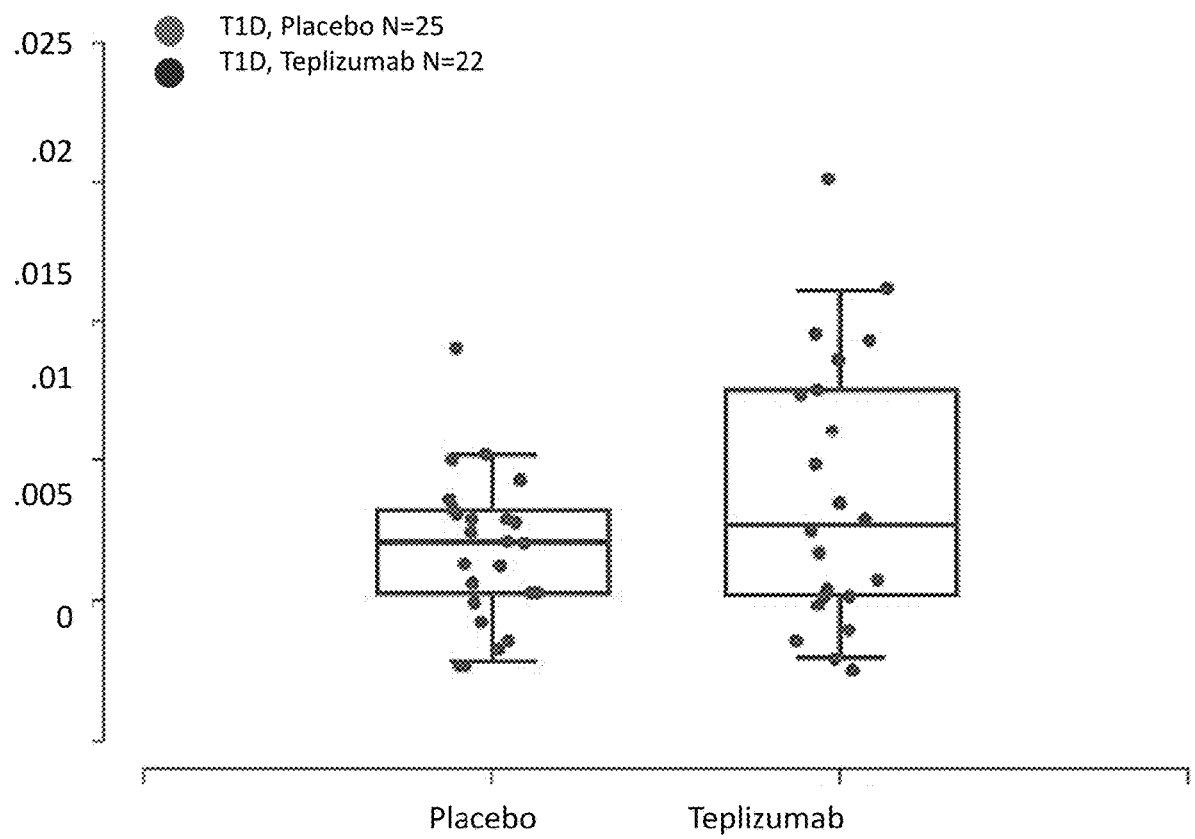

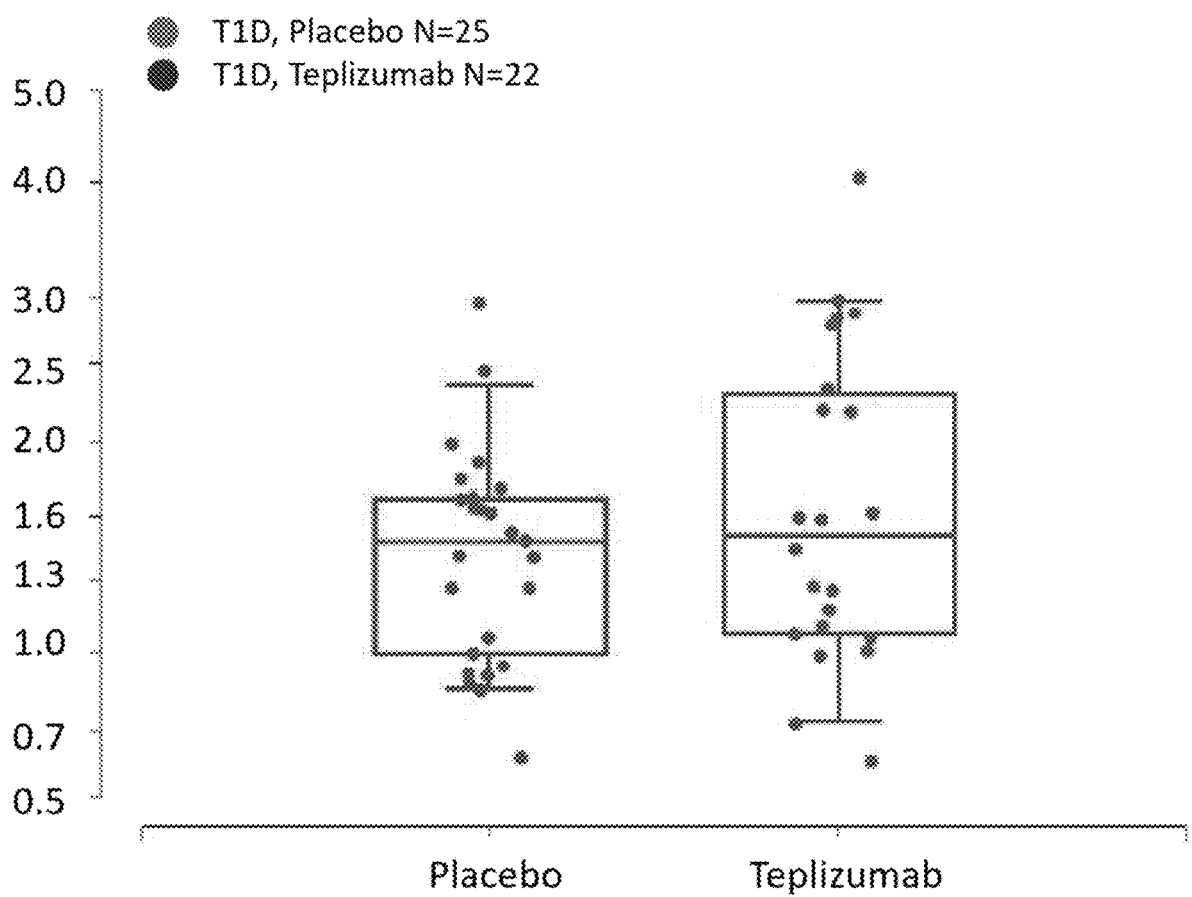

IFNγ

TNFα

Fig. 14 TIGIT+KLRG1+ CD8 T Cells from HC (and T1D Subjects)

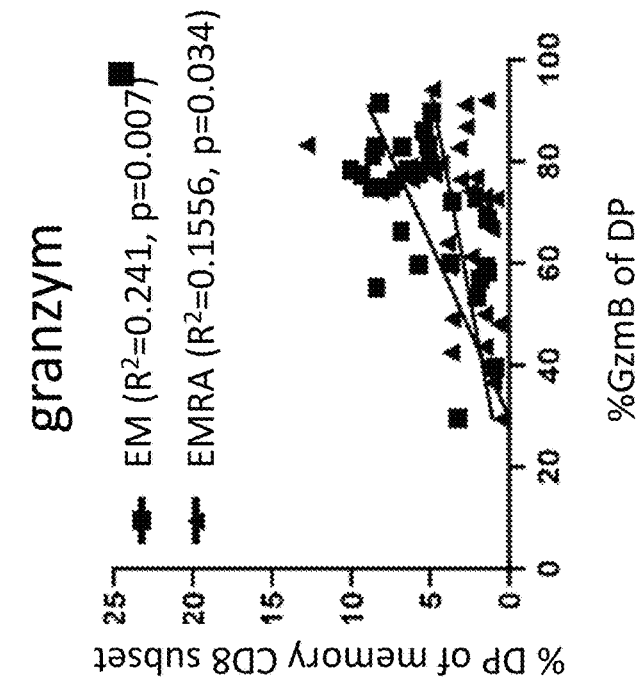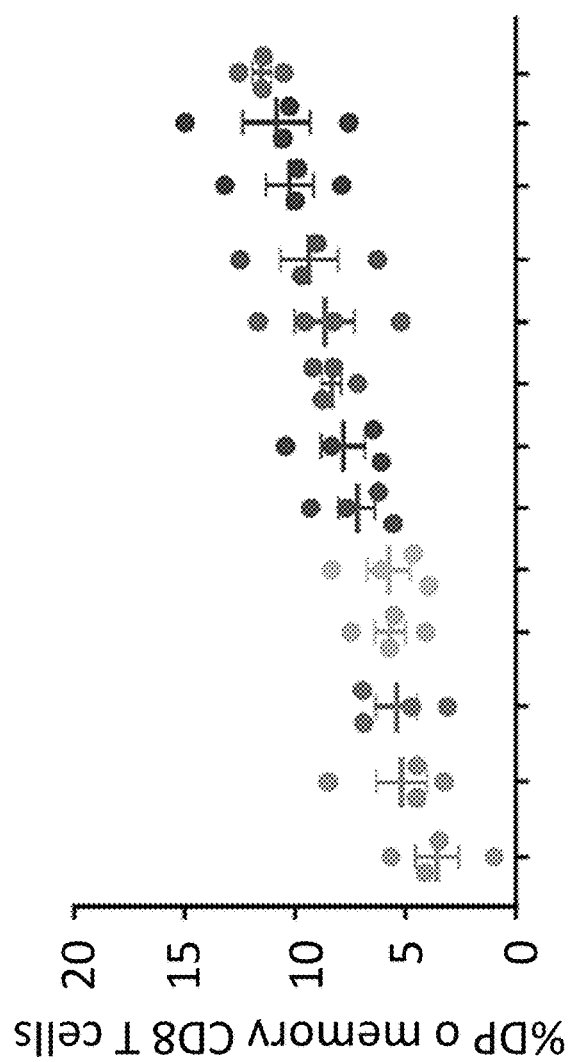
Fig. 16

Clustered CD8 T cells; all time-points and subjects in the trial

| | Placebo N=30 | Teplizumab N=41 | Adjusted for baseline value |
|---|---|---|---|
| | 3 mo – baseline Difference (SD) | 3 mo – baseline Difference (SD) | p-value |
| Mean Glucose AUC | 13.94 (43.10) | -6.30 (31.28) | 0.058 |
| Mean C-peptide AUC | -0.09 (0.36) | 0.11 (0.47) | 0.021 |
| Peak C-peptide | -0.21 (0.49) | 0.10 (0.73) | 0.022 |
| Index60 | 0.35 (0.86) | -0.20 (0.76) | 0.013 |
| DPTRS | 0.56 (1.63) | -0.22 (1.08) | 0.020 |
| (C-peptide AUC/Glucose AUC)*1000 | -0.78 (2.65) | 1.45 (2.86) | 0.001 |
| 30-0 min C-peptide | -0.09 (0.46) | 0.17 (0.44) | 0.027 |

Fig. 25

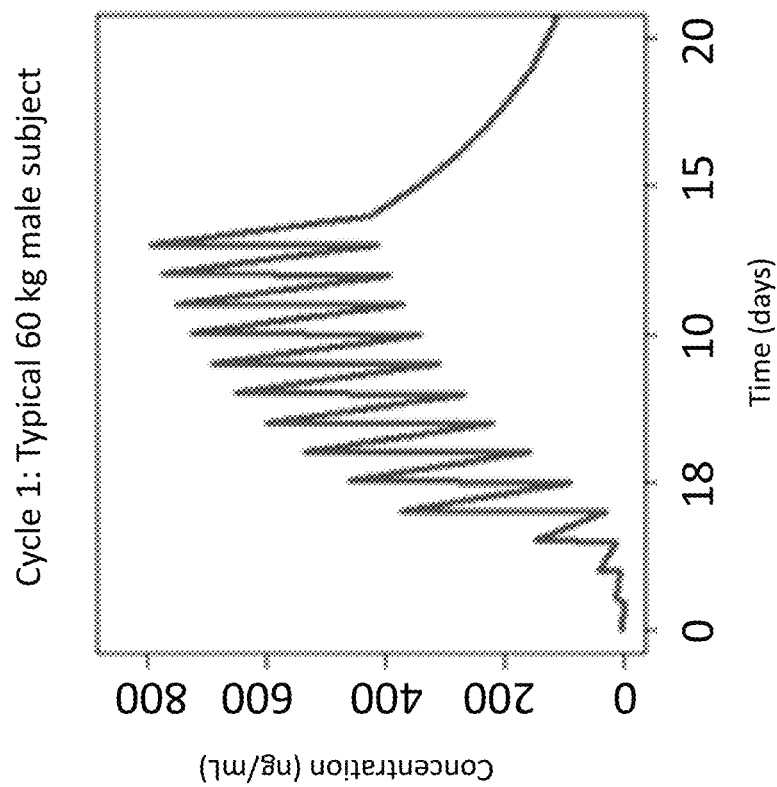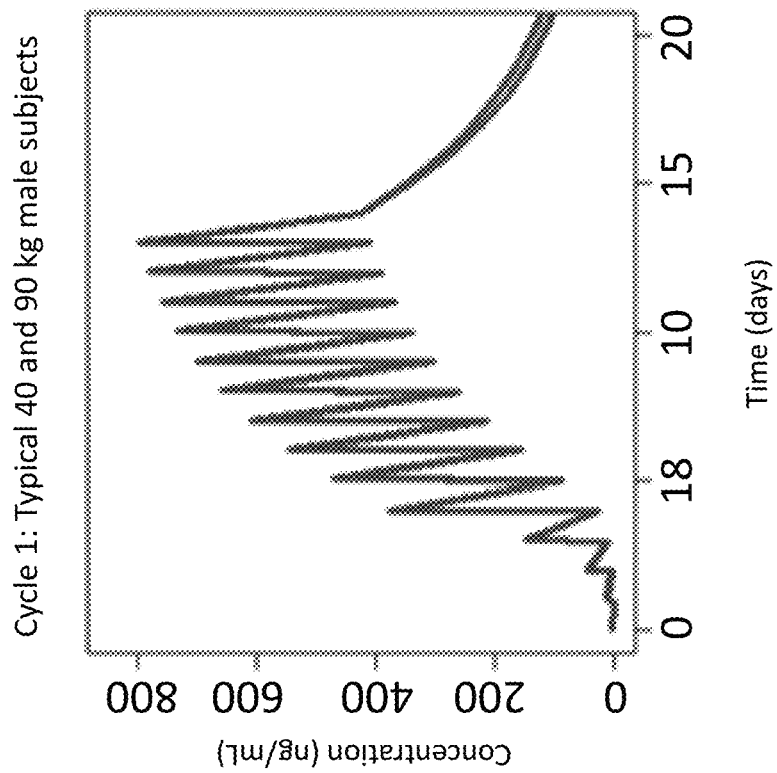
Fig. 26

METHODS AND COMPOSITIONS FOR PREVENTING TYPE 1 DIABETES

CROSS REFERENCE TO RELATED APPLICATIONS

This application claims priority to and the benefit of U.S. Provisional Patent Application No. 63/037,968 filed Jun. 11, 2020, Taiwanese Patent Application No. 110102871 filed Jan. 26, 2021, and U.S. Provisional Patent Application No. 63/192,242 filed May 24, 2021, the entire disclosure of each of which is incorporated herein by reference in its entirety.

GOVERNMENT SUPPORT

This invention was made with United States Government support under grant number R01 DK057846 awarded by National Institutes of Health, grant number UM1AI109565 awarded by National Institute of Allergy and Infectious Diseases and grant number DP3 DK104465-01 awarded by National Institute of Diabetes and Digestive and Kidney Diseases. The United States Government has certain rights in the invention.

SEQUENCE LISTING

The ASCII text file submitted herewith via EFS-Web, entitled "010903seq.txt" created on Jun. 11, 2021, having a size of 6,171 bytes, is incorporated herein by reference in its entirety.

FIELD

The present disclosure relates in general to compositions and methods of preventing or delaying the onset of clinical type 1 diabetes (T1D) in subjects at risk, and more particularly the use of anti-CD3 antibodies.

BACKGROUND

Type 1 diabetes (T1D) is caused by the autoimmune destruction of insulin producing beta cells in the islets of Langerhans leading to dependence on exogenous insulin injections for survival. Approximately 1.6 million Americans have Type 1 diabetes, and after asthma, it remains one of the most common diseases of childhood. Despite improvements in care, most affected individuals with T1D are not able to consistently achieve desired glycemic targets. For individuals with type 1 diabetes, there are persisting concerns for increased risk of both morbidity and mortality. Two recent studies noted loss of 17.7 life-years for children diagnosed before age 10, and 11 and 13 life-years lost for adult-diagnosed Scottish men and women respectively.

In genetically susceptible individuals, T1D progresses through asymptomatic stages prior to overt hyperglycemia, characterized first by the appearance of autoantibodies (Stage 1) and then dysglycemia (Stage 2). In Stage 2, metabolic responses to a glucose load are impaired but other metabolic indices, for example glycosylated hemoglobin, are normal and insulin treatment is not needed. These immunologic and metabolic features identify individuals who are at high-risk for development of clinical disease with overt hyperglycemia and requirement for insulin treatment (Stage 3). Several immune interventions have been shown to delay decline in beta cell function when studied in recent-onset clinical T1D. One promising therapy is the FcR nonbinding anti-CD3 monoclonal antibody teplizumab, as several studies have shown that short-term treatment reduces loss of β cell function durably, with an observable effect seen as long as 7 years after diagnosis and treatment. The drug modifies the function of CD8+ T lymphocytes, which are thought to be important effector cells that cause beta cell killing.

To date, no intervention initiated before the clinical diagnosis (i.e., at Stage 1 or 2) has altered progression to clinical, Stage 3 T1D. Thus, a need exists for a treatment that would prevent or delay the onset of clinical T1D in high-risk individuals.

SUMMARY

A method of preventing or delaying the onset of clinical type 1 diabetes (T1D), comprising:
providing a non-diabetic subject who is at risk for T1D;
administering a prophylactically effective amount of an anti-CD3 antibody to the non-diabetic subject; and
determining, prior to or after the administering step, that the non-diabetic subject has more than about 5% to more than about 10% TIGIT+KLRG1+CD8+ T-cells in all CD3+ T cells, which is indicative of successful prevention or delay of the onset of clinical T1D.

In some embodiments, the non-diabetic subject is a relative of a patient with T1D.

In some embodiments, the method further includes determining that the non-diabetic subject (1) is substantially free of antibodies against zinc transporter 8 (ZnT8), (2) is HLA-DR4+, and/or (3) is not HLA-DR3+.

In some embodiments, the non-diabetic subject has 2 or more diabetes-related autoantibodies selected from islet cell antibodies (ICA), insulin autoantibodies (IAA), and antibodies to glutamic acid decarboxylase (GAD), tyrosine phosphatase (IA-2/ICA512) or ZnT8.

In some embodiments, the non-diabetic subject has abnormal glucose tolerance on oral glucose tolerance test (OGTT). In some embodiments, the abnormal glucose tolerance on OGTT is a fasting glucose level of 110-125 mg/dL, or 2 hour plasma of ≥140 and <200 mg/dL, or an intervening glucose value at 30, 60, or 90 minutes on OGTT>200 mg/dL.

In some embodiments, the non-diabetic subject does not have antibodies against ZnT8.

In some embodiments, the non-diabetic subject is HLA-DR4+ and is not HLA-DR3+.

In some embodiments, the anti-CD3 antibody is selected from teplizumab, otelixizumab or foralumab. In some embodiments, the prophylactically effective amount of the antibody comprises a 10 to 14 day course of subcutaneous (SC) injection or intravenous (IV) infusion or oral administration of the anti-CD3 antibody at 10-1000 micrograms/meter squared ($\mu g/m^2$), preferably a 14-day course IV infusion at 51 $\mu g/m^2$, 103 $\mu g/m^2$, 207 $\mu g/m^2$, and 413 $\mu g/m^2$, on days 0-3, respectively, and one dose of 826 $\mu g/m^2$ on each of days 4-13.

In some embodiments, the prophylactically effective amount delays median time to clinical diagnosis of T1D by at least 50%, at least 80%, or at least 90%, or at least 12 months, at least 18 months, at least 24 months, at least 36 months, at least 48 months, or at least 60 months.

In some embodiments, the determining of TIGIT+KLRG1+CD8+ T-cells is by flow cytometry.

In some embodiments, the method further includes determining a decrease in a percentage of CD8+ T cells expressing proliferation markers Ki67 and/or CD57.

A method of prognosing responsiveness of an anti-CD3 antibody in preventing or delaying the onset of type 1 diabetes (T1D), comprising:

providing a non-diabetic subject who is at risk for T1D;
administering a prophylactically effective amount of an anti-CD3 antibody to the non-diabetic subject; and
determining C-peptide area under the curve (AUC): glucose AUC ratio, wherein an increase in said ratio indicates responsiveness to the anti-CD3 antibody and/or non-progression to clinical T1D.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B show that improved glycemia in teplizumab treated participants is associated with maintenance of dysglycemic status. FIG. 3A shows OGTT classifications for participants in each group over 36 months of follow-up. The data are shown to 36 months because of loss of placebo treated participants because of the clinical diagnosis of T1D (for individual participants see FIGS. 2A-2B). FIG. 3B shows a boxplot displaying median and interquartile ranges for on-study OGTT glucose AUC mean for participants from placebo and teplizumab treated groups. ANCOVA model incorporating baseline value, age, and treatment group showed that treatment group had a significant effect to decrease average on-study glucose AUC (ANCOVA teplizumab effect: 92.8%, p=0.02).

FIG. 5 shows a boxplot displaying median and interquartile ranges for average on-study OGTT C-peptide AUC mean for participants from placebo and teplizumab treated groups. An ANCOVA model including baseline C-peptide AUC and age showed that treatment was associated with higher average on-study C-peptide AUC (p=0.009).

FIG. 6 shows a scatterplot of age vs. on-study C-peptide AUC (r=0.44, p=0.0001).

FIGS. 8A-8G show insulin secretion following treatment with teplizumab or placebo. Estimated slopes for the insulin secreted (pmol) secreted during the total (FIG. 8A), first hour (FIG. 8B), and second hour (FIG. 8C) of the OGTT at the visits before enrollment and over the first 6 months following study drug treatment. Median values (and 95% CIs in shaded colors) are shown. Refer to Table 5 for statistical analyses. FIGS. 8D and 8E show representative insulin secretion rates during serial OGTTs for 2 teplizumab participants who were not diagnosed with T1D (age 11 and 12 years) and (FIG. 8F and FIG. 8G) two placebo treated individuals (both age 13 years) who were diagnosed with T1D. The color lines indicate the time of the visits in relationship to study drug administration.

FIGS. 9A-9E show that teplizumab preserves C-peptide over the course of the study until the period surrounding diagnosis. For all panels, data from teplizumab-treated participants are shown in blue, and placebo-treated participants are shown in maroon. FIG. 9A and FIG. 9B show regression lines for C-peptide AUC values over the study period of OGTT monitoring from baseline study visit until diagnosis (teplizumab n=44, placebo n=32). FIG. 9C and FIG. 9D show regression lines for C-peptide AUC values over 6-month period before diabetes diagnosis (placebo n=23, teplizumab n=22). FIG. 9E shows slopes of C-peptide AUC for 6-month period before diagnosis in those that developed T1D, and the last 6 months of study in individuals remaining T1D-free.

FIG. 10A and FIG. 10B show that C-peptide values are similar between treatment groups at the time of diagnosis. FIG. 10A shows C-peptide AUC/Glucose AUC at the time of clinical diagnosis of T1D. FIG. 10B shows C-peptide AUC at the time of clinical diagnosis of T1D. Values were obtained from the first of two consecutive diagnostic OGTTs consistent with a classification of T1D.

FIG. 11A shows the changes in TIGIT+KLRG1+CD45RO+ CD8+ T cells between baseline and 3 months and the change in the C-peptide AUC between the baseline and 6 months are shown. There was a significant correlation between the changes in this cell subset and C peptide in the teplizumab (Pearson r=0.44, p=0.014, n=31) but not the placebo treated (r=0.28, p=0.25, n=18) participants. FIG. 11B and FIG. 11C show the frequency of double positive (DP, i.e. TIGIT+ KLRG1+) CD8+ memory cells that produce IFNγ or TNFα are shown for the placebo treated (red dot, n=16) and drug treated (blue dot, n=24) participants at baseline and month 3. The frequency of the IFNγ and TNFα producing cells were reduced in the teplizumab treated participants (paired T-test, ***p<0.0001).

FIG. 15 and FIG. 16 show total TIGIT+KLRG1+CD8 T cells are heterogeneous.

FIG. 25 shows 3-month change in ratio of C-peptide AUC/Glucose AUC shows most significant differences compared to other metabolic measures.

FIG. 26: Predicted Mean Teplizumab Serum Concentration Versus Time Profile Following 14-Day Regimen Across Different Body Weights.

DETAILED DESCRIPTION

Figure 1A:
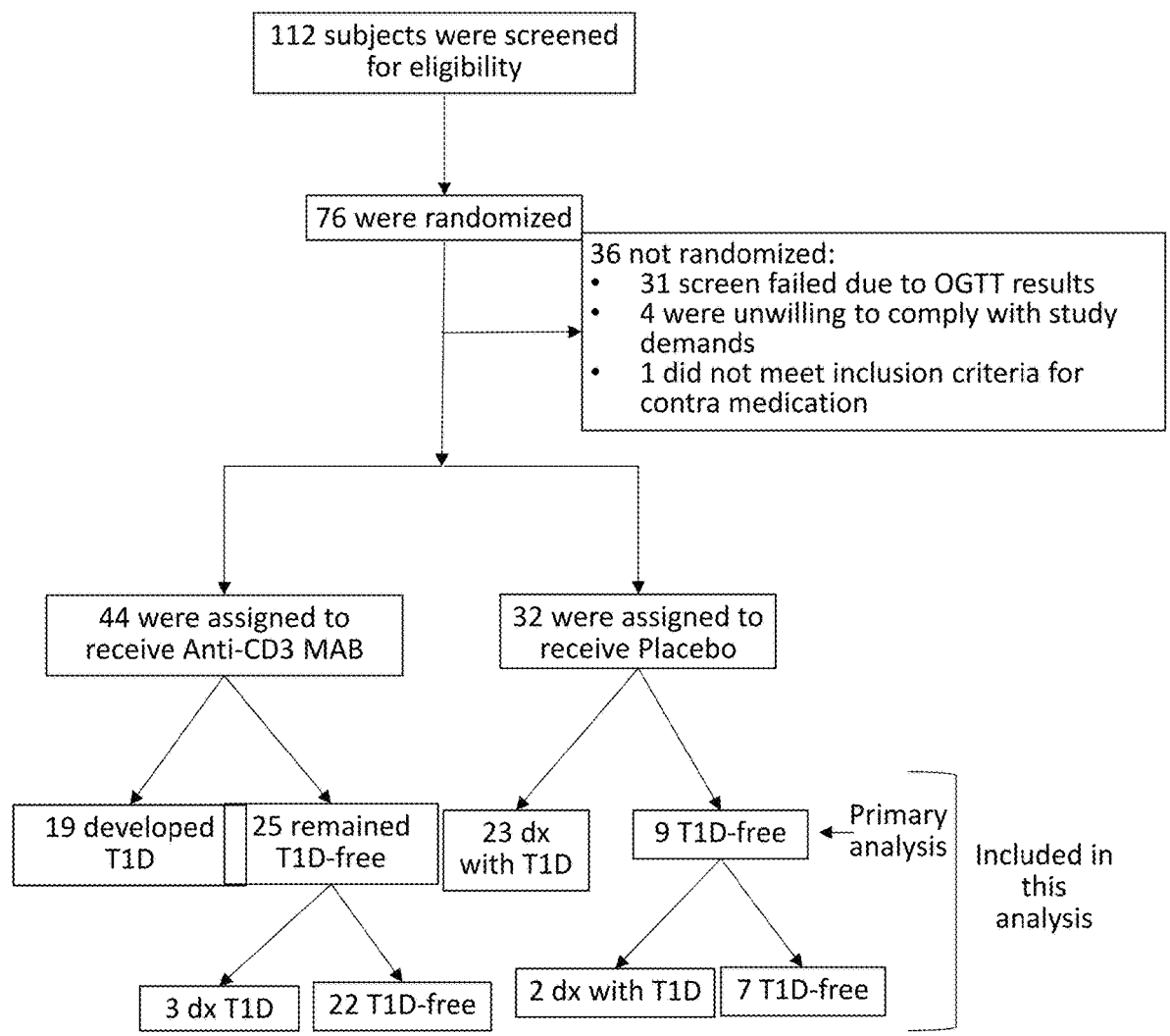
FIG. 1A shows a consort diagram of at-risk individuals enrolled into the teplizumab prevention study.

Provided herein, in some embodiments, is a method of preventing or delaying the onset of clinical type 1 diabetes (T1D), comprising: providing a non-diabetic subject who is at risk for T1D; administering a prophylactically effective amount of an anti-CD3 antibody to the non-diabetic subject; and determining, prior to or after the administering step, that the non-diabetic subject has more than about 5% to more than about 10% TIGIT+KLRG1+CD8+ T-cells in all CD3+ T cells, which is indicative of successful prevention or delay of the onset of clinical T1D.

In some embodiments, a method of prognosing responsiveness of an anti-CD3 antibody, e.g., teplizumab, in preventing or delaying the onset of T1D is provided. The method can include: providing anon-diabetic subject who is at risk for T1D; administering a prophylactically effective amount of the anti-CD3 antibody, e.g., teplizumab, to the non-diabetic subject; and determining C-peptide area under the curve (AUC): glucose AUC ratio, wherein an increase in said ratio indicates responsiveness to the anti-CD3 antibody.

Definitions

Certain terms are defined herein below. Additional definitions are provided throughout the application.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

As used herein, the term "prophylactic agent" refer to CD3 binding molecules such as teplizumab which can be used in the prevention, treatment, management or amelioration of one or more symptoms of T1D.

As used herein, the term "onset" of disease with reference to Type-1 diabetes refers to a patient meeting the criteria established for diagnosis of Type-1 diabetes by the American Diabetes Association (see, Mayfield et al., 2006, Am. Fam. Physician 58:1355-1362).

As used herein, the terms "prevent", "preventing" and "prevention" refer to the prevention of the onset of one or more symptoms of T1D in a subject resulting from the administration of a prophylactic or therapeutic agent.

As used herein, a "protocol" includes dosing schedules and dosing regimens. The protocols herein are methods of use and include prophylactic and therapeutic protocols. A "dosing regimen" or "course of treatment" may include administration of several doses of a therapeutic or prophylactic agent over 1 to 20 days.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey or a human), and more preferably a human.

As used herein, the term "prophylactically effective amount" refers to that amount of teplizumab sufficient to result in the delay or prevention of the development, recurrence or onset of one or more symptoms of T1D. In some embodiments, a prophylactically effective amount preferably refers to the amount of teplizumab that delays a subject's onset of T1D by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%.

Various aspects of the disclosure are described in further detail below. Additional definitions are set out throughout the specification.

Anti-CD3 Antibodies and Pharmaceutical Compositions

The terms "anti-CD3 antibody" and "an antibody that binds to CD3" refer to an antibody or antibody fragment that is capable of binding cluster of differentiation 3 (CD) with sufficient affinity such that the antibody is useful as a prophylactic, diagnostic and/or therapeutic agent in targeting CD3. In some embodiments, the extent of binding of an anti-CD3 antibody to an unrelated, non-CD3 protein is less than about 10% of the binding of the antibody to CD3 as measured, e.g., by a radioimmunoassay (RIA). In some embodiments, an antibody that binds to CD3 has a dissociation constant (Kd) of <1 µM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). In some embodiments, an anti-CD3 antibody binds to an epitope of CD3 that is conserved among CD3 from different species.

In some embodiments, the anti-CD3 antibody can be ChAglyCD3 (otelixizumab). Otelixizumab is a humanized Fc nonbinding anti-CD3, which was evaluated initially in phase 2 studies by the Belgian Diabetes Registry (BDR) and then developed by Tolerx, which then partnered with GSK to conduct the phase 3 DEFEND new onset T1D trials (NCT00678886, NCT01123083, NCT00763451). Otelixizumab is administered IV with infusions over 8 days. See, e.g., Wiczling et al., J. Clin. Pharmacol. 50 (5) (May 2010) 494-506; Keymeulen et al., N Engl J Med. 2005; 352:2598-608; Keymeulen et al., Diabetologia. 2010; 53:614-23; Hagopian et al., Diabetes. 2013; 62:3901-8; Aronson et al., Diabetes Care. 2014; 37:2746-54; Ambery et al., Diabet Med. 2014; 31:399-402; Bolt et al., Eur. J. Immunol. 1YY3. 23: 403-411; Vlasakakis et al., Br J Clin Pharmacol (2019) 85 704-714; Guglielmi et al, Expert Opinion on Biological Therapy, 16:6, 841-846; Keymeulen et al., N Engl J Med 2005; 352:2598-608; Keymeulen et al., BLOOD 2010, VOL 115, No. 6; Sprangers et al., Immunotherapy (2011) 3(11), 1303-1316; Daifotis et al., Clinical Immunology (2013) 149, 268-278; all incorporated herein by reference.

In some embodiments, the anti-CD3 antibody can be visilizumab (also called HuM291; Nuvion). Visilizumab is a humanized anti-CD3 monoclonal antibody characterized by a mutated IgG2 isotype, lack of binding to Fcγ receptors, and the ability to induce apoptosis selectively in activated T cells. It was evaluated in patients in graft-versus-host disease (NCT00720629; NCT00032279) and in ulcerative colitis (NCT00267306) and Crohn's Disease (NCT00267709). See, e.g., Sandborn et al., Gut 59 (11) (November 2010) 1485-1492, incorporated herein by reference.

In some embodiments, the anti-CD3 antibody can be foralumab, a fully human anti-CD3 monoclonal antibody being developed by Tiziana Life Sciences, PLC in NASH and T2D (NCT03291249). See, e.g., Ogura et al., Clin Immunol. 2017; 183:240-246; Ishikawa et Diabetes. 2007; 56(8):2103-9; Wu et al., J Immunol. 2010; 185(6):3401-7; all incorporated herein by reference.

In some embodiments, the anti-CD3 antibody can be teplizumab. Teplizumab, also known as hOKT3y1(Ala-Ala) (containing an alanine at positions 234 and 235) is an anti-CD3 antibody that had been engineered to alter the function of the T lymphocytes that mediate the destruction of the insulin-producing beta cells of the islets of the pancreas. Teplizumab binds to an epitope of the CD3E chain expressed on mature T cells and by doing so changes their function. Sequences and compositions of teplizumab are disclosed in U.S. Pat. Nos. 6,491,916; 8,663,634; and 9,056,906, each incorporated herein by reference in its entirety.

The full sequences of light and heavy chains are set forth below. Bolded portions are the complementarity determining regions.

```
Teplizumab Light Chain (SEQ ID NO: 1):
DIQMTQSPSSLSASVGDRVTITCSASSSVSYMNWY

QQTPGKAPKRWIYDTSKLASGVPSRFSGSGSGTDY

TFTISSLQPEDIATYYCQQWSSNPFTFGQGTKLQI

TRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC
Teplizumab Heavy Chain (SEQ ID NO: 2):
QVQLVQSGGGVVQPGRSLRLSCKASGYTFTRYTMH

WVRQAPGKGLEWIGYINPSRGYTNYNQKVKDRFTI

SRDNSKNTAFLQMDSLRPEDTGVYFCARYYDDHYC

LDYVVGQGTPVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALPAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGK
```

In some embodiments, provided herein, is a pharmaceutical composition. Such compositions comprise a prophylactically effective amount of an anti-CD3 antibody, and a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like (See, for example, Handbook of Pharmaceutical Excipients, Arthur H. Kibbe (ed., 2000, which is incorporated by reference herein in its entirety), Am. Pharmaceutical Association, Washington, D.C.

The composition, if desired, can also contain minor amounts of wetting or emulsifying agents, or pH buffering agents. These compositions can take the form of solutions, suspensions, emulsion, tablets, pills, capsules, powders, sustained release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of a prophylactic or therapeutic agent preferably in purified form, together with a suitable amount of carrier so as to provide the form for proper administration to the patient. The formulation should suit the mode of administration. In some embodiments, the pharmaceutical compositions are sterile and in suitable form for administration to a subject, preferably an animal subject, more preferably a mammalian subject, and most preferably a human subject.

In some embodiments, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering the anti-CD3 antibody, care must be taken to use materials to which the anti-CD3 antibody does not absorb.

In some embodiments, the composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In some embodiments, the composition can be delivered in a controlled release or sustained release system. In some embodiments, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In some embodiments, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In some embodiments, the polymer used in a sustained release formulation is inert, free of leachable impurities, stable on storage, sterile, and biodegradable. In some embodiments, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention or fragments thereof. See, e.g., U.S. Pat. No. 4,526,938; PCT Publication No. WO 91/05548; PCT Publication No. WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760, each of which is incorporated herein by reference in its entirety.

A pharmaceutical composition can be formulated to be compatible with its intended route of administration. Examples of routes of administration include, but are not limited to, parenteral, e.g., intravenous, intradermal, subcutaneous, oral, intranasal (e.g., inhalation), transdermal (topical), transmucosal, and rectal administration. In some embodiments, the composition is formulated in accordance with routine procedures as a pharmaceutical composition adapted for intravenous, subcutaneous, intramuscular, oral, intranasal or topical administration to human beings. In some embodiments, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In some embodiments, the disclosure provides dosage forms that permit administration of the anti-CD3 antibody continuously over a period of hours or days (e.g., associated with a pump or other device for such delivery), for example, over a period of 1 hour, 2 hours, 3 hours, 4 hours, 6 hours, 8 hours, 10 hours, 12 hours, 16 hours, 20 hours, 24 hours, 30 hours, 36 hours, 4 days, 5 days, 7 days, 10 days or 14 days. In some embodiments, the invention provides dosage forms that permit administration of a continuously increasing dose, for example, increasing from 51 ug/m$^2$/day to 826 ug/m$^2$/day over a period of 24 hours, 30 hours, 36 hours, 4 days, 5 days, 7 days, 10 days or 14 days.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of the compositions disclosed herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In particular, the disclosure provides that the anti-CD3 antibodies, or pharmaceutical compositions thereof, can be packaged in a hermetically sealed container such as an ampoule or sachette indicating the quantity of the agent. In some embodiments, the anti-CD3 antibody, or pharmaceutical compositions thereof is supplied as a dry sterilized lyophilized powder or water free concentrate in a hermetically sealed container and can be reconstituted, e.g., with water or saline to the appropriate concentration for administration to a subject. Preferably, the anti-CD3 antibody, or pharmaceutical compositions thereof is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic agents, or pharmaceutical compositions herein should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In some embodiments, the pharmaceutical composition is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

In some embodiments, the disclosure provides that the composition of the invention is packaged in a hermetically sealed container such as an ampoule or sachette indicating the quantity of the anti-CD3 antibody.

The compositions may, if desired, be presented in a pack or dispenser device that may contain one or more unit dosage forms containing the active ingredient. The pack may, for example, comprise metal or plastic foil, such as a blister pack.

The amount of the composition of the invention which will be effective in the prevention or amelioration of one or more symptoms associated with T1D can be determined by standard clinical techniques. The precise dose to be employed in the formulation will also depend on the route of administration and the seriousness of the condition, and should be decided according to the judgment of the practitioner and each patient's circumstances. Effective doses may be extrapolated from dose-response curves derived from in vitro or animal model test systems.

Methods and Use

In some embodiments, the present disclosure encompasses administration of anti-human CD3 antibodies such as teplizumab to individuals predisposed to develop type 1 diabetes or with pre-clinical stages of type 1 diabetes, but who do not meet the diagnosis criteria as established by the American Diabetes Association or the Immunology of Diabetes Society to prevent or delay the onset of type 1 diabetes and/or to prevent or delay the need for administration of insulin to such patients. In some embodiments, high-risk factors for identification of predisposed subjects include having first or second degree relatives with diagnosed type-1 diabetes, an impaired fasting glucose level (e.g., at least one determination of a glucose level of 100-125 mg/dl after fasting (8 hours with no food)), an impaired glucose tolerance in response to a 75 g OGTT (e.g., at least one determination of a 2-hr glucose level of 140-199 mg/dl in response to a 75 g OGTT), an HLA type of DR3, DR4 or DR7 in a Caucasian, an HLA type of DR3 or DR4 in a person of African descent, an HLA type of DR3, DR4 or DR9 in a person of Japanese descent, exposure to viruses (e.g., coxsackie B virus, enteroviruses, adenoviruses, rubella, cytomegalovirus, Epstein-Barr virus), a positive diagnosis according to art accepted criteria of at least one other autoimmune disorder (e.g., thyroid disease, celiac disease), and/or the detection of autoantibodies, particularly ICAs and type 1 diabetes-associated autoantibodies, in the serum or other tissues. In some embodiments, the subject identified as predisposed to developing type 1 diabetes has at least one of the risk factors described herein and/or as known in the art. The present disclosure also encompasses identification of subjects predisposed to development of type 1 diabetes, wherein said subject presents a combination of two or more, three or more, four or more, or more than five of the risk factors disclosed herein or known in the art.

Serum autoantibodies associated with type 1 diabetes or with a predisposition for the development of type 1 diabetes are islet-cell autoantibodies (e.g., anti-ICA512 autoantibodies), glutamic acid decarbamylase autoantibodies (e.g., anti-GAD65 autoantibodies), IA2 antibodies, ZnT8 antibodies and/or anti-insulin autoantibodies. Accordingly, in a specific example in accordance with this embodiment, the invention encompasses the treatment of an individual with detectable autoantibodies associated with a predisposition to the development of type 1 diabetes or associated with early stage type 1 diabetes (e.g., anti-IA2, anti-ICA512, anti-GAD or anti-insulin autoantibodies), wherein said individual has not been diagnosed with type 1 diabetes and/or is a first or second degree relative of a type-1 diabetic. In some embodiments, the presence of the autoantibodies is detected by ELISA, electrochemoluminescence (ECL), radioassay (see, e.g., Yu et al., 1996, J. Clin. Endocrinol. Metab. 81:4264-4267), agglutination PCR (Tsai et al, *ACS Central Science* 2016 2 (3), 139-147) or by any other method for immunospecific detection of antibodies described herein or as known to one of ordinary skill in the art.

β-cell function prior to, during, and after therapy may be assessed by methods described herein or by any method known to one of ordinary skill in the art. For example, the Diabetes Control and Complications Trial (DCCT) research group has established the monitoring of percentage glycosylated hemoglobin (HA1 and HA1c) as the standard for evaluation of blood glucose control (DCCT, 1993, N. Engl. J. Med. 329:977-986). Alternatively, characterization of daily insulin needs, C-peptide levels/response, hypoglycemic episodes, and/or FPIR may be used as markers of β-cell function or to establish a therapeutic index (See Keymeulen et al., 2005, N. Engl. J. Med. 352:2598-2608; Herold et al., 2005, Diabetes 54:1763-1769; U.S. Pat. Appl. Pub. No. 2004/0038867 A1; and Greenbaum et al., 2001, Diabetes 50:470-476, respectively). For example, FPIR is calculated as the sum of insulin values at 1 and 3 minutes post IGTT, which are performed according to Islet Cell Antibody Register User's Study protocols (see, e.g., Bingley et al., 1996, Diabetes 45:1720-1728 and McCulloch et al., 1993, Diabetes Care 16:911-915).

In some embodiments, the individuals predisposed to develop T1D can be a non-diabetic subject who is a relative of a patient with T1D. In some embodiments, the non-diabetic subject has 2 or more diabetes-related autoantibodies selected from islet cell antibodies (ICA), insulin autoantibodies (IAA), and antibodies to glutamic acid decarboxylase (GAD), tyrosine phosphatase (IA-2/ICA512) or ZnT8.

In some embodiments, the non-diabetic subject has abnormal glucose tolerance on oral glucose tolerance test (OGTT). Abnormal glucose tolerance on OGTT is defined as a fasting glucose level of 110-125 mg/dL, or 2 hour plasma of ≥140 and <200 mg/dL, or an intervening glucose value at 30, 60, or 90 minutes on OGTT>200 mg/dL.

In some embodiments, the non-diabetic subject who will respond to the anti-CD3 antibody such as teplizumab does not have antibodies against ZnT8. In some embodiments, such non-diabetic subject is HLA-DR4+ and is not HLA-DR3+. In some embodiments, such non-diabetic subject who will respond to the anti-CD3 antibody such as teplizumab demonstrates an increase, following administration (e.g., after 1 month, after 2 months, after 3 months, or longer or shorter), in the frequency (or relative amount) of TIGIT+KLRG1+CD8+ T-cells (e.g., by flow cytometry) in peripheral blood mononuclear cells.

In some embodiments, the prophylactically effective amount comprises a 10 to 14-day course of subcutaneous (SC) injection or intravenous (IV) infusion of the anti-CD3 antibody such as teplizumab at 10-1000 micrograms/meter squared ($\mu g/m^2$). In one example, the prophylactically effective amount comprises a 14-day course IV infusion of the anti-CD3 antibody such as teplizumab at 51 $\mu g/m^2$, 103 $\mu g/m^2$, 207 $\mu g/m^2$, and 413 $\mu g/m^2$, on days 0-3, respectively, and one dose of 826 $\mu g/m^2$ on each of days 4-13. In some embodiments, the prophylactically effective amount delays median time to clinical diagnosis of T1D by at least 50%, at least 80%, or at least 90%, or at least 12 months, at least 18 months, at least 24 months, at least 36 months, at least 48 months, or at least 60 months, or longer.

In some embodiments, the course of dosing with the anti-CD3 antibody such as teplizumab can be repeated at 2 month, 4 month, 6 month, 8 month, 9 month, 10 month, 12 month, 15 month, 18 month, 24 month, 30 month, or 36 month intervals. In some embodiments, efficacy of the treatment with the anti-CD3 antibody such as teplizumab is determined as described herein, or as is known in the art, at 2 months, 4 months, 6 months, 9 months, 12 months, 15 months, 18 months, 24 months, 30 months, or 36 months subsequent to the previous treatment.

In some embodiments, a subject is administered one or more unit doses of approximately 0.5-50 ug/kg, approximately 0.5-40 ug/kg, approximately 0.5-30 ug/kg, approximately 0.5-20 ug/kg, approximately 0.5-15 ug/kg, approximately 0.5-10 ug/kg, approximately 0.5-5 ug/kg, approximately 1-5 ug/kg, approximately 1-10 ug/kg, approximately 20-40 ug/kg, approximately 20-30 ug/kg, approximately 22-28 ug/kg or approximately 25-26 ug/kg of the anti-CD3 antibody such as teplizumab to prevent, treat or ameliorate one or more symptoms of T1D. In some embodiments, a subject is administered one or more unit doses of about 200 ug/kg, 178 ug/kg, 180 ug/kg, 128 ug/kg, 100 ug/kg, 95 ug/kg, 90 ug/kg, 85 ug/kg, 80 ug/kg, 75 ug/kg, 70 ug/kg, 65 ug/kg, 60 ug/kg, 55 ug/kg, 50 ug/kg, 45 ug/kg, 40 ug/kg, 35 ug/kg, 30 ug/kg, 26 ug/kg, 25 ug/kg, 20 ug/kg, 15 ug/kg, 13 ug/kg, 10 ug/kg, 6.5 ug/kg, 5 ug/kg, 3.2 ug/kg, 3 ug/kg, 2.5 ug/kg, 2 ug/kg, 1.6 ug/kg, 1.5 ug/kg, 1 ug/kg, 0.5 ug/kg, 0.25 ug/kg, 0.1 ug/kg, or 0.05 ug/kg of the anti-CD3 antibody such as teplizumab to prevent, treat or ameliorate one or more symptoms of T1D.

In some embodiments, a subject is administered one or more doses of the anti-CD3 antibody such as teplizumab at about 5-1200 $ug/m^2$, preferably, 51-826 $ug/m^2$. In some embodiments, a subject is administered one or more unit doses of 1200 $ug/m^2$, 1150 $ug/m^2$, 1100 $ug/m^2$, 1050 $ug/m^2$, 1000 $ug/m^2$, 950 $ug/m^2$, 900 $ug/m^2$, 850 $ug/m^2$, 800 $ug/m^2$, 750 $ug/m^2$, 700 $ug/m^2$, 650 $ug/m^2$, 600 $ug/m^2$, 550 $ug/m^2$, 500 $ug/m^2$, 450 $ug/m^2$, 400 $ug/m^2$, 350 $ug/m^2$, 300 $ug/m^2$, 250 $ug/m^2$, 200 $ug/m^2$, 150 $ug/m^2$, 100 $ug/m^2$, 50 $ug/m^2$, 40 $ug/m^2$, 30 $ug/m^2$, 20 $ug/m^2$, 15 $ug/m^2$, 10 $ug/m^2$, or 5 $ug/m^2$ of the anti-CD3 antibody such as teplizumab to prevent, treat, slow the progression of, delay the onset of or ameliorate one or more symptoms of T1D.

In some embodiments, the subject is administered a treatment regimen comprising one or more doses of a prophylactically effective amount of the anti-CD3 antibody such as teplizumab, wherein the course of treatment is administered over 2 days, 3 days, 4 days, 5 days, 6 days, 7 days, 8 days, 9 days, 10 days, 11 days, 12 days, 13 days or 14 days. In some embodiments, the treatment regimen comprises administering doses of the prophylactically effective amount every day, every 2nd day, every 3rd day or every 4th day. In some embodiments, the treatment regimen comprises administering doses of the prophylactically effective amount on Monday, Tuesday, Wednesday, Thursday of a given week and not administering doses of the prophylactically effective amount on Friday, Saturday, and Sunday of the same week until 14 doses, 13 doses, 12 doses, 11 doses, 10 doses, 9 doses, or 8 doses have been administered. In some embodiments, the dose administered is the same each day of the regimen.

In some embodiments, a subject is administered a treatment regimen comprising one or more doses of a prophylactically effective amount of the anti-CD3 antibody such as teplizumab, wherein the prophylactically effective amount is 200 ug/kg/day, 175 ug/kg/day, 150 ug/kg/day, 125 ug/kg/day, 100 ug/kg/day, 95 ug/kg/day, 90 ug/kg/day, 85 ug/kg/day, 80 ug/kg/day, 75 ug/kg/day, 70 ug/kg/day, 65 ug/kg/day, 60 ug/kg/day, 55 ug/kg/day, 50 ug/kg/day, 45 ug/kg/day, 40 ug/kg/day, 35 ug/kg/day, 30 ug/kg/day, 26 ug/kg/day, 25 ug/kg/day, 20 ug/kg/day, 15 ug/kg/day, 13 ug/kg/day, 10 ug/kg/day, 6.5 ug/kg/day, 5 ug/kg/day, 3.2 ug/kg/day, 3 ug/kg/day, 2.5 ug/kg/day, 2 ug/kg/day, 1.6 ug/kg/day, 1.5 ug/kg/day, 1 ug/kg/day, 0.5 ug/kg/day, 0.25 ug/kg/day, 0.1 ug/kg/day, or 0.05 ug/kg/day; and/or wherein the prophylactically effective amount is 1200 $ug/m^2$/day, 1150 $ug/m^2$/day, 1100 $ug/m^2$/day, 1050 $ug/m^2$/day, 1000 $ug/m^2$/day, 950 $ug/m^2$/day, 900 $ug/m^2$/day, 850 $ug/m^2$/day, 800 $ug/m^2$/day, 750 $ug/m^2$/day, 700 $ug/m^2$/day, 650 $ug/m^2$/day, 600 $ug/m^2$/day, 550 $ug/m^2$/day, 500 $ug/m^2$/day, 450 $ug/m^2$/day, 400 $ug/m^2$/day, 350 $ug/m^2$/day, 300 $ug/m^2$/day, 250 $ug/m^2$ day, 200 $ug/m^2$/day, 150 $ug/m^2$/day, 100 $ug/m^2$/day, 50 $ug/m^2$/day, 40 $ug/m^2$ day, 30 $ug/m^2$/day, 20 $ug/m^2$/day, 15 $ug/m^2$/day, 10 $ug/m^2$/day, or 5 $ug/m^2$/day.

In some embodiments, the intravenous dose of 1200 $ug/m^2$ or less, 1150 $ug/m^2$ or less, 1100 $ug/m^2$ or less, 1050 $ug/m^2$ or less, 1000 $ug/m^2$ or less, 950 $ug/m^2$ or less, 900 $ug/m^2$ or less, 850 $ug/m^2$ or less, 800 $ug/m^2$ or less, 750 $ug/m^2$ or less, 700 $ug/m^2$ or less, 650 $ug/m^2$ or less, 600 $ug/m^2$ or less, 550 $ug/m^2$ or less, 500 $ug/m^2$ or less, 450 $ug/m^2$ or less, 400 $ug/m^2$ or less, 350 $ug/m^2$ or less, 300 $ug/m^2$ or less, 250 $ug/m^2$ or less, 200 $ug/m^2$ or less, 150 ug/m² or less, 100 ug/m² or less, 50 ug/m² or less, 40 ug/m² or less, 30 ug/m² or less, 20 ug/m² or less, 15 ug/m² or less, 10 ug/m² or less, or 5 ug/m² or less of the anti-CD3 antibody such as teplizumab is administered over about 24 hours, about 22 hours, about 20 hours, about 18 hours, about 16 hours, about 14 hours, about 12 hours, about 10 hours, about 8 hours, about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of type 1 diabetes. The total dosage over the duration of the regimen is preferably a total of less than 9000 ug/m², 8000 ug/m², 7000 ug/m², 6000 ug/m², and may be less than 5000 ug/m², 4000 ug/m², 3000 ug/m², 2000 ug/m², or 1000 ug/m². In some embodiments, the total dosage administered in the regimen is 100 ug/m² to 200 ug/m², 100 ug/m² to 500 ug/m², 100 ug/m² to 1000 ug/m², or 500 ug/m² to 1000 ug/m².

In some embodiments, the dose escalates over the first fourth, first half or first ⅔ of the doses (e.g., over the first 2, 3, 4, 5, or 6 days of a 10, 12, 14, 16, 18 or 20-day regimen of one dose per day) of the treatment regimen until the daily prophylactically effective amount of the anti-CD3 antibody such as teplizumab is achieved. In some embodiments, a subject is administered a treatment regimen comprising one or more doses of a prophylactically effective amount of the anti-CD3 antibody such as teplizumab, wherein the prophylactically effective amount is increased by, e.g., 0.01 ug/kg, 0.02 ug/kg, 0.04 ug/kg, 0.05 ug/kg, 0.06 ug/kg, 0.08 ug/kg, 0.1 ug/kg, 0.2 ug/kg, 0.25 ug/kg, 0.5 ug/kg, 0.75 ug/kg, 1 ug/kg, 1.5 ug/kg, 2 ug/kg, 4 ug/kg, 5 ug/kg, 10 ug/kg, 15 ug/kg, 20 ug/kg, 25 ug/kg, 30 ug/kg, 35 ug/kg, 40 ug/kg, 45 ug/kg, 50 ug/kg, 55 ug/kg, 60 ug/kg, 65 ug/kg, 70 ug/kg, 75 ug/kg, 80 ug/kg, 85 ug/kg, 90 ug/kg, 95 ug/kg, 100 ug/kg, or 125 ug/kg each day; or increased by, e.g., 1 ug/m², 5 ug/m², 10 ug/m², 15 ug/m², 20 ug/m², 30 ug/m², 40 ug/m², 50 ug/m², 60 ug/m², 70 ug/m², 80 ug/m², 90 ug/m², 100 ug/m², 150 ug/m², 200 ug/m², 250 ug/m², 300 ug/m², 350 ug/m², 400 ug/m², 450 ug/m², 500 ug/m², 550 ug/m², 600 ug/m², or 650 ug/m², each day as treatment progresses. In some embodiments, a subject is administered a treatment regimen comprising one or more doses of a prophylactically effective amount of the anti-CD3 antibody such as teplizumab, wherein the prophylactically effective amount is increased by a factor of 1.25, a factor of 1.5, a factor of 2, a factor of 2.25, a factor of 2.5, or a factor of 5 until the daily prophylactically effective amount of the anti-CD3 antibody such as teplizumab is achieved.

In some embodiments, a subject is intramuscularly administered one or more doses of a 200 ug/kg or less, preferably 175 ug/kg or less, 150 ug/kg or less, 125 ug/kg or less, 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, otelixizumab or foralumab, to prevent, treat or ameliorate one or more symptoms of T1D.

In some embodiments, a subject is subcutaneously administered one or more doses of a 200 ug/kg or less, preferably 175 ug/kg or less, 150 ug/kg or less, 125 ug/kg or less, 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, otelixizumab or foralumab, to prevent, treat or ameliorate one or more symptoms of T1D.

In some embodiments, a subject is intravenously administered one or more doses of a 100 ug/kg or less, preferably 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, otelixizumab or foralumab, to prevent, treat or ameliorate one or more symptoms of T1D. In some embodiments, the intravenous dose of 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, otelixizumab or foralumab, is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of T1D.

In some embodiments, a subject is orally administered one or more doses of a 100 ug/kg or less, preferably 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, otelixizumab or foralumab, to prevent, treat or ameliorate one or more symptoms of T1D. In some embodiments, the oral dose of 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, otelixizumab or foralumab, is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of T1D.

In some embodiments in which escalating doses are administered for the first days of the dosing regimen, the dose on day 1 of the regimen is 5-100 ug/m²/day, preferably 51 ug/m2/day and escalates to the daily dose as recited immediately above by day 3, 4, 5, 6 or 7. For example, on day 1, the subject is administered a dose of approximately 51 ug/m²/day, on day 2 approximately 103 ug/m²/day, on day 3 approximately 207 ug/m²/day, on day 4 approximately 413 ug/m²/day and on subsequent days of the regimen (e.g., days 5-14) 826 ug/m²/day. In some embodiments, on day 1, the subject is administered a dose of approximately 227 ug/m²/day, on day 2 approximately 459 ug/m²/day, on day 3 and subsequent days, approximately 919 ug/m²/day. In some embodiments, on day 1, the subject is administered a dose of approximately 284 ug/m²/day, on day 2 approximately 574 ug/m²/day, on day 3 and subsequent days, approximately 1148 ug/m²/day.

In some embodiments, the initial dose is ¼, to ½, to equal to the daily dose at the end of the regimen but is administered in portions at intervals of 6, 8, 10 or 12 hours. For example, a 13 ug/kg/day dose is administered in four doses of 3-4 ug/kg at intervals of 6 hours to reduce the level of cytokine release caused by administration of the antibody. In some embodiments, to reduce the possibility of cytokine release and other adverse effects, the first 1, 2, 3, or 4 doses or all the doses in the regimen are administered more slowly by intravenous administration. For example, a dose of 51 ug/m²/day may be administered over about 5 minutes, about 15 minutes, about 30 minutes, about 45 minutes, about 1 hour, about 2 hours, about 4 hours, about 6 hours, about 8 hours, about 10 hours, about 12 hours, about 14 hours, about 16 hours, about 18 hours, about 20 hours, and about 22 hours. In some embodiments, the dose is administered by slow infusion over a period of, e.g., 20 to 24 hours. In some embodiments, the dose is infused in a pump, preferably increasing the concentration of antibody administered as the infusion progresses.

In some embodiments, a set fraction of the doses for the 51 ug/m²/day to 826 ug/m²/day regimen described above is administered in escalating doses. In some embodiments, the fraction is ⅒, ¼, ⅓, ½, ⅔ or ¾ of the daily doses of the regimens described above. Accordingly, when the fraction is ⅒, the daily doses will be 5.1 ug/m² on day 1, 10.3 ug/m² on day 2, 20.7 g/m² on day 3, 41.3 ug/m² on day 4, and 82.6 ug/m² on days 5 to 14. When the fraction is ¼, the doses will be 12.75 ug/m² on day 1, 25.5 ug/m² on day 2, 51 ug/m² on day 3, 103 ug/m² on day 4, and 207 ug/m² on days 5 to 14. When the fraction is ⅓, the doses will be 17 ug/m² on day 1, 34.3 ug/m² on day 2, 69 ug/m² on day 3, 137.6 ug/m² on day 4, and 275.3 ug/m² on days 5 to 14. When the fraction is ½, the doses will be 25.5 ug/m² on day 1, 51 ug/m² on day 2, 103 ug/m² on day 3, 207 ug/m² on day 4, and 413 ug/m² on days 5 to 14. When the fraction is ⅔, the doses will be 34 ug/m² on day 1, 69 ug/m² on day 2, 137.6 ug/m² on day 3, 275.3 ug/m² on day 4, and 550.1 ug/m² on days 5 to 14. When the fraction is ¾, the doses will be 38.3 ug/m² on day 1, 77.3 ug/m² on day 2, 155.3 ug/m² on day 3, 309.8 ug/m² on day 4, and 620 ug/m² on days 5 to 14. In some embodiments, the regimen is identical to one of those described above but only over days 1 to 4, days 1 to 5, or days 1 to 6. For example, in some embodiments, the doses will be 17 ug/m² on day 1, 34.3 ug/m² on day 2, 69 ug/m² on day 3, 137.6 ug/m² on day 4, and 275.3 ug/m² on days 5 and 6.

In some embodiments, the anti-CD3 antibody such as teplizumab, otelixizumab or foralumab, is not administered by daily doses over a number of days, but is rather administered by infusion in an uninterrupted manner over 4 hours, 6 hours, 8 hours, 10 hours, 12 hours, 15 hours, 18 hours, 20 hours, 24 hours, 30 hours or 36 hours. The infusion may be constant or may start out at a lower dosage for, for example, the first 1, 2, 3, 5, 6, or 8 hours of the infusion and then increase to a higher dosage thereafter. Over the course of the infusion, the patient receives a dose equal to the amount administered in the 5 to 20-day regimens set forth above. For example, a dose of approximately 150 ug/m², 200 ug/m², 250 ug/m², 500 ug/m², 750 ug/m², 1000 ug/m², 1500 ug/m², 2000 ug/m², 3000 ug/m², 4000 ug/m², 5000 ug/m², 6000 ug/m², 7000 ug/m², 8000 ug/m², or 9000 ug/m². In particular, the speed and duration of the infusion is designed to minimize the level of free anti-CD3 antibody such as teplizumab, otelixizumab or foralumab in the subject after administration. In some embodiments, the level of free anti-CD3 antibody such as teplizumab should not exceed 200 ng/ml free antibody. In addition, the infusion is designed to achieve a combined T cell receptor coating and modulation of at least 50%, 60%, 70%, 80%, 90%, 95% or of 100%.

In some embodiments, the anti-CD3 antibody such as teplizumab, otelixizumab or foralumab is administered chronically to treat, prevent, or slow or delay the onset or progression, or ameliorate one or more symptoms of type 1 diabetes. For example, in some embodiments, a low dose of the anti-CD3 antibody such as teplizumab is administered once a month, twice a month, three times per month, once a week or even more frequently either as an alternative to the 6 to 14-day dosage regimen discussed above or after administration of such a regimen to enhance or maintain its effect. Such a low dose may be anywhere from 1 ug/m² to 100 ug/m², such as approximately 5 ug/m², 10 ug/m², 15 ug/m², 20 ug/m², 25 ug/m², 30 ug/m², 35 ug/m², 40 ug/m², 45 ug/m², or 50 ug/m².

In some embodiments, the subject may be re-dosed at some time subsequent to administration of the anti-CD3 antibody such as teplizumab, otelixizumab or foralumab dosing regimen, for example, based upon one or more physiological parameters or may be done as a matter of course. Such redosing may be administered and/or the need for such redosing evaluated 2 months, 4 months, 6 months, 8 months, 9 months, 1 year, 15 months, 18 months, 2 years, 30 months or 3 years after administration of a dosing regimen and may include administering a course of treatment every 6 months, 9 months, 1 year, 15 months, 18 months, 2 years, 30 months or 3 years indefinitely.

EXAMPLE

Example 1: Teplizumab Improves and Stabilizes Beta Cell Function in Antibody Positive High-Risk Individuals Abstract We analyzed the effects of a single 14-day course of teplizumab treatment on metabolic function and immune cells among participants in a randomized controlled trial of non-diabetic relatives at high-risk for Type 1 diabetes (T1D). In an extended follow up (923-day median) of a previous report of teplizumab treatment the median times to diagnosis were 59.6 and 24.4 (or 27.1 according to Sims et al., Sci. Transl. Med. 13, eabc8980 (2021), incorporated herein by reference) months for teplizumab and placebo treated participants, respectively (HR=0.457, p=0.01). Fifty percent of teplizumab-treated but only 22% of the placebo-treated remained diabetes free. Glucose tolerance, C-peptide area under the curve (AUC), and insulin secretory rates were calculated, and relationships to T cell subsets and function were analyzed. Teplizumab treatment improved beta cell function, reflected by average on-study C-peptide AUC (1.96 vs 1.68 pmol/ml; p=0.009) (or 1.94 versus 1.72 pmol/ml; P=0.006 according to Sims et al., *Sci. Transl. Med.* 13, eabc8980 (2021), incorporated herein by reference).

Drug treatment reversed a decline in insulin secretion prior to enrollment followed by stabilization of the declining C-peptide AUC seen with placebo treatment. The changes in C-peptide with teplizumab treatment were associated with increases in partially exhausted memory KLRG1+ TIGIT+ CD8+ T cells (r=0.44; p=0.014) and reduced secretion of IFNγ and TNFα. A single course of teplizumab had lasting effects on delay of T1D diagnosis and improved beta cell function in high-risk individuals. Changes in CD8+ T cell subsets indicate that partially exhausted effector cells are associated with clinical response. This is the first trial to show successful modulation of autoimmune diabetes with immune therapy.

Introduction

Type 1 diabetes (T1D) is an autoimmune disease characterized by T-cell mediated destruction of insulin producing beta cells within the pancreatic islets of Langerhans. Longitudinal observational studies over more than 30 years have described the progression of the autoimmune disease from the first appearance of autoantibodies until beta cell function is critically impaired and the clinical diagnosis, often with ketoacidosis, occurs (1-5). T1D is associated with a need for lifelong exogenous insulin administration for survival, increased morbidity and mortality due to immediate (e.g. hypoglycemia) and long-term complications (e.g. vascular, renal, and eye disease), and reduced life-span, life impairments, and considerable health-care-related costs (6-9). Thus, approaches to prevent progression to clinical T1D before irremediable beta cell destruction and insulin deficiency, are of paramount importance.

Changes in beta cell function precede the clinical diagnosis of T1D and have been studied in natural history cohorts of individuals who are identified as at-risk for the disease based on the presence of islet autoantibodies (10-12). Some studies suggest an ongoing and intermittently progressive decline in beta cell function, that begins years before clinical diagnosis at a time when glucose tolerance is normal. During this period there are signs of ongoing autoimmunity: Based on the findings of the natural history, individuals with two or more islet autoantibodies have been classified as stages of T1D, with further specification according to the level of metabolic dysfunction: Stage 1 prior to glucose abnormalities, Stage 2 with dysglycemia during an oral glucose tolerance test (OGTT), and Stage 3 at clinical presentation with hyperglycemia (2, 13, 14). However, the relationships between changes in beta cell function and clinical disease remain poorly defined. It is known, for example, that glucose tolerance, defined through responses to an oral glucose tolerance test (OGTT), may fluctuate between abnormal and normal values within an individual who is at risk (15, 16). In addition, OGTT glucose tolerance classifications used to designate a clinical diagnosis, and beta cell function, measured by C-peptide responses to a metabolic challenge, may not be closely related and at diagnosis using an OGTT, many individuals have clinically meaningful C-peptide responses (15-18).

Based on successes from previous studies in patients with Stage 3 T1D (i.e. after clinical diagnosis) with teplizumab, an Fc receptor-nonbinding anti-CD3E monoclonal antibody, that showed reduced decline in stimulated C-peptide responses compared to placebo or control participants (19-25), in the TrialNet TN10 study, we conducted a randomized Phase II trial of teplizumab in individuals with Stage 2 disease, to test whether treatment would prevent or delay the clinical diagnosis of T1D (26). In this time-to-event study, we found a delay in the median time to diagnosis of 24 months with teplizumab vs placebo, and a reduction in the rate of diabetes diagnoses from 35.9% to 14.9% per year (26). This trial represented the first to show successful prevention or delay in the diagnosis of T1D with immune therapy (27-31).

The successful outcome of the TrialNet TN10, using an intervention that modified clinical disease, has enabled us to evaluate the effects of the therapy on beta cell function and its relationship to immune modifications, even when disease progression was clinically silent. To test the hypothesis that the immune therapy would improve beta cell function in the at-risk individuals from TN10, we analyzed the results of metabolic studies in the trial and immune responses. Our data show a persistence of the duration of treatment effects on delay in clinical presentation of T1D. We show that a single course of treatment with teplizumab reversed a decline in C-peptide production prior to study entry and improved the beta cell response to oral glucose after treatment compared to placebo. Early insulin secretion was also improved with teplizumab, suggesting qualitative improvement in beta cell function. After the initial 3-6 months following treatment, the C-peptide responses were stable compared to placebo until an abrupt decline in the response approximately 6 months prior to diagnosis in those who were diagnosed with clinical T1D. The improved C-peptide responses were associated with an increase in the frequency of TIGIT+KLRG1+ memory CD8 T cells, which exhibited reduced secretion of IFNγ and TNFα, two inflammatory cytokines linked to beta cell destruction (32). These studies indicate that even prior to clinical diagnosis, treatment with teplizumab can improve metabolic function associated with modulation of pathologic T cell signatures.

Results

Figure 1B:
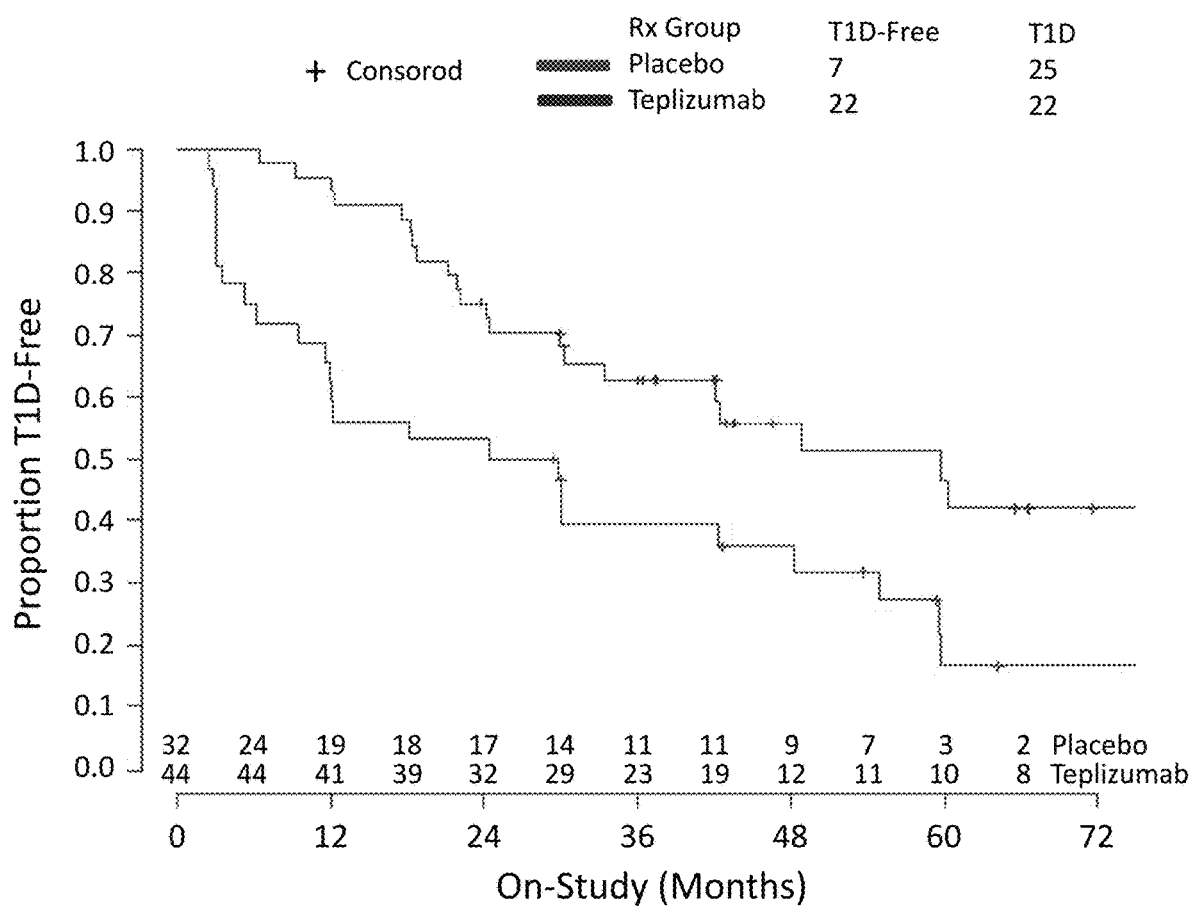
FIG. 1B shows that teplizumab treatment is associated with a sustained effect on Type 1 Diabetes progression over 923 days of follow-up. Updated Kaplan-Meier Curve based on 923 days of follow up (range 74-3,119 days). Hazard ratio for development of type 1 diabetes in teplizumab-treated participants vs. placebo was 0.457; p=0.01. The median time to diabetes was 24.4 (or 27.1 months according to Sims et al., Sci. Transl. Med. 13, eabc8980 (2021), incorporated herein by reference) and 59.6 months in the placebo and teplizumab treatment groups respectively. Updated At the conclusion of this period, 7 (22%) and 22 (50%) respectively were not diagnosed with T1D.

Teplizumab treatment resulted in a sustained delay in T1D during extended follow-up studies: A total of 76 relatives at high-risk, but without a clinical diagnosis of T1D were enrolled into the teplizumab prevention study (26). The median age was 13 (range 8-49) and all participants had 2+ autoantibody tests within the 6 months prior to enrollment. We previously reported, after a median follow up of 742 days (range 74 to 2683) that 42 were diagnosed with T1D. We have since continued to follow the study participants for a median time of 923 days (range of 74-3,119) (FIG. 1A). Over this extended period of follow-up, 25/32 (78%) ofthe placebo-treated and 22/44 (50%) of the teplizumab-treated participants were diagnosed with T1D (FIG. 1B) (Cox model adjusting for stratification and age: HR=0.457 p=0.01). The median times to diagnosis of T1D were 59.6 and 24.4 (or 27.1 according to Sims et al., *Sci. Transl. Med.* 13, eabc8980 (2021), incorporated herein by reference) months in the teplizumab and placebo treatment groups respectively. Ten of thirteen subjects followed beyond 60 months or 5 years were not diagnosed with T1D. Of these individuals, eight were in the teplizumab group and two were in the placebo group.

Figure 2A:
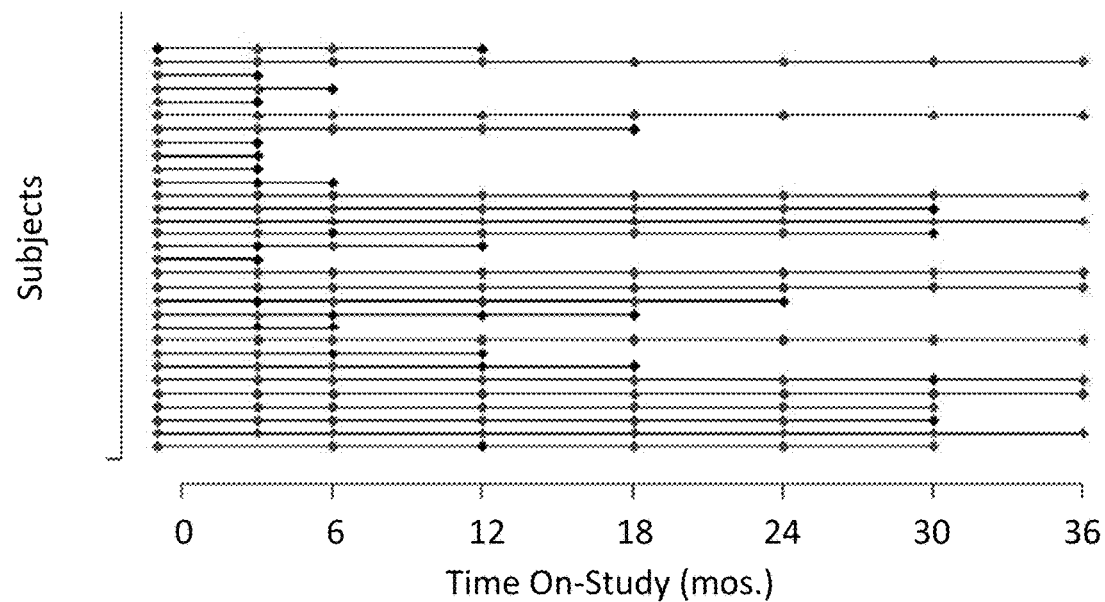
FIGS. 2A and 2B show results of OGTT tests over the first 36 months in (FIG. 2A) teplizumab and (FIG. 2B) placebo treated participants: each line represents a participant. The symbols indicate the time of OGTT testing. The results are indicated as: black dot=diabetic level/diagnosis, red dot=dysglycemia, blue dot=normal.
Figure 2B:
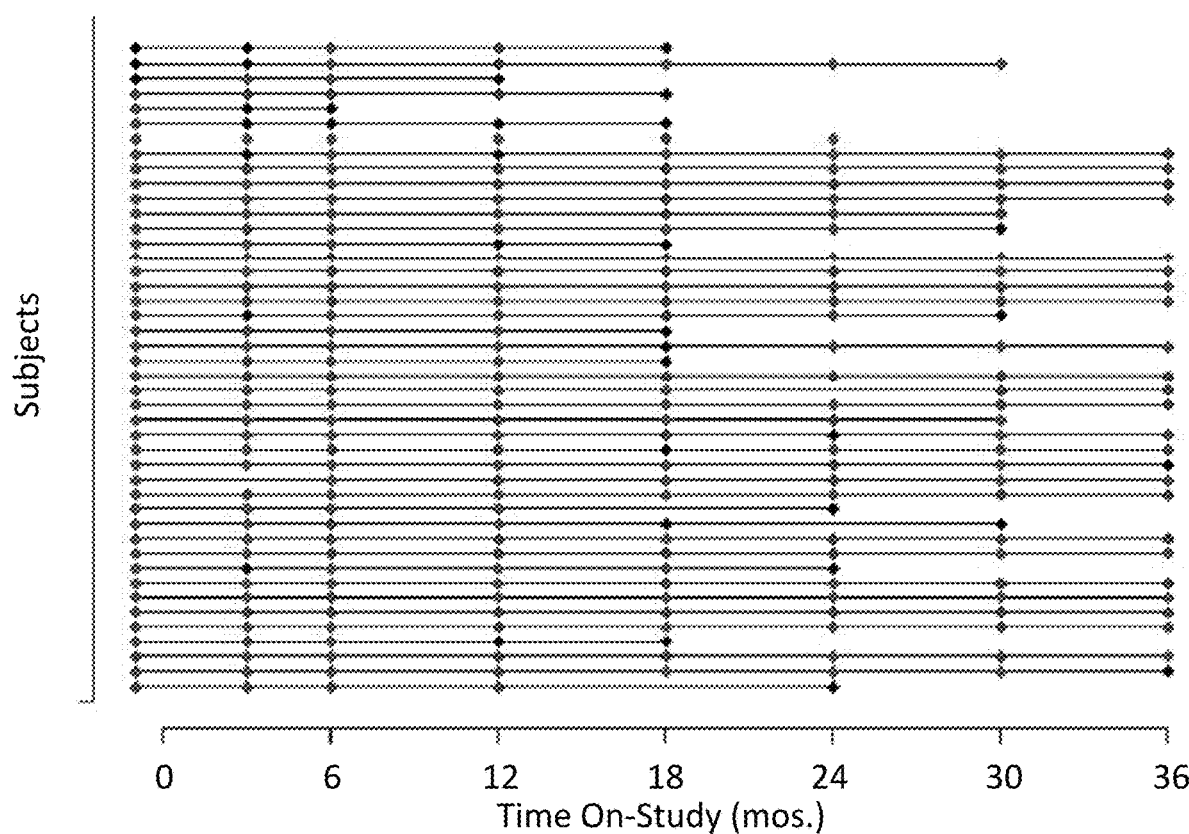

Teplizumab treatment improved quantitative OGTT glucose AUC values over the course of the study: To determine how teplizumab treatment affected glucose tolerance, we classified the outcomes of the OGTTs as normal, dysglycemic, or diabetic at study entry and tallied the frequency of these outcomes at each study visit over the first 36 months of study and afterwards (FIG. 3A; FIGS. 2A, 2B). Study participants had been recruited on the basis of a dysglycemic OGTT test result. At randomization, and consistent with the known variability of OGTT results, a small number of subjects had normal (n=3) or diabetic (n=6) glucose tolerance at that visit. The clinical diagnosis of T1D, the primary endpoint of the study, required two consecutive diabetic OGTTs hence, participants could continue in the study with a single diabetic OGTT. At the 3 month visit after teplizumab or placebo administration, the frequency of dysglycemic OGTTs declined and the frequency of normal OGTTs increased in both groups (in teplizumab treated from 6.8% to 30.2%, McNemar test: p=0.009; and in placebo from 15.6% to 36.7%, McNemar test: p=0.02). Diabetic OGTTs also increased in both groups at this timepoint, particularly in the placebo group. Afterwards, the frequency of normal and dysglycemic OGTTs remained relatively constant in the teplizumab group: the frequency of diabetic OGTTs increased in both groups but at a slower rate in the teplizumab treated participants.

Changes in OGTT classifications could overlook more subtle effects of treatment on the OGTT glucose responses. We therefore calculated and compared an average on-study glucose AUC for each individual, which was corrected for the time in study. The average on-study glucose AUC was higher in those treated with placebo vs teplizumab (mean (IQR) 175 (159, 195) mg/dl vs 165 (154, 180) mg/d1, ANCOVA teplizumab effect: 92.8%, p=0.02). (FIG. 3B, Table 1). The individual glucose AUC at the time of study entry was a predictor of the average on-study glucose AUC, but values at entry were similar between groups (unadjusted group geometric means of placebo and teplizumab: 155.5 mg/dl for placebo and 162.2 mg/dl for teplizumab, p=0.25).

TABLE 1

ANCOVA Model of Glucose On-study AUC Mean (Ln transform)

| Covariate | Coefficient | Standard Error | t-test | p-value |
|---|---|---|---|---|
| (Intercept) | 2.96 | 0.602 | 4.91 | <0.0001 |
| Glucose (baseline) | 0.44 | 0.119 | 3.7 | 0.0004 |
| Age | −0.000383 | 0.00145 | −0.264 | 0.79 |
| Teplizumab treatment | −0.0804* | 0.0343 | −2.35 | 0.02 |

*Mean of teplizumab group is 92.8% of the placebo group

Figure 4:
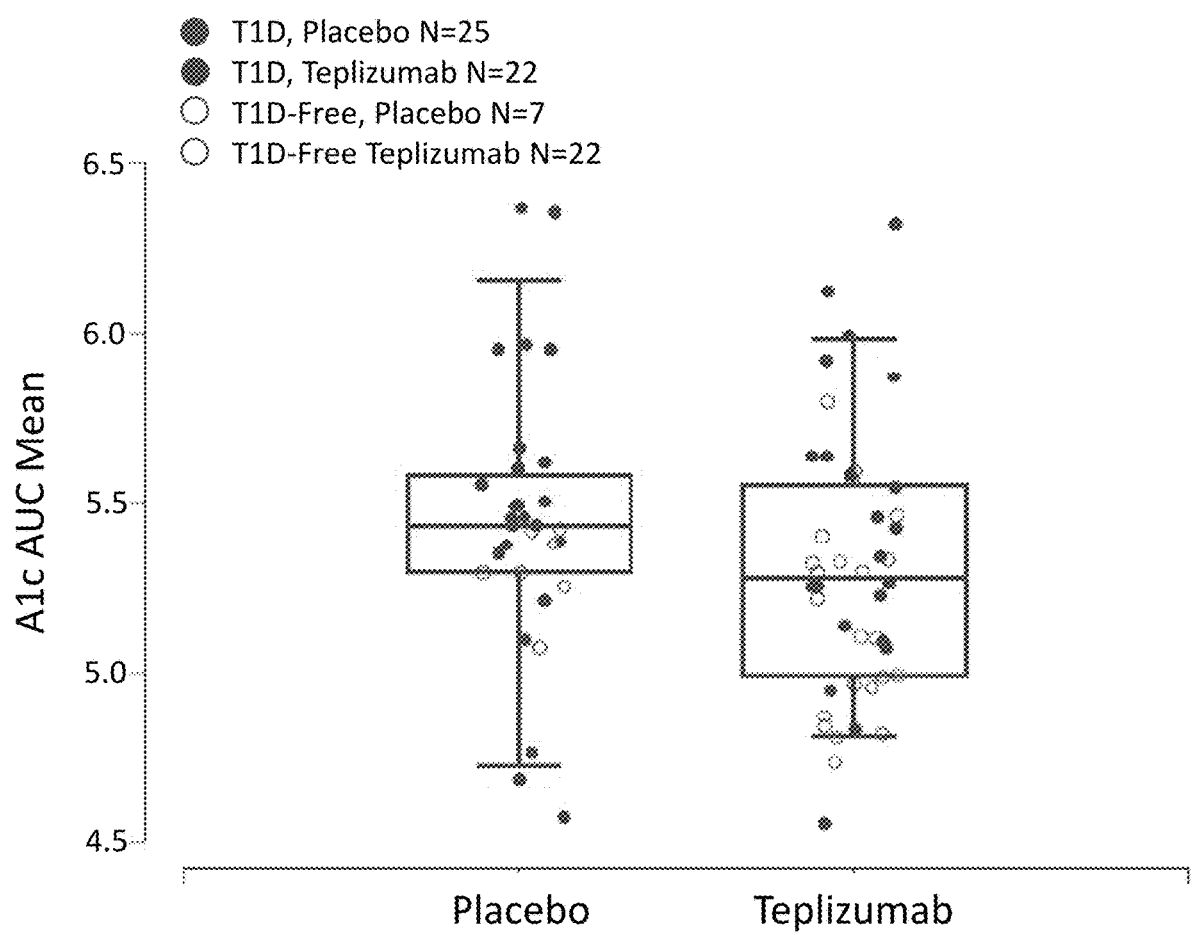
FIG. 4 shows the average on-study Hemoglobin A1c levels in the treatment groups in a boxplot displaying median and interquartile ranges for average on-study Hemoglobin A1c AUC for participants from placebo and teplizumab treated groups. ANCOVA model incorporating baseline value, age, and treatment group showed no significant impact of treatment group (p=0.14).

Average on-study Hemoglobin A1c (HbA1c) AUC was also calculated and analyzed. In contrast to glucose, the average on-study HbA1c AUC was not statistically different in those treated with placebo vs teplizumab (mean (IQR) 5.44% (5.29, 5.58) vs 5.3% (4.99, 5.55), ANCOVA treatment: p=0.14) (FIG. 4). Because the frequency of diabetes was higher in the placebo group, the similarity in the HbA1c, a measure of chronic glucose exposure, the higher average on-study glucose AUC level in the placebo group most likely was due to acute rather than chronic changes in glucose levels.

Figure 5:
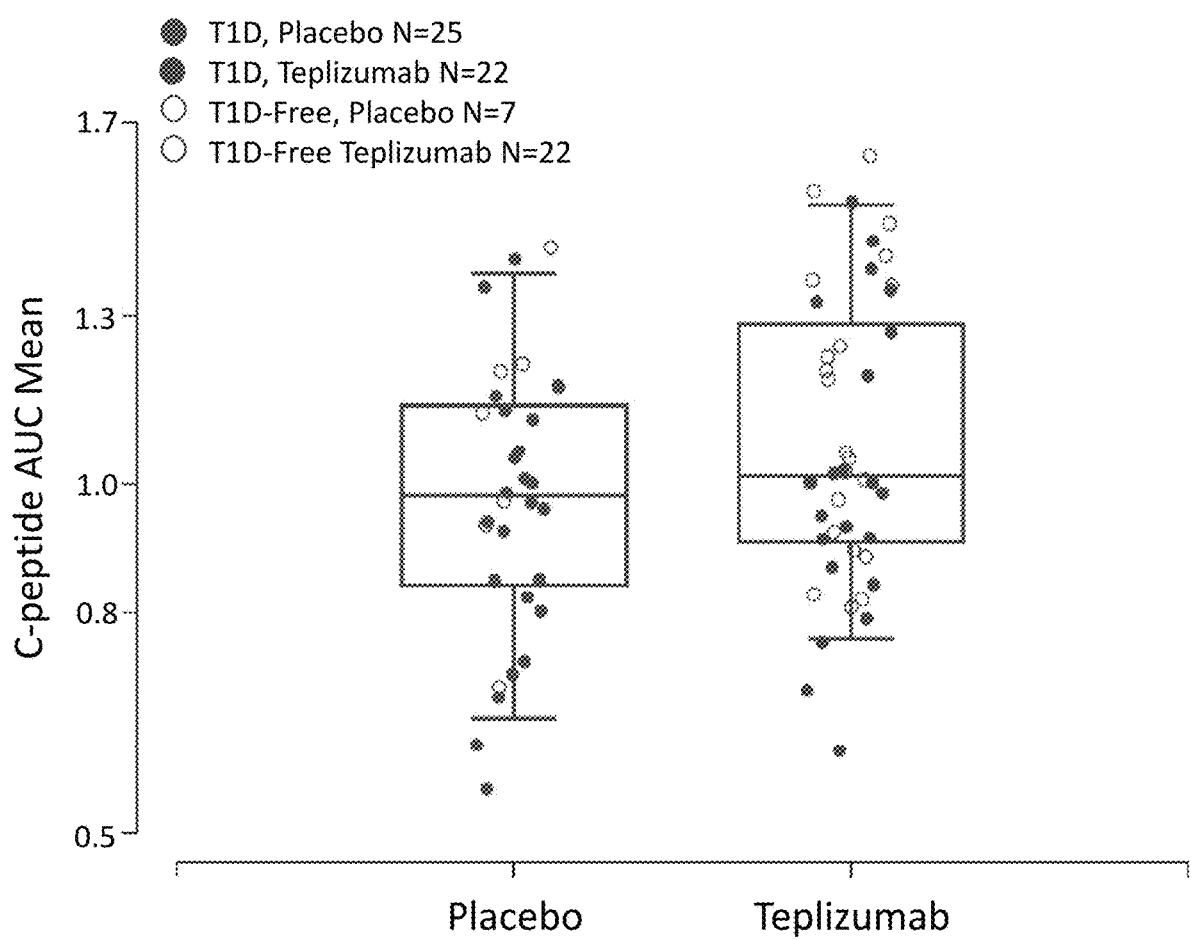
FIG. 5 shows that teplizumab treatment was associated with increased average on-study C-peptide AUC.

Teplizumab treatment increased C-peptide responses: The average on-study C-peptide AUC was greater in the teplizumab treatment group vs placebo (mean (IQR) 1.96 (1.48, 2.61) pmol/ml vs 1.68 (1.32, 2.11) pmol/ml (p=0.009) (FIG. 5, Table 2) (or 1.94 versus 1.72 pmol/ml; P=0.006 according to Sims et al., Sci. Transl. Med. 13, eabc8980 (2021), incorporated herein by reference). To assess the relationship of this endpoint with diabetes development, we compared average on-study C-peptide AUC values between participants who did or did not develop T1D during the period of observation. For the entire study population, average on-study C-peptide AUC was greater in individuals that remained diabetes free compared to those that progressed to T1D (mean (IQR) 2.18 (1.52, 2.79) pmol/ml vs. 1.76 (1.30, 2.18) pmol/ml (p=0.016). However, there was not a clear difference in the average C-peptide levels in those who were diagnosed and remained diabetes free within each treatment arm. In the placebo arm, 11/17 and 10/16 individuals in the lower and upper half of individuals respectively were diagnosed with T1D and in the teplizumab arm 13/22 and 7/22 in the lower and upper half of individuals were diagnosed with T1D (Chi-squared p=0.13) (FIG. 5).

TABLE 2

ANCOVA Model of A1c On-study AUC Mean (Ln-Ln transform)

| Covariate | Coefficient | Standard Error | t-test | p-value |
|---|---|---|---|---|
| (Intercept) | 0.0971 | 0.0481 | 2.02 | 0.05 |
| A1c (baseline) | 0.866 | 0.0964 | 8.98 | <0.0001 |
| Age | −0.000231 | 0.0003.6 | −0.755 | 0.45 |
| Teplizumab treatment | −0.0107 | 0.00712 | −1.5 | 0.14 |

Figure 6:
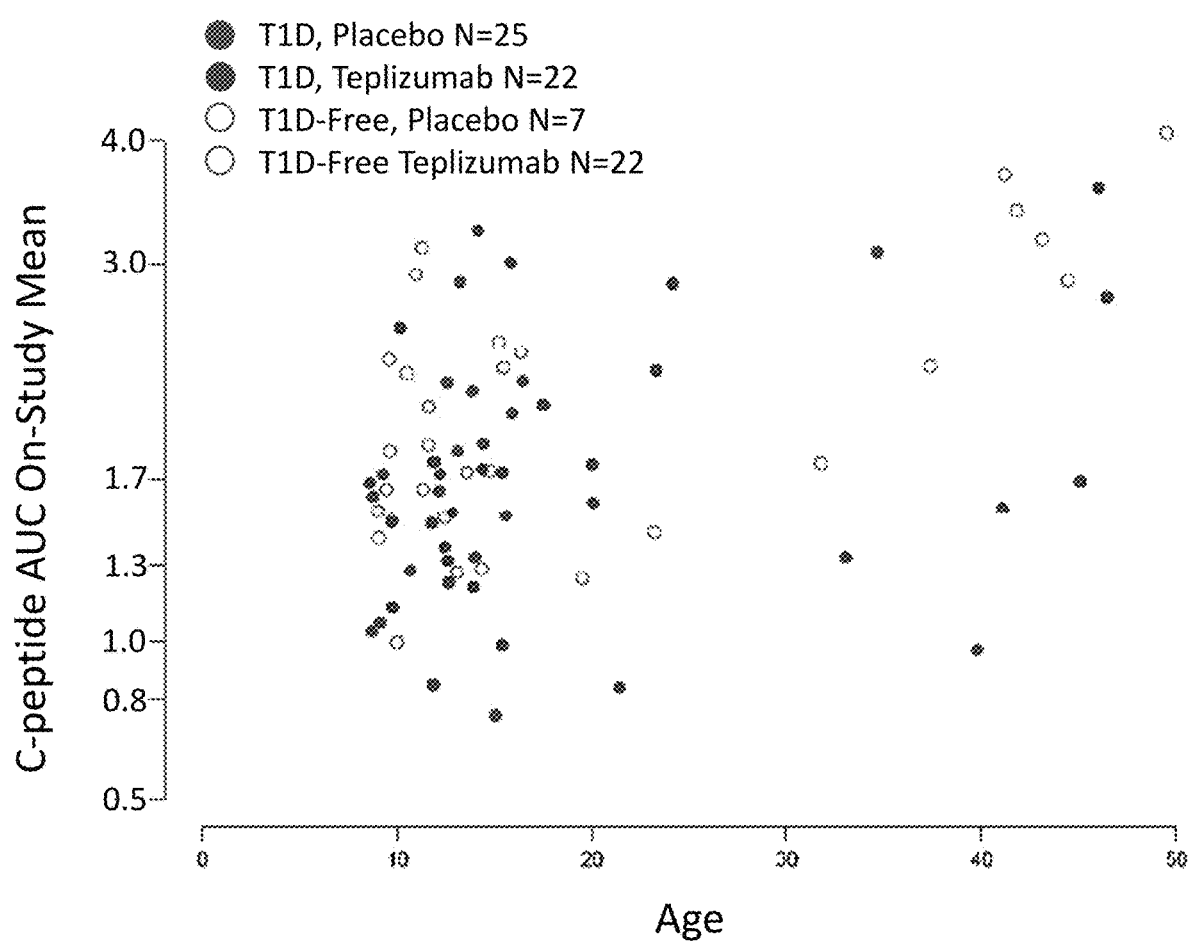
FIG. 6 shows the relationship of average on-study C-peptide AUC with age and average on-study glucose AUC.
Figure 7:
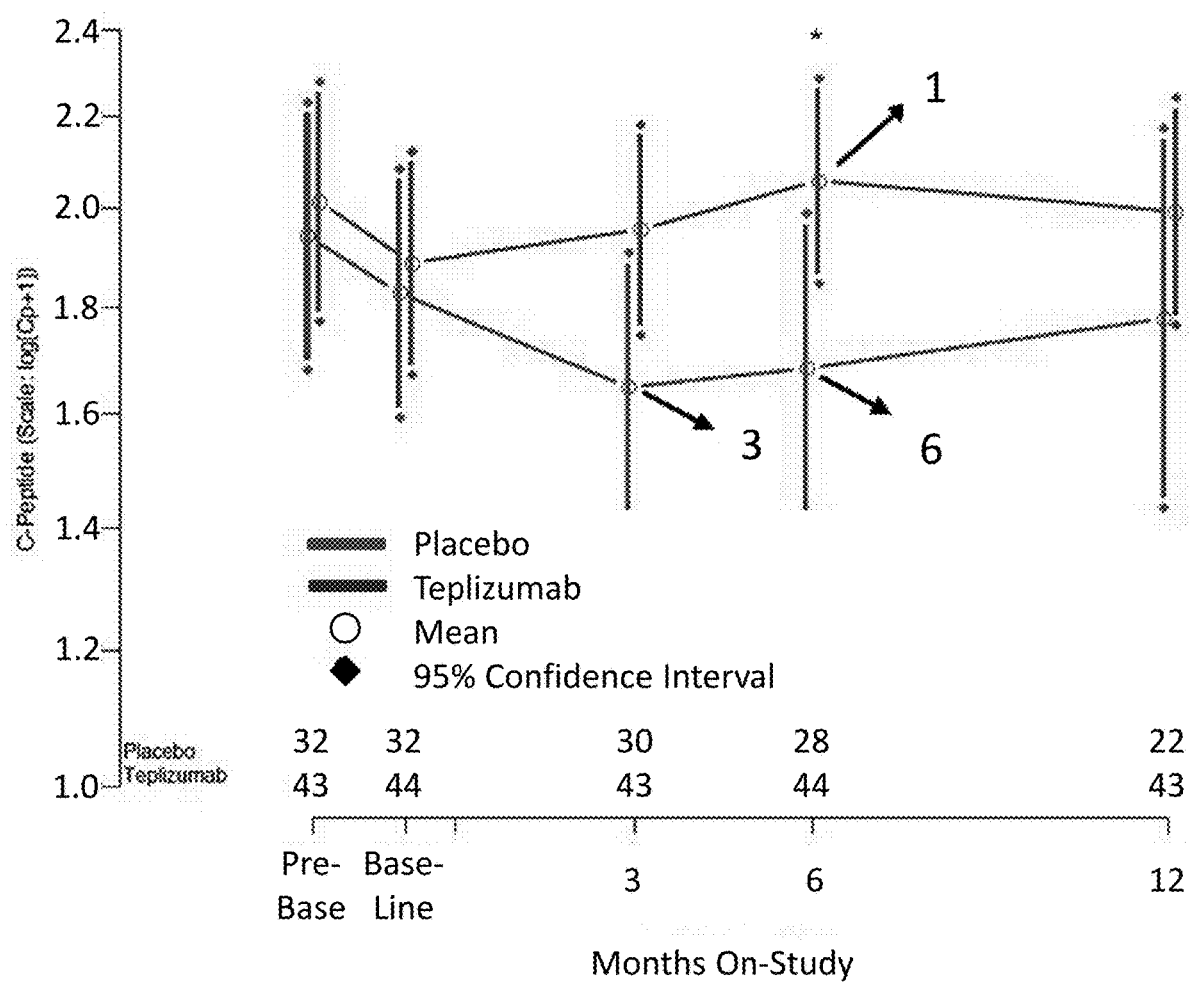
FIG. 7 shows C-peptide over time in the two treatment arms over the first year. The log-transformed mean C-peptide AUC is shown. Arrows indicate individual drop out from OGTT monitoring due to diabetes development after each timepoint. Median value for "pre-baseline" timepoint was 24. Months prior to randomization and median value for "baseline" timepoint was 0.85 months prior to randomization. *P<0.05 for comparisons of 6-month on-treatment C-peptide AUC values to baseline in the teplizumab group and 6-month C-peptide AUC values in the teplizumab group to 6-month C-peptide AUC values in the placebo group.
Figure 8A:
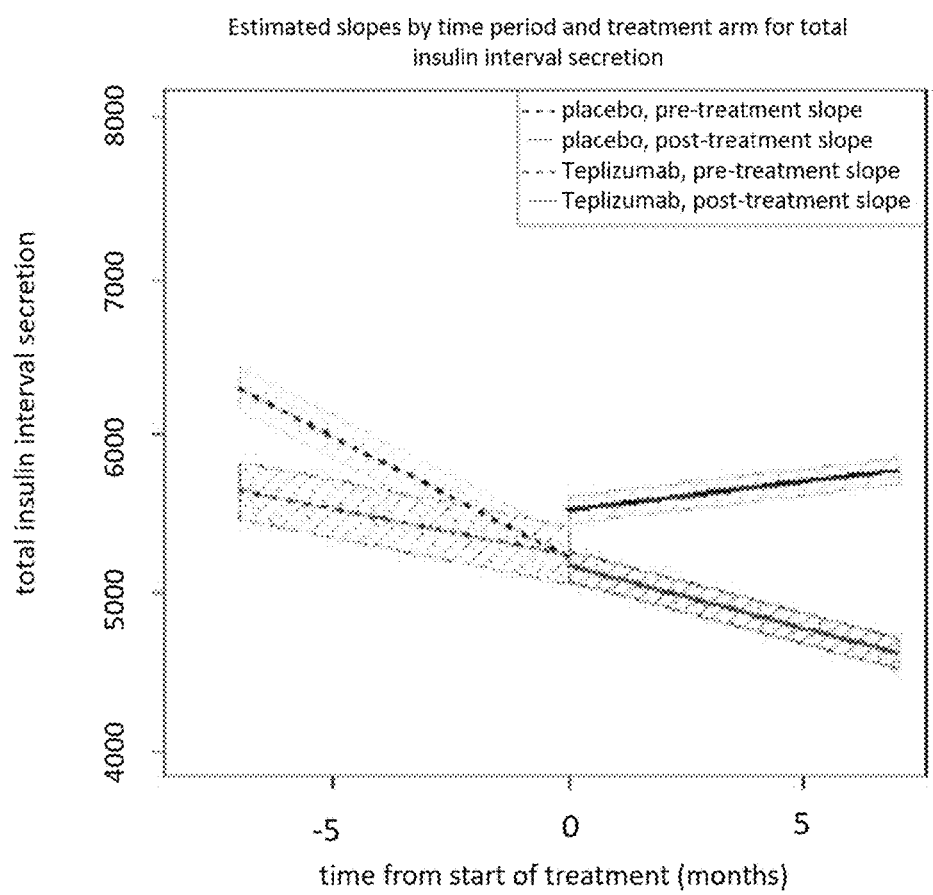
Figure 8B:
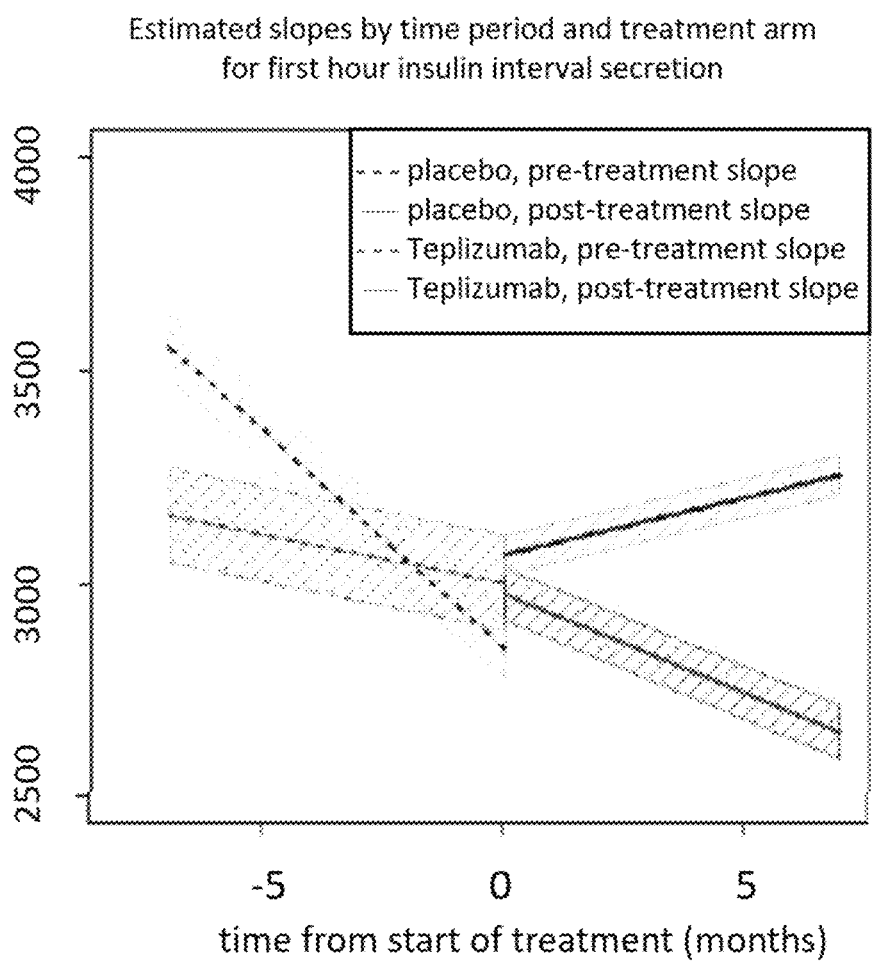
Figure 8C:
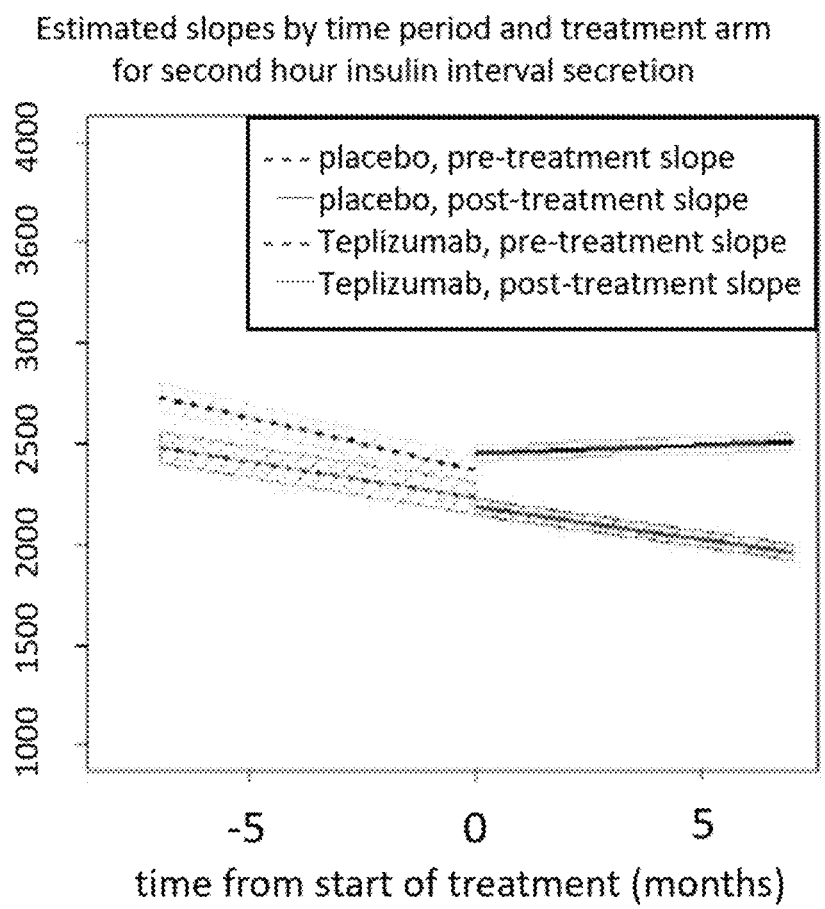
Figure 8E:
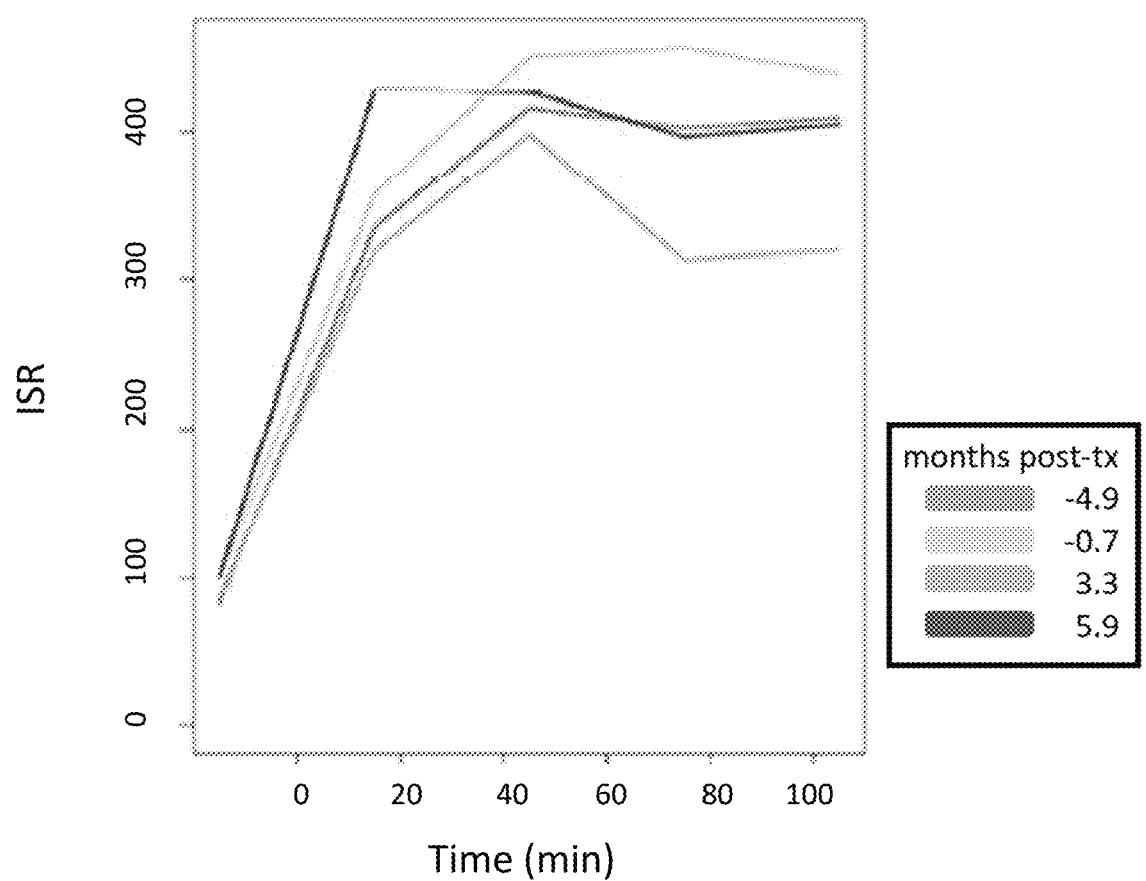
Figure 8G:
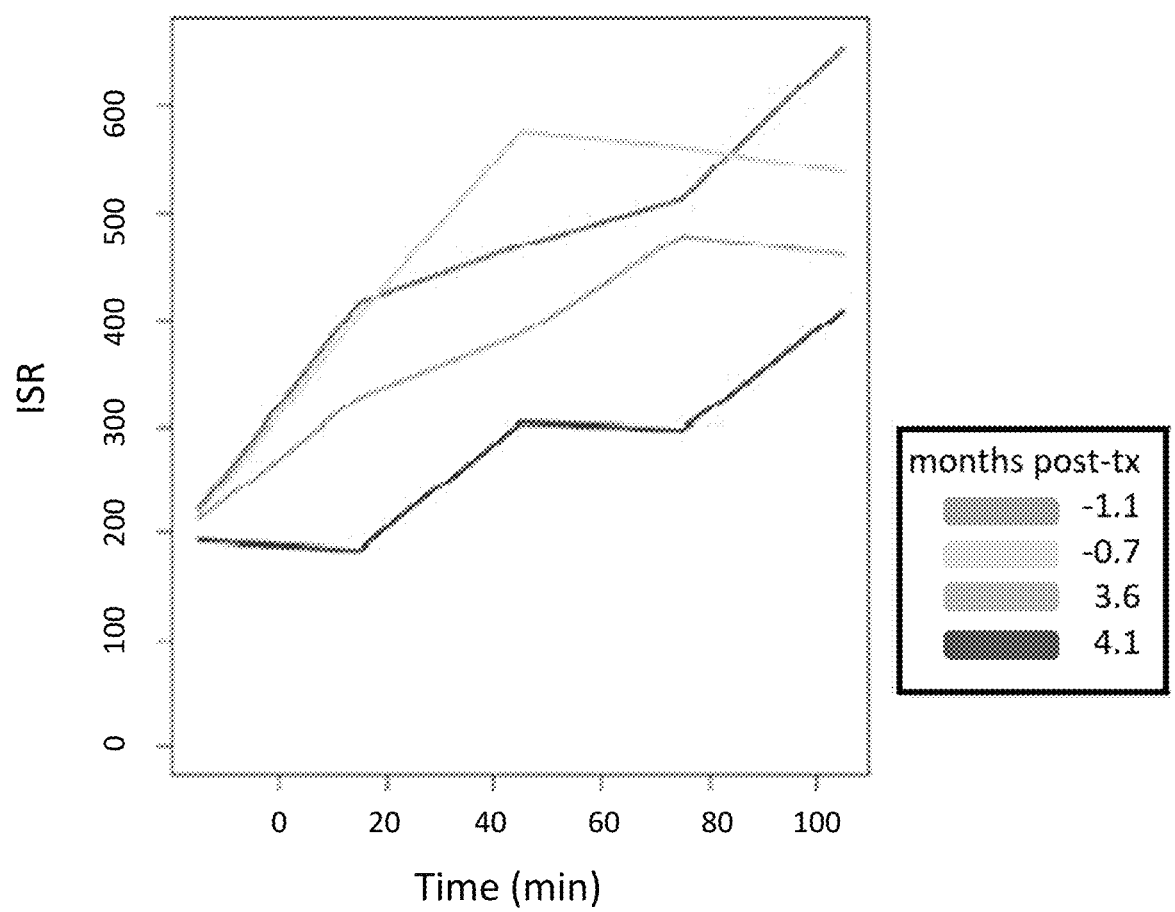

Baseline C-peptide AUC (p<0.0001) was a significant determinant of the average on-study C-peptide AUC, but baseline values were similar between treatment groups (unadjusted group means for placebo and teplizumab of 1.95 pmol/ml and 1.99 pmol/ml (p=0.454). There was also a direct relationship between the participant age and the average C-peptide AUC across both treatment arms and outcomes (FIG. 6) (from ANCOVA, r=0.44, p=0.0001) as has been noted previously in studies of individuals at risk and with new onset T1D (33). In contrast to relationships with time to clinical diagnosis (26), HLA-DR4+, HLA-DR3-, or anti-ZnT8 antibody status did not show significant interactions with the average on-study C-peptide AUC. (Using Wald test: HLA-DR3 p=0.71, HLA-DR4 p=0.27, ZnT8 p=0.79). Teplizumab treatment reverses declines in C-peptide AUC during the first 6 months of treatment: Because average on-study C-peptide AUC could obscure more pronounced between-group differences at individual study timepoints, we next analyzed the timing of the changes in C-peptide AUC relative to treatment and the insulin secretion patterns. As the participants had been recruited from the TN01 Natural History study, we were able to analyze the C-peptide response to OGTTs before enrollment, and compare these to values after enrollment in this study. Geometric-like group means over a median of 2.4 months prior to randomization, and over the 12 months after are shown in FIG. 7 and Tables 3-4. There was a decline in the C-peptide AUC prior to study enrollment in both groups (pre-baseline and baseline): placebo 1.94 (1.68, 2.23), and 1.83 pmol/ml (1.59, 2.08)), teplizumab: 2.01(1.77, 2.28) and 1.89 pmol/ml (1.67, 2.12) with an average slope of −0.0202 (−0.0471, 0.0201) (n=43). In the participants treated with placebo, the decline in C-peptide persisted at the same rate for the first 6 months after enrollment (the mean C-peptide AUC of 1.62 pmol/ml (1.35, 1.91) over the 6 months), with no significant differences in pre vs. post treatment slopes even after correction for age and the C-peptide at enrollment. In contrast, there was a significant increase in the C-peptide AUC in the teplizumab treated participants at 6 months after enrollment (6 month mean C-peptide AUC of 2.06 pmol/ml (1.85, 2.29), paired t-test p=0.02). The post-treatment slopes differed significantly between the placebo and teplizumab treated participants by ANCOVA after correcting for age and the pre-treatment slope (p=0.002).

TABLE 3

ANCOVA Model of C-peptide On-study AUC Mean (ln (x + 1) transform)

| Covariate | Coefficient | Standard Error | t-test | p-value |
|---|---|---|---|---|
| (Intercept) | −0.503 | 0.108 | −4.64 | <0.0001 |
| C-peptide (baseline) | 2.67 | 0.209 | 12.8 | <0.0001 |
| Age | 0.00389 | 0.00129 | 3.02 | 0.003 |
| Teplizumab treatment | 0.0756* | 0.0283 | 2.67 | 0.009 |

*predicted means for teplizumab and Placebo groups are 1.93 and 1.72 nano-moles/L respectively (baseline C-peptide and age set to the cohort mean)

TABLE 4

ANCOVA analysis of C-peptide AUC slope Over 1st 6 months on Study

| Covariate | Coefficient | Standard Error | t-test | p-value |
|---|---|---|---|---|
| Intercept | −0.0237 | 0.00717 | −3.3 | 0.002 |
| Pre-slope | −0.0801 | 0.0439 | −1.82 | 0.07 |
| Age | 0.00048 | 0.000284 | 1.69 | 0.10 |
| Teplizumab treatment | 0.0212 | 0.00663 | 3.2 | 0.002 |

Both total and early insulin secretion are improved by teplizumab treatment: In addition to quantitative decreases in C-peptide AUC, studies by our group and others have identified qualitative abnormalities in beta cell secretory kinetics, with loss of early insulin secretion reflecting beta cell dysfunction prior to the onset of T1D (10, 33-36). To determine whether the quantitative improvement in C-peptide AUC was associated with qualitative changes in the kinetics of insulin secretion, we determined the insulin secretory rates (ISR) during the OGTTs using a two-compartment model, and evaluated the kinetics and total insulin secretion (FIGS. 8A-8G, Table 5). We compared the OGTT insulin secretory responses and the change in the secretory responses (slope) over the same period of time in which we had found a significant improvement in the C-peptide AUC in the teplizumab treatment arm. With this analysis we could distinguish the early and late secretory responses (i.e. first and second hour). The slopes describing the change in the total, first, and second hour insulin secreted was similar in both groups prior to study enrollment (p=0.95). After treatment with teplizumab there was a significant increase in the total insulin secreted during the test in the teplizumab group that was significantly greater than in the placebo group (p=0.01, p=0.0004). The insulin secreted during the first hour continued to decline in the placebo group whereas it increased in the teplizumab group (p=0.007). The second hour of insulin secretion also improved in the teplizumab treatment group (p=0.03), but not in the placebo group (p=0.38) (Table 5). These results indicate that in the first 6 months after teplizumab treatment there is improvement in insulin secretion, particularly within the first hour of the OGTT, suggesting improved beta cell function, whereas there is continuing deterioration in insulin secretion in the placebo treated participants.

TABLE 5

Analysis of insulin secretion to oral glucose in the first 6 months after treatment

| | Medians | | |
|---|---|---|---|
| Measure to be compared between arms | Placebo | Teplizumab | p-value |
| First hour insulin interval secretion | | | |
| Pre-treatment slope | −259.5 | −422.7 | 0.79 |
| Post-treatment slope | −476.2 | 371.0 | 0.0003 |
| Paired pre- vs. post-rx p-values* within arms | p = 0.86 | p = 0.007 | — |
| Second hour insulin interval secretion | | | |
| Pre-treatment slope | −728.2 | −383.6 | 0.78 |
| Post-treatment slope | −186.8 | 442.5 | 0.003 |
| Paired pre- vs. post-rx p-values* within arms | p = 0.38 | p = 0.03 | — |
| Insulin interval secretion (2 hr) | | | |
| Pre-treatment slope | −1245.0 | −1024.0 | 0.95 |
| Post-treatment slope | −1037.4 | 1085.8 | 0.0004 |
| Paired pre- vs. post-rx p-values* within arms | p = 0.80 | p = 0.01 | — | where cliff = (post-rx slope)-(pre-rx slope)
*p-values based on Wilcoxon signed rank (paired) test comparing the pre- vs. post-rx slopes by subject; evaluation of how much changes in these measures changed pre- vs. post-rx by subject and across those subjects in each treatment arm.

Figure 9B:
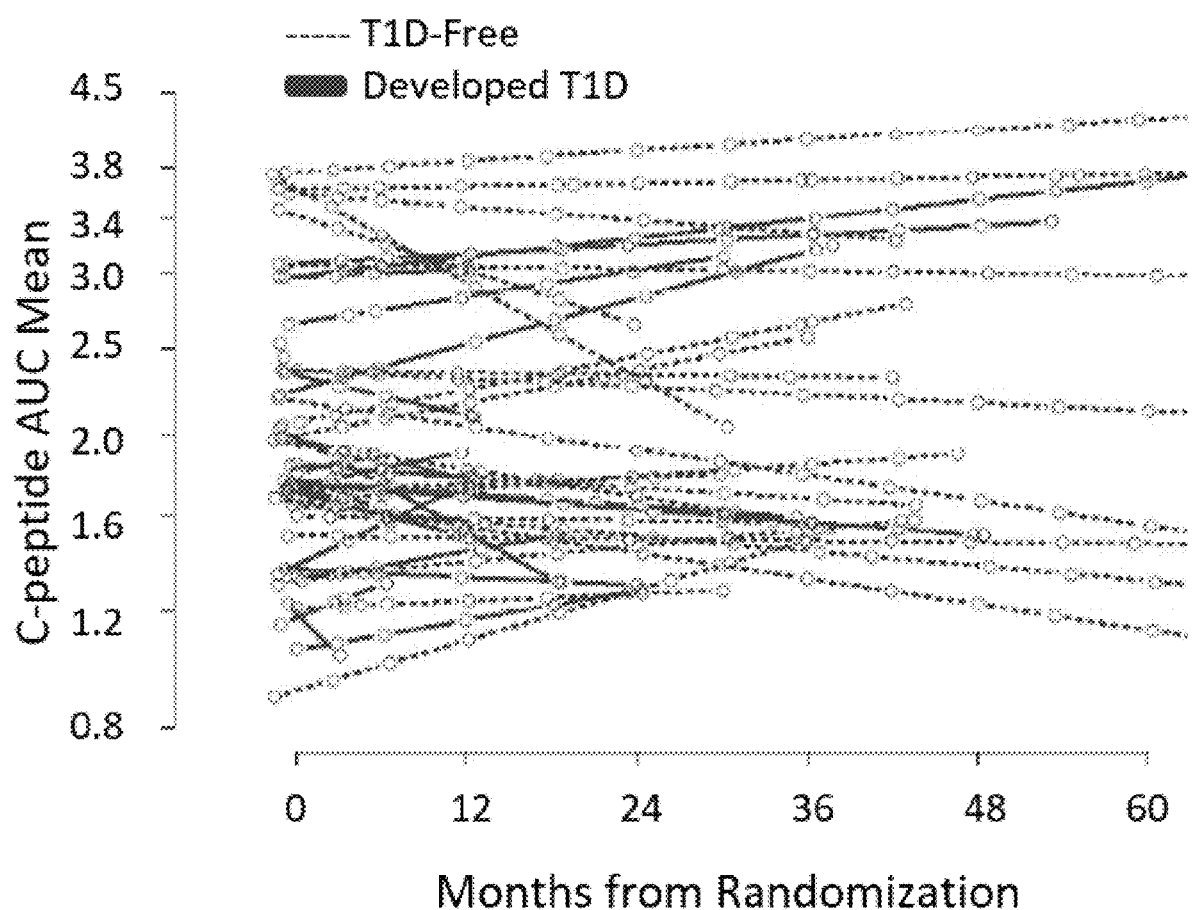
Figure 9C:
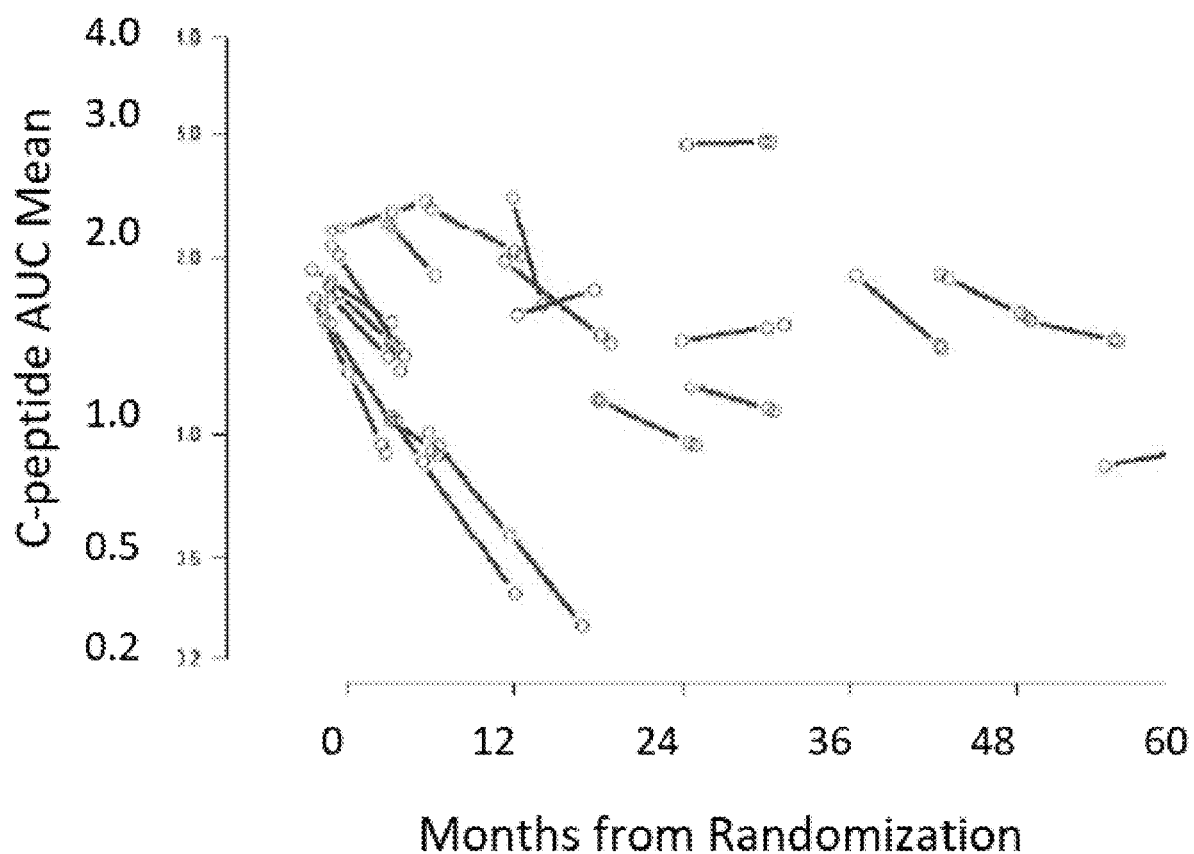
Figure 9E:
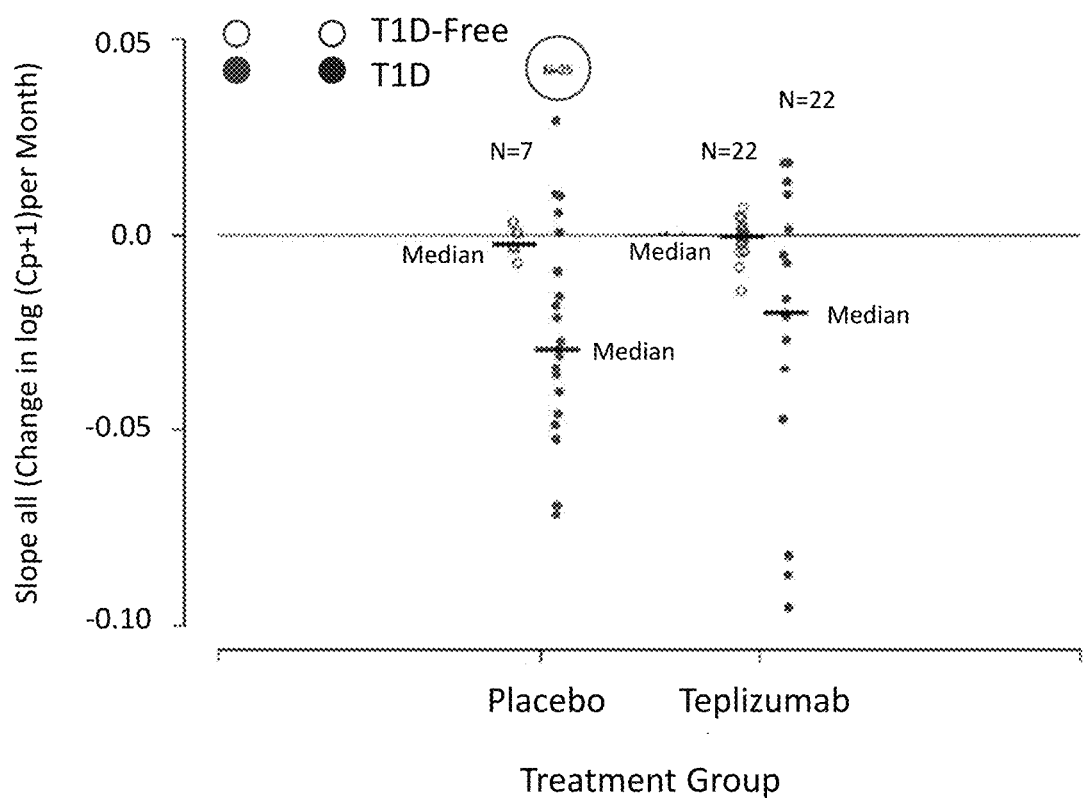

Preservation of C-peptide is maintained until the last 6 months preceding clinical diagnosis: To determine the duration of these metabolic effects, we analyzed the C-peptide trajectories (least-square lines) over the entire study period or until the 6 months prior to when the participant was diagnosed with T1D. (FIGS. 9A, 9B). With this analysis, C-peptide AUC continued to decline in the placebo group, with a median slope significantly less than 0 (median, IQR: −0.00382, −0.0107 to 0.000755, Wilcoxon 1-sample: p=0.04). The loss of C-peptide in the placebo group was even more pronounced in the 6 months between the penultimate and final OGTT (mean slope (IQR) of −0.0242 (−0.0469, −0.0041); significantly non-zero (Wilcoxon 1-sample: p=0.0001) (FIGS. 9C, 9E).

In contrast, the median slope for the teplizumab group until the end of the study period or until the 6 months prior to when the participant was diagnosed with T1D was not significantly different from 0 (mean (IQR): −0.000294 (−0.00372, 0.00304), Wilcoxon 1-sample: p=0.63) (FIG. 9B) and thus, less C-peptide AUC was lost over time compared to the placebo treated participants (Wilcoxon 2-sample: p=0.04). In the participants treated with teplizumab who were diagnosed with T1D, there was also a decline in the C-peptide AUC in the peridiagnostic period, but it was less pronounced than those in the placebo treatment arm who were diagnosed with T1D (mean slope (IQR): −0.0112, −0.0818, 0.0107), Wilcoxon 1-sample with a comparison to 0: p=0.09) (FIG. 9D) (Wilcoxon 2-sample comparing placebo and teplizumab slopes: p=0.06) (FIG. 9E). A difference in insulin sensitivity between the two treatment arms was not a likely explanation for these findings since the C-peptide AUC/glucose AUCs were similar in the teplizumab and placebo groups at the time of T1D diagnosis (p=0.23) (FIGS. 10A, 10B).

Figure 11A:
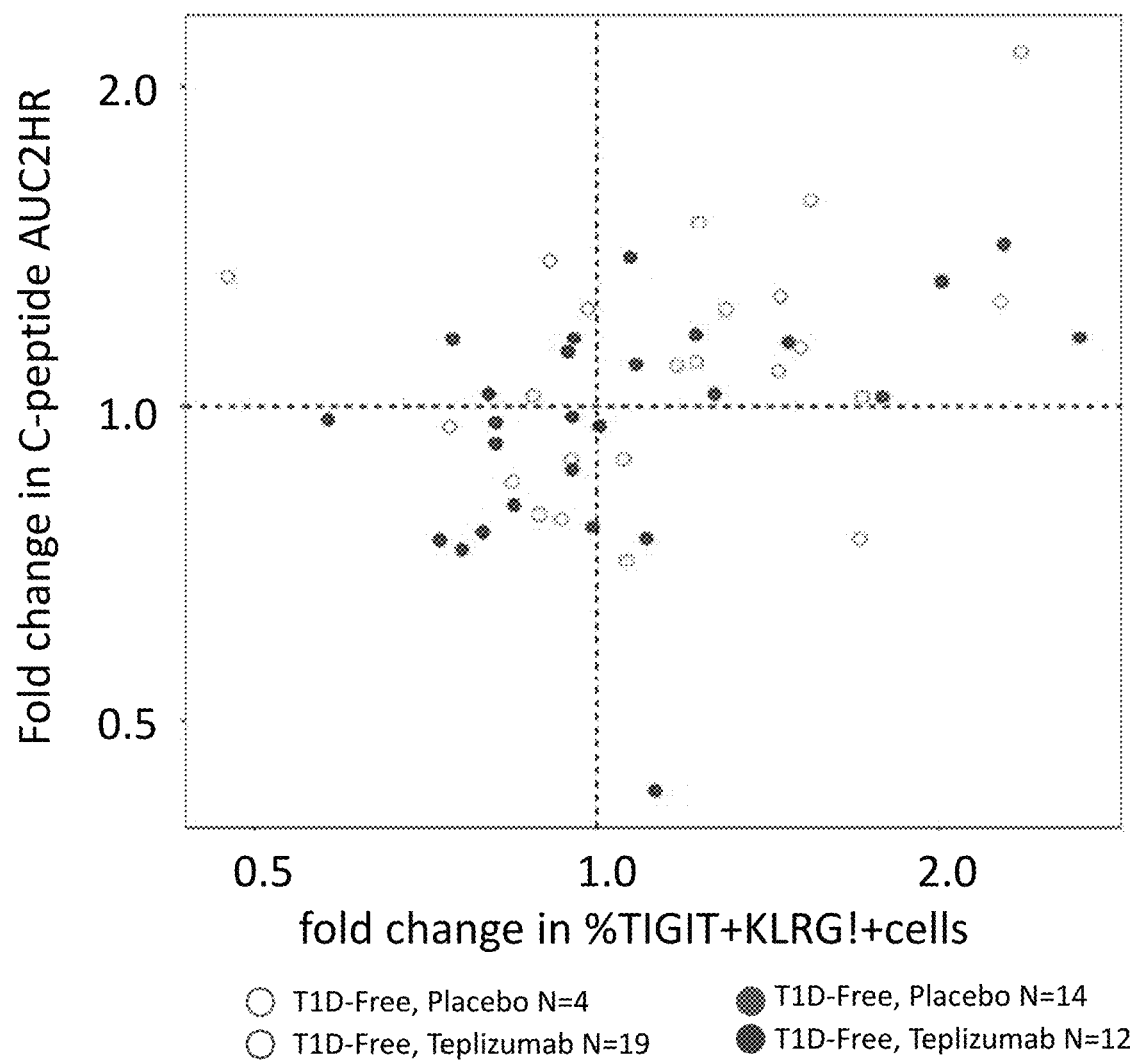
FIGS. 11A-11C show that functional changes in T cells are associated with improvements in metabolic function.

C-peptide responses correlate with increases in partially exhausted CD8+ T cells: We postulated that the rapid improvement in metabolic responses was related to the effects of teplizumab on T cells. We had previously described an increase in the frequency of memory CD8+ T cells with teplizumab treatment that we proposed were "partially exhausted" by expression of TIGIT and KLRG1+ (double positive cells), and a transcriptional activation/exhaustion signature that could be further reduced by ligation of TIGIT (23, 25, 26, 37, 38). Thus, we checked if their frequency was associated with C-peptide AUC during or shortly after the drug treatment period and whether they were functionally exhausted. We observed a significant correlation of the change in frequency of CD8+KLRG1+ TIGIT+ T cells with the fold changes in C-peptide AUC at month 3, 6, and 18 (Table 6). The changes in T cell subsets most likely preceded the changes in C-peptide and therefore, we also analyzed the fold changes in the double positive CD8+ T cells at month 3 and the fold changes in C-peptide at month 6. There was a significant association between these two parameters in the drug but not placebo treated participants. (p=0.014) (FIG. 11A).

TABLE 6

Pearson Correlations Between % Change in C-peptide and CD8+ T Cell Subpopulations

| CD8 Subsets | Month 3 | | Month 6 | | Month 18 | |
|---|---|---|---|---|---|---|
| | r | P | r | P | r | P |
| KLRG-1 + TIGIT+ of CD8 Central Memory | 0.429 | 0.016 | 0.433 | 0.01 | 0.463 | 0.011 |
| KLRG-1 + TIGIT+ of CD8 Effector Memory | 0.421 | 0.018 | 0.460 | 0.006 | 0.461 | 0.012 |

Figure 11B:
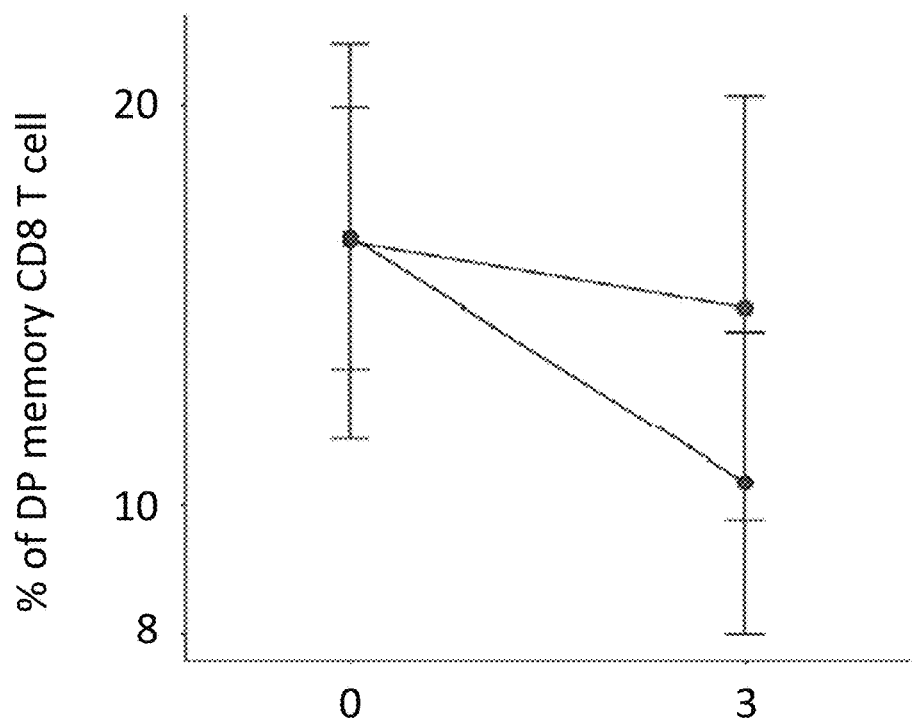
Figure 11C:
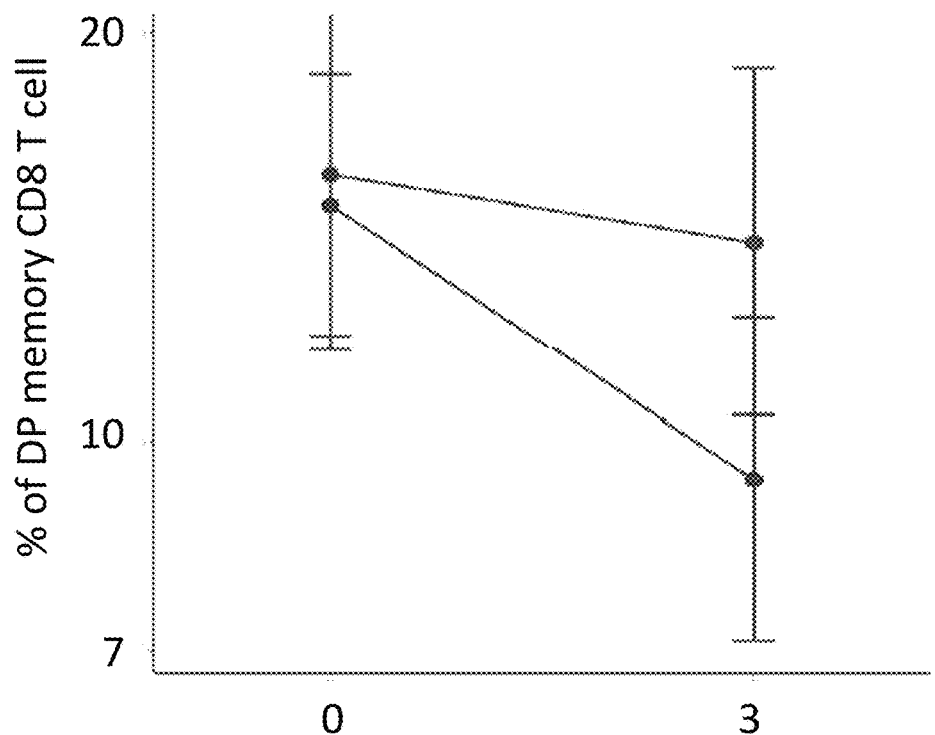
Figure 12:
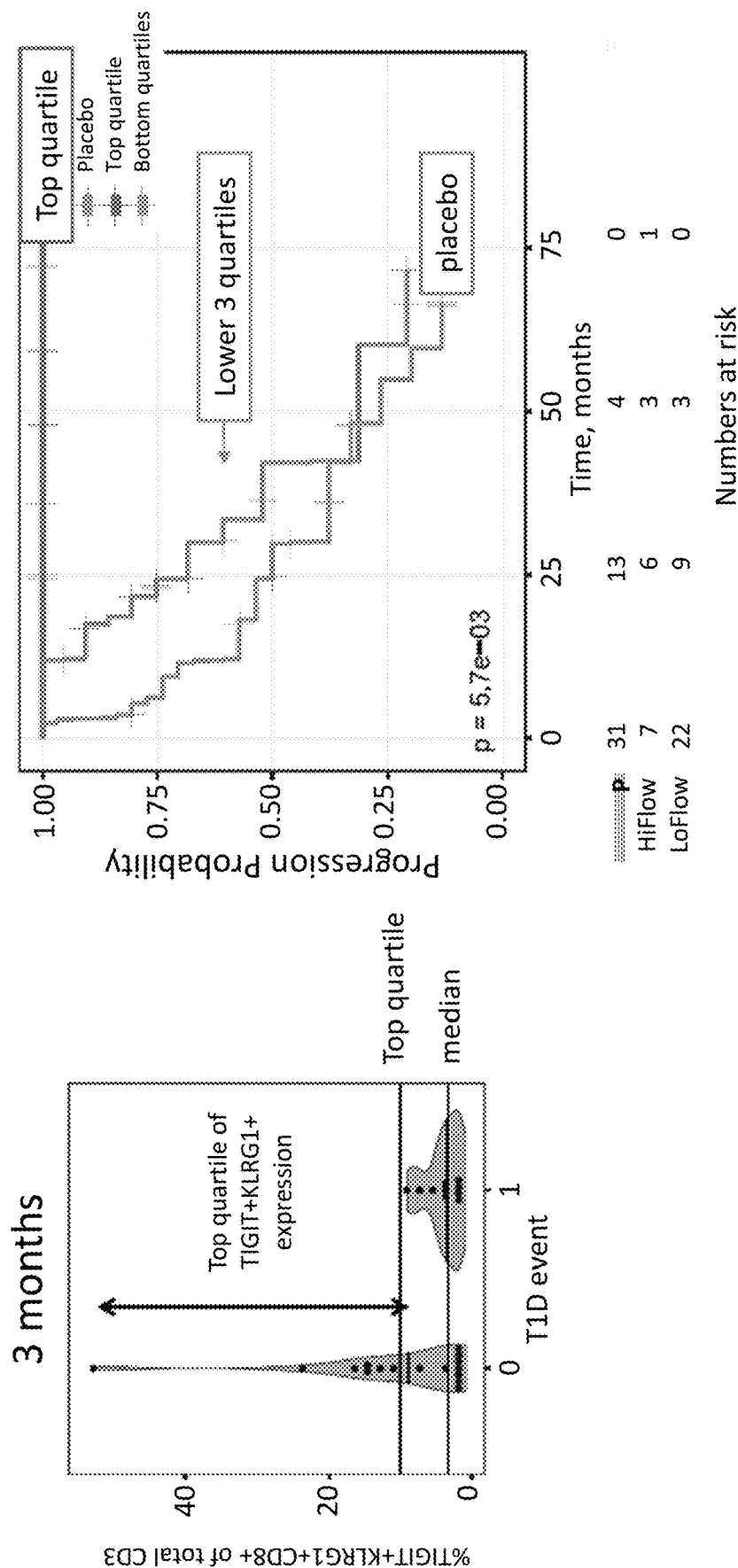
FIG. 12 shows teplizumab treated subjects with the best outcome have more TIGIT+KLRG1+CD8 T cells.
Figure 13:
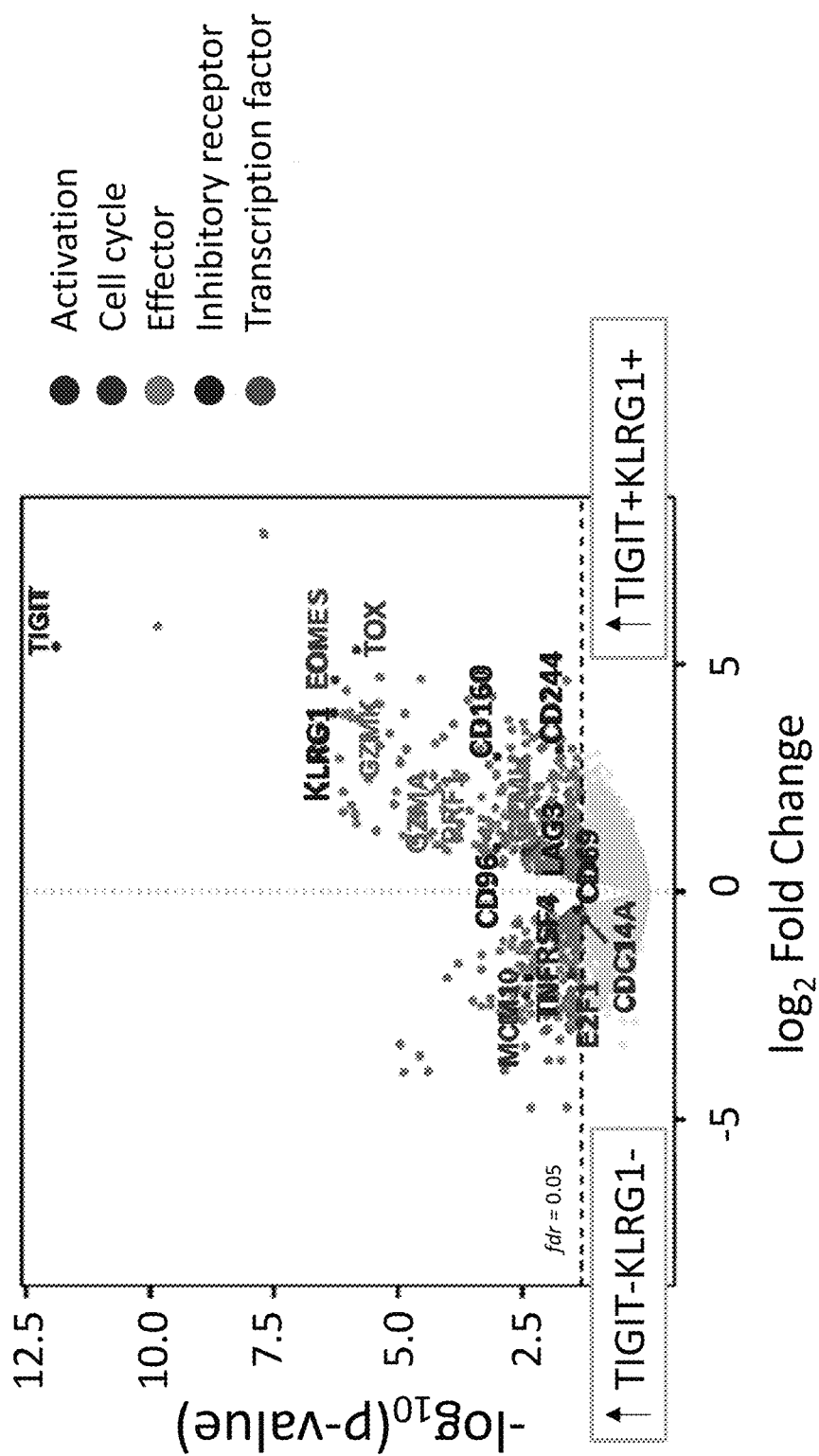
FIG. 13 and FIG. 14 show total TIGIT+KLRG1+CD8 T cells resemble exhausted cells.
Figure 14:
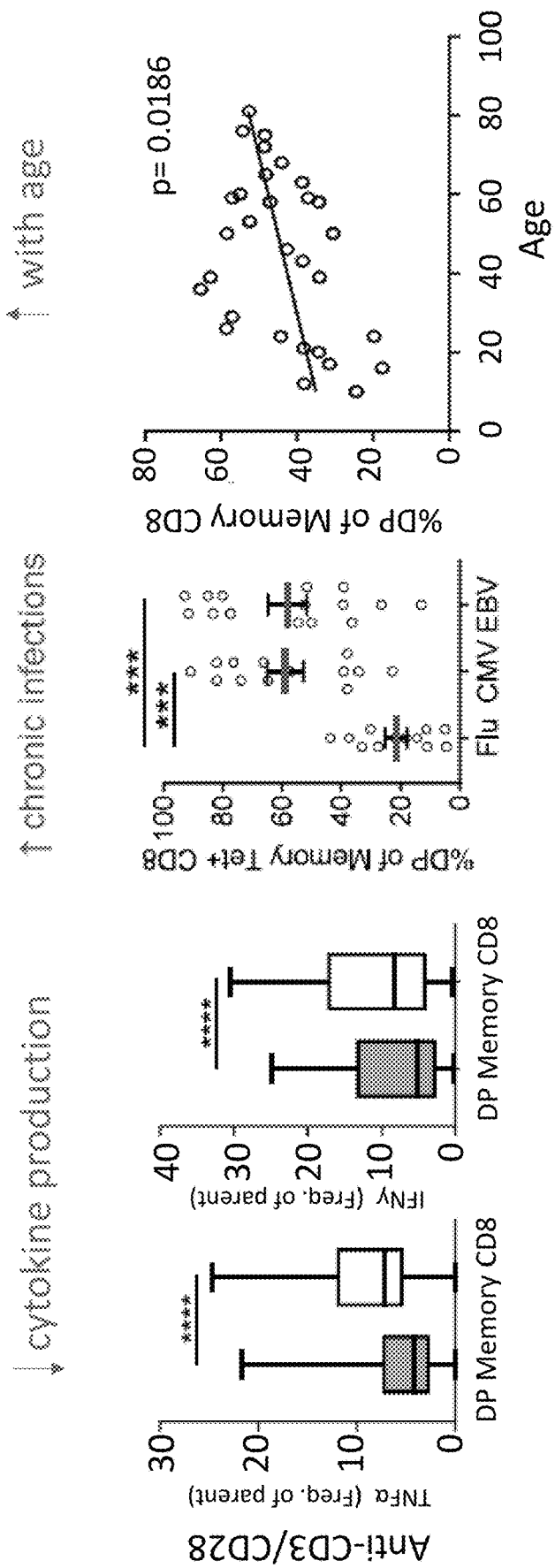
Figure 15:
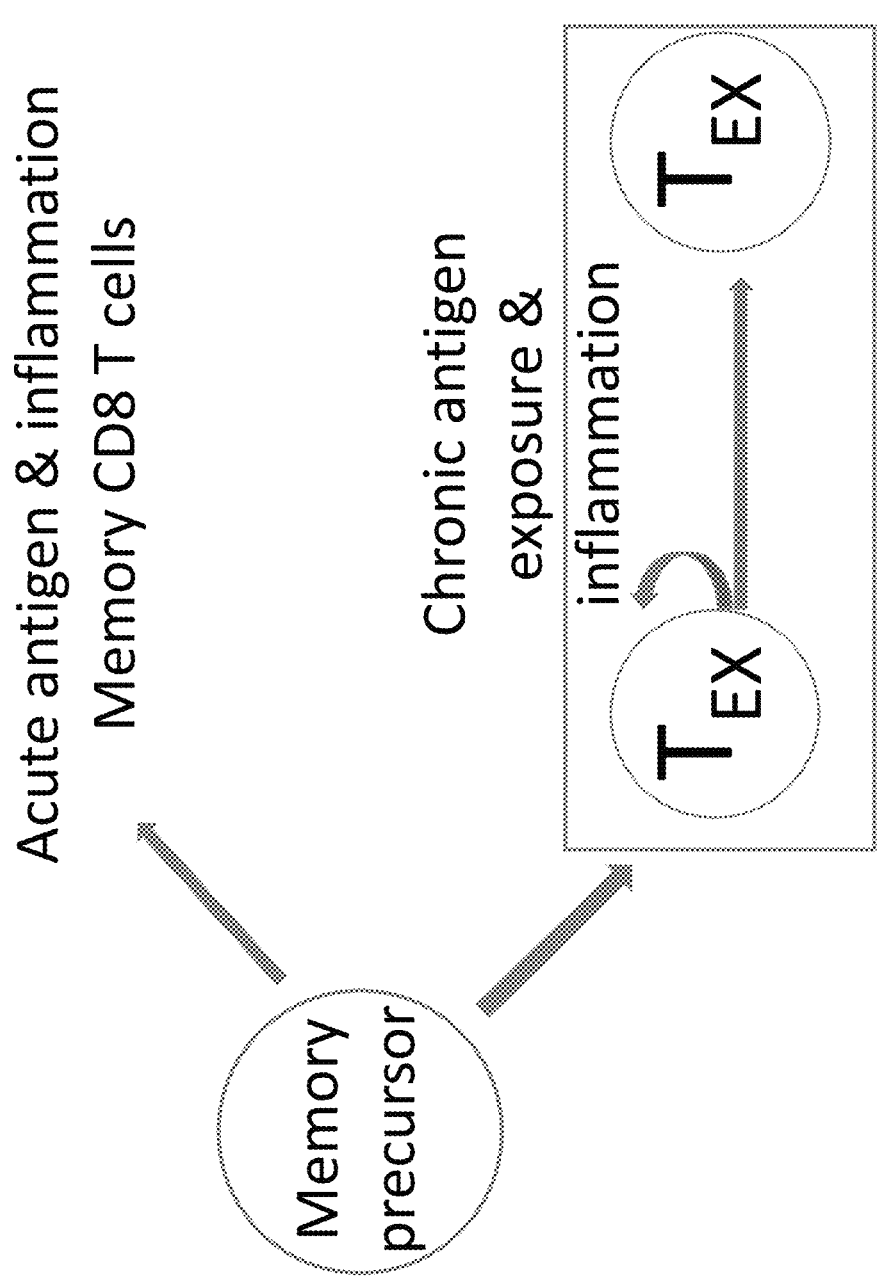
Figure 17:
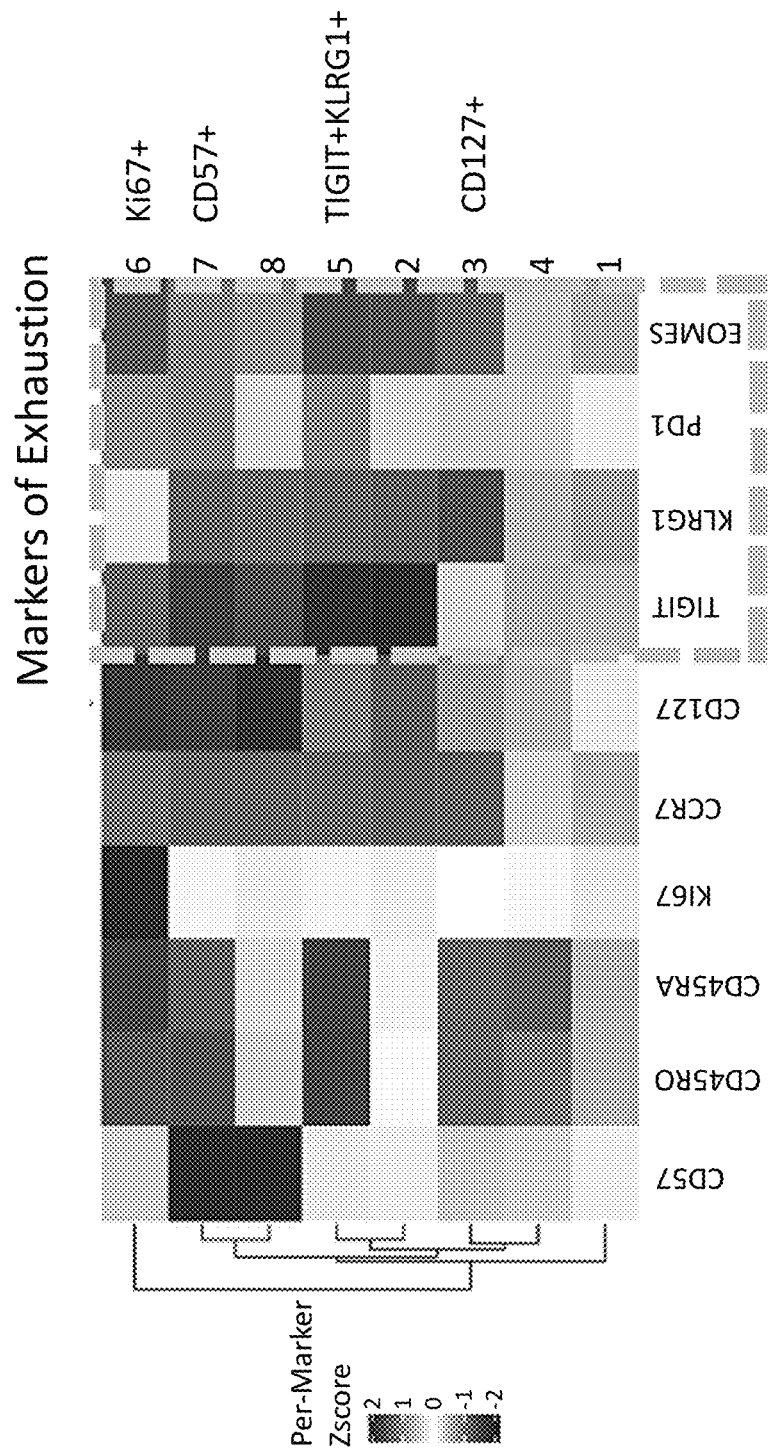
FIG. 17 shows TIGIT+KLRG1+ T cells are spread across much of the memory CD8 landscape in the teplizumab TrialNet Stage 2 trial.
Figure 18:
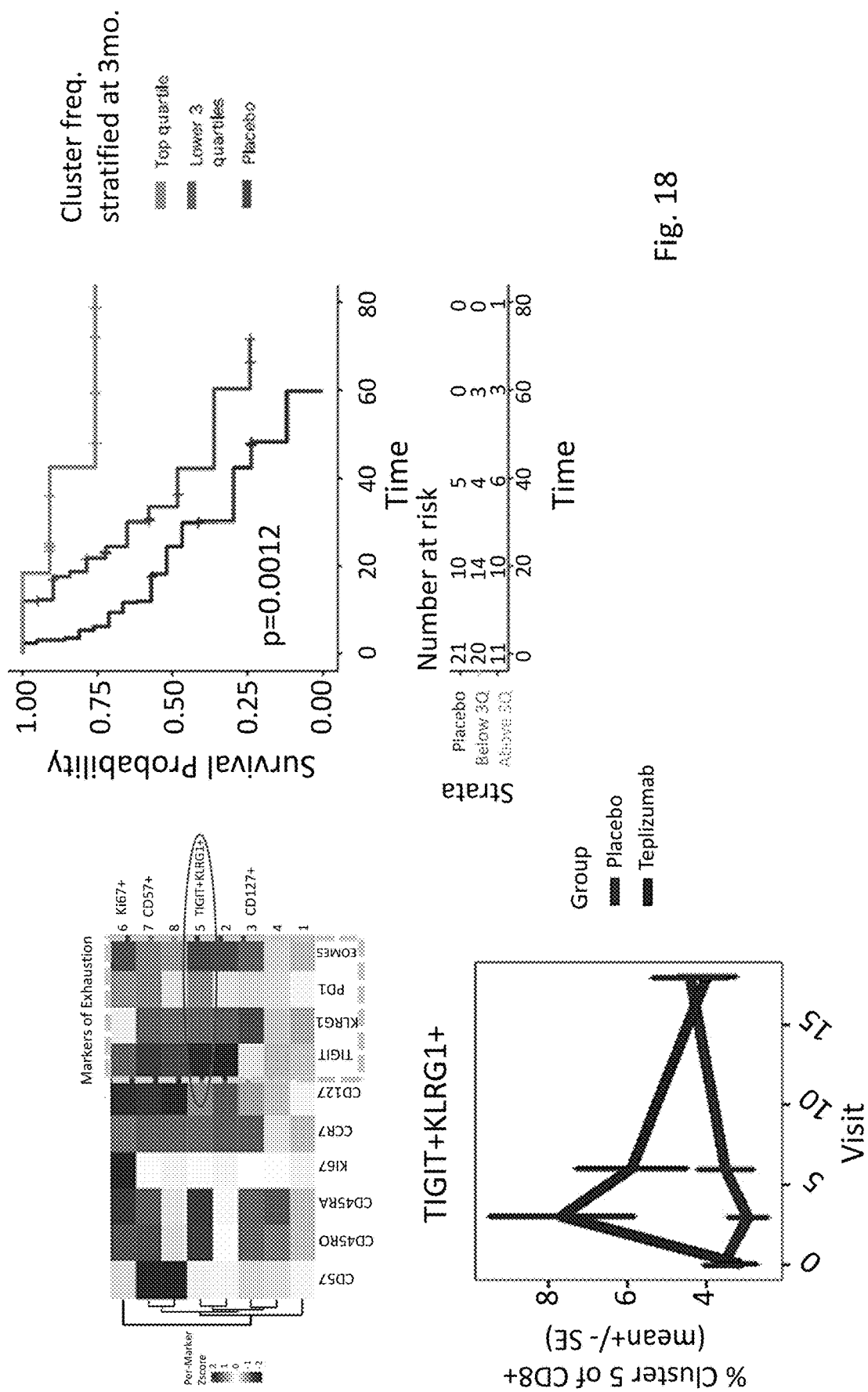
FIGS. 18-21 shows TIGIT+KLRG1+ subsets differ in response and outcome.
Figure 19:
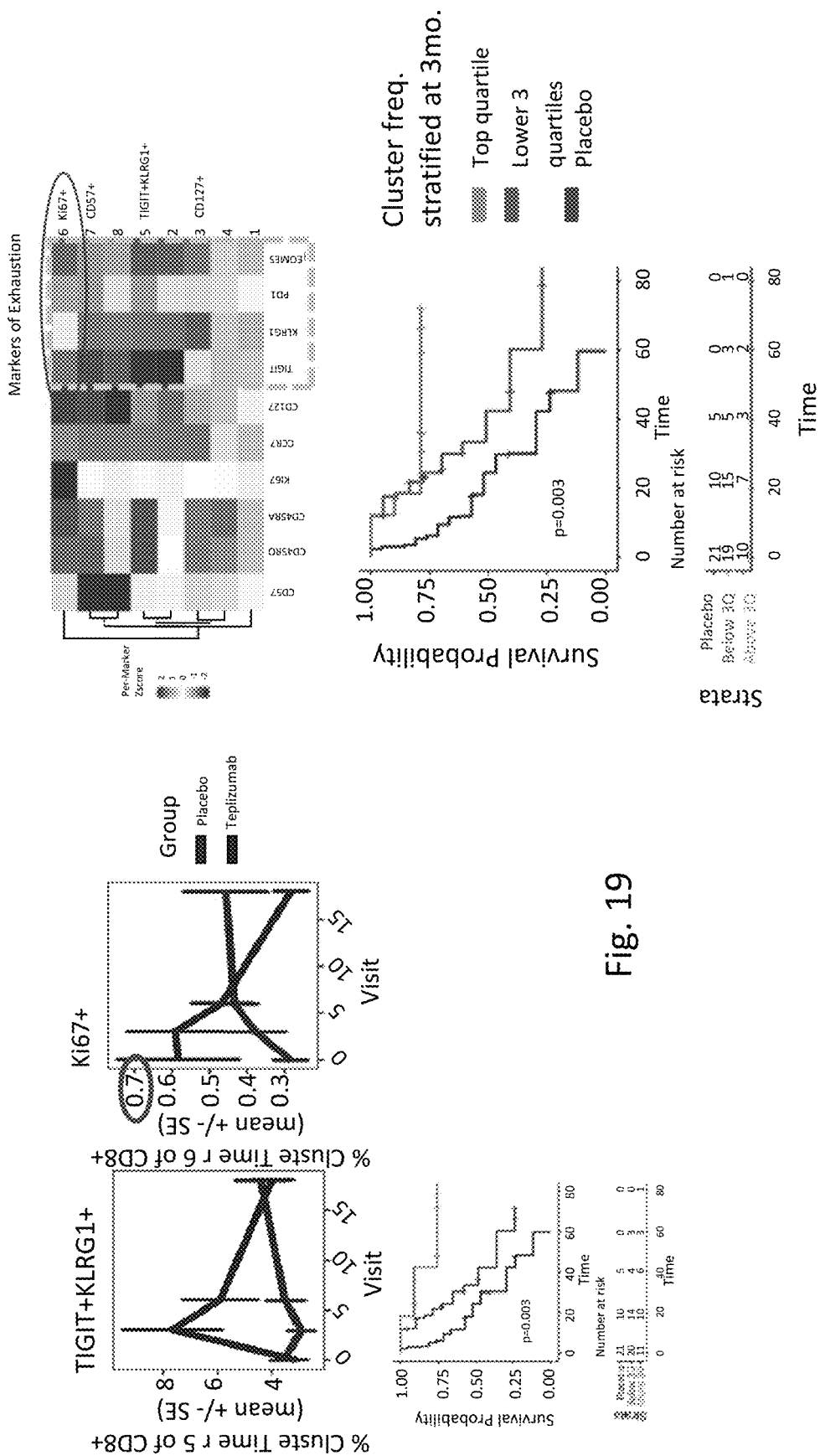
Figure 20:
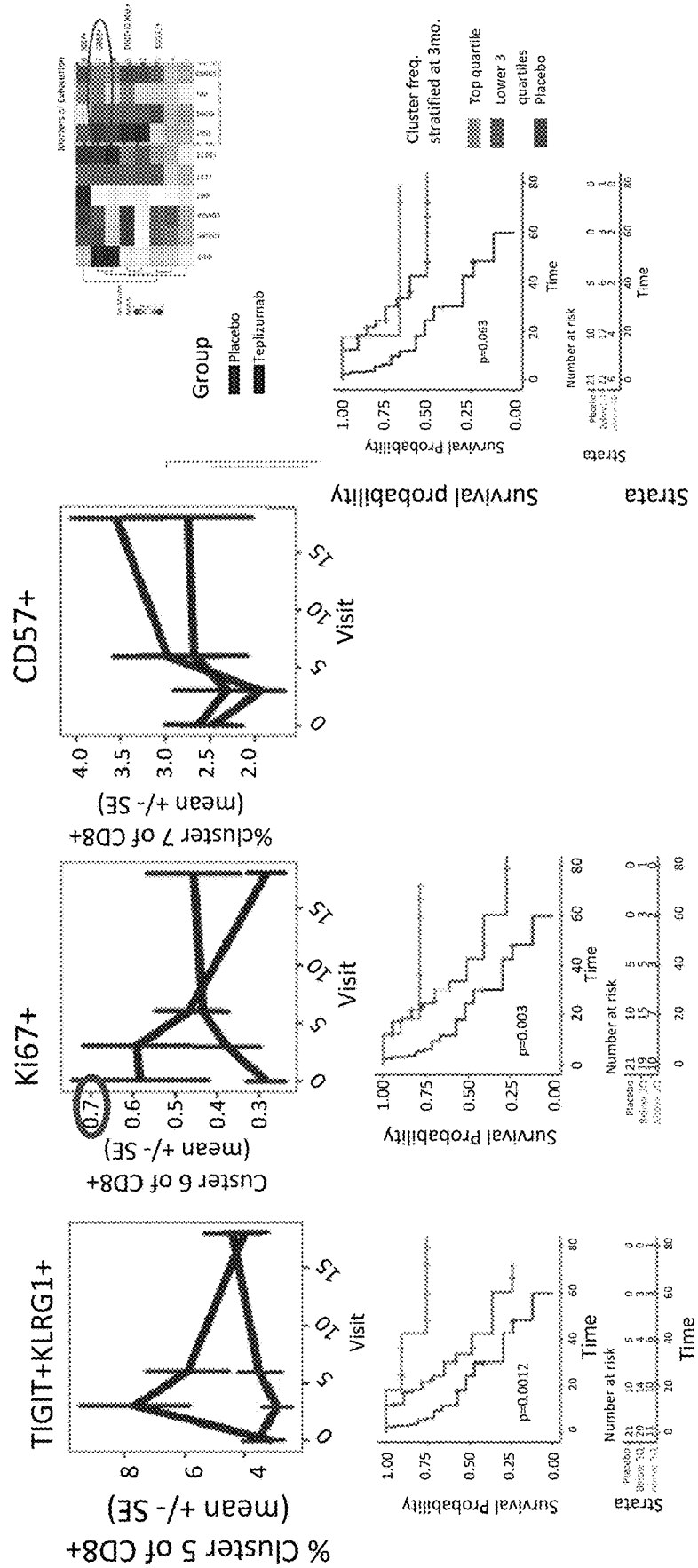
Figure 21:
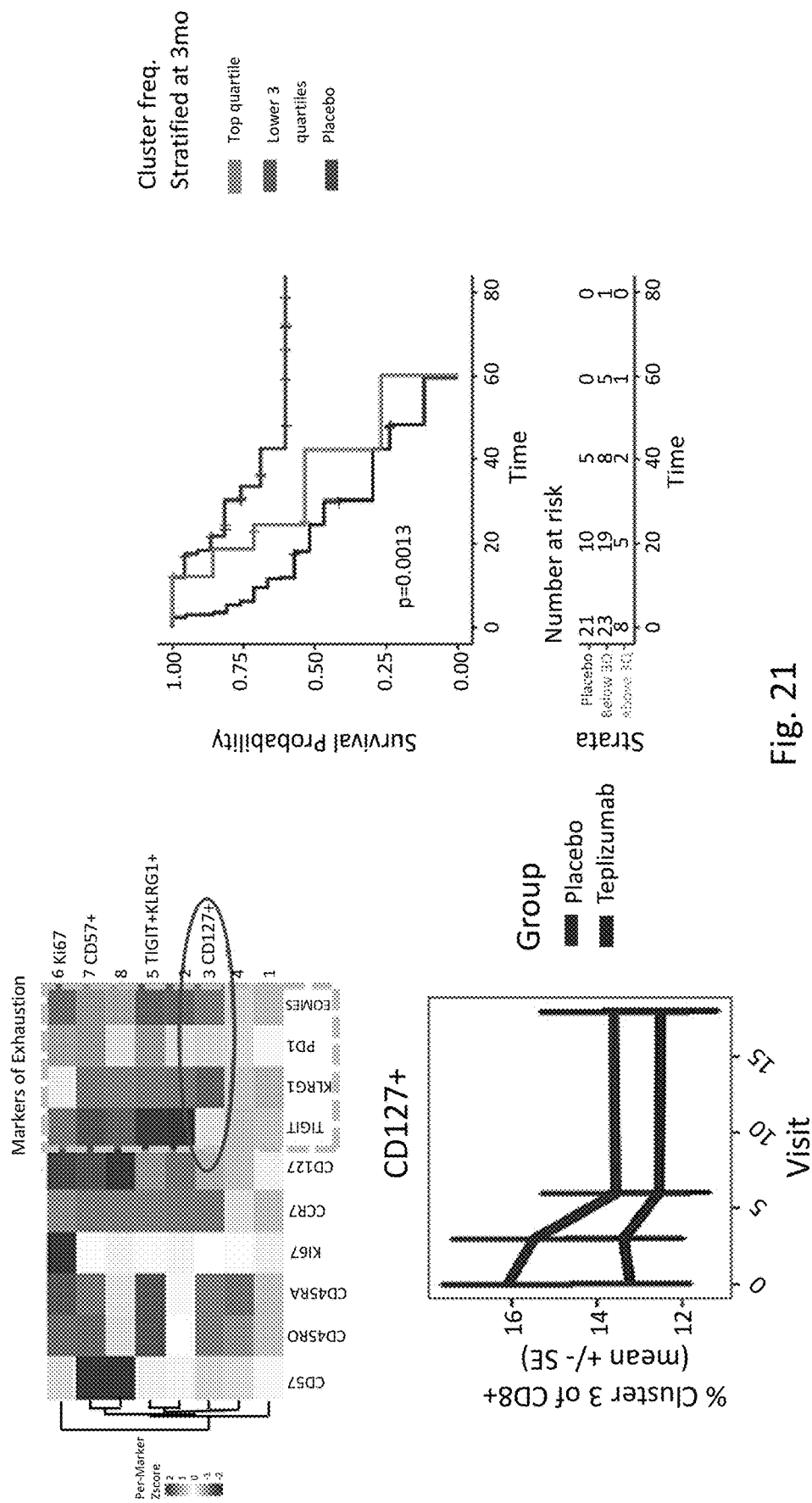
Figure 22:
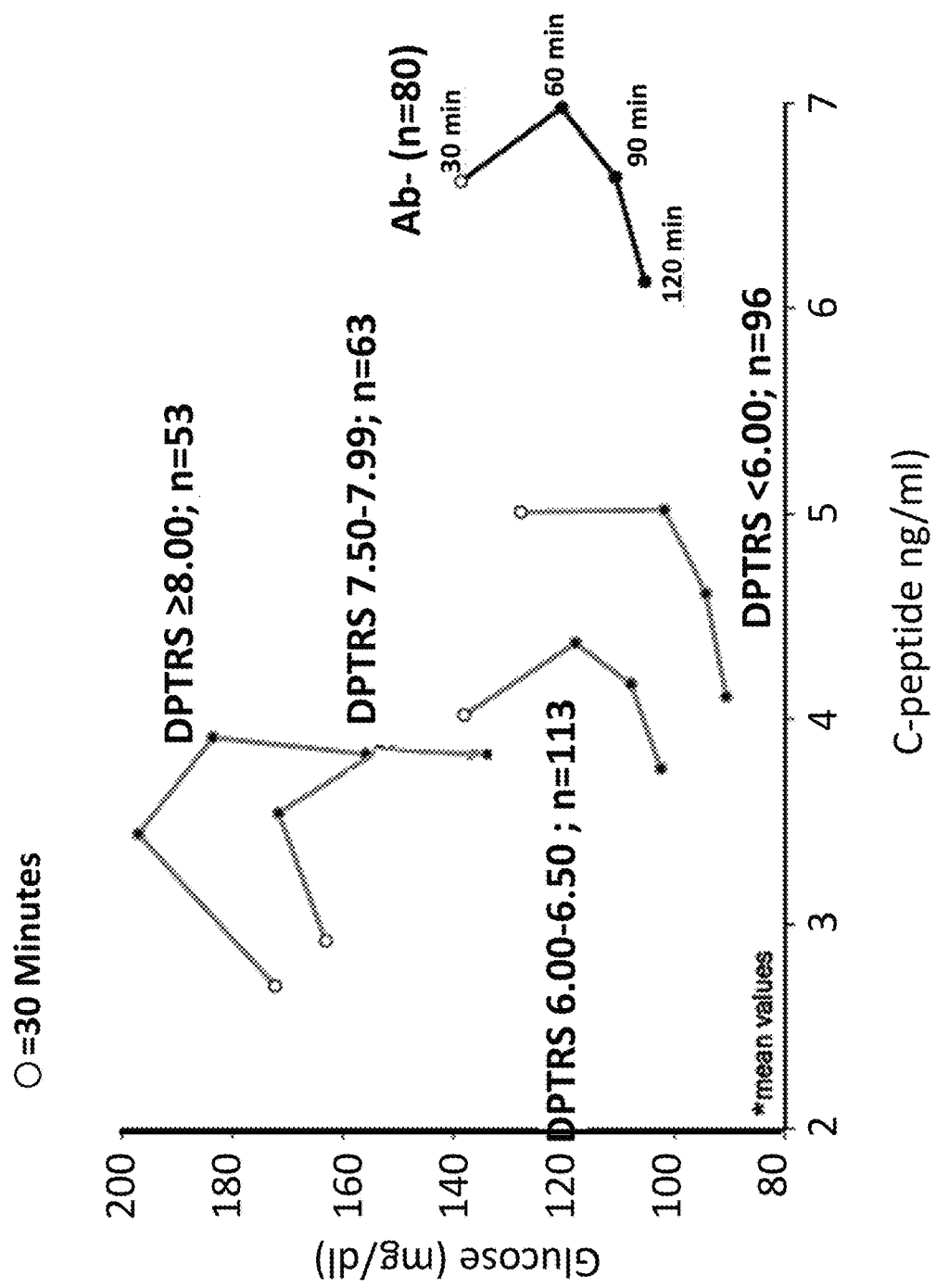
FIG. 22 shows OGTT patterns of 30 to 120 minute glucose and C-peptide.
Figure 23:
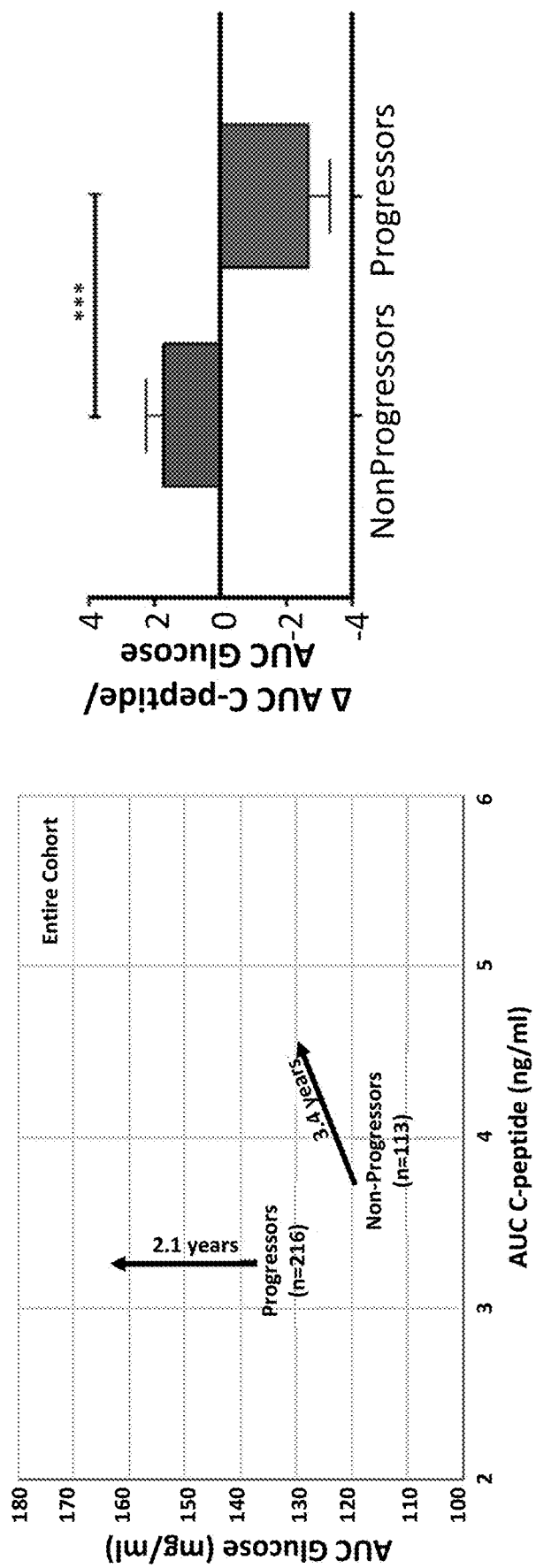
FIG. 23 shows 2D plots of mean glucose and C-peptide values identify distinct longitudinal OGTT patterns among "Progressors" and "NonProgressors" within DPT-1.
Figure 24:
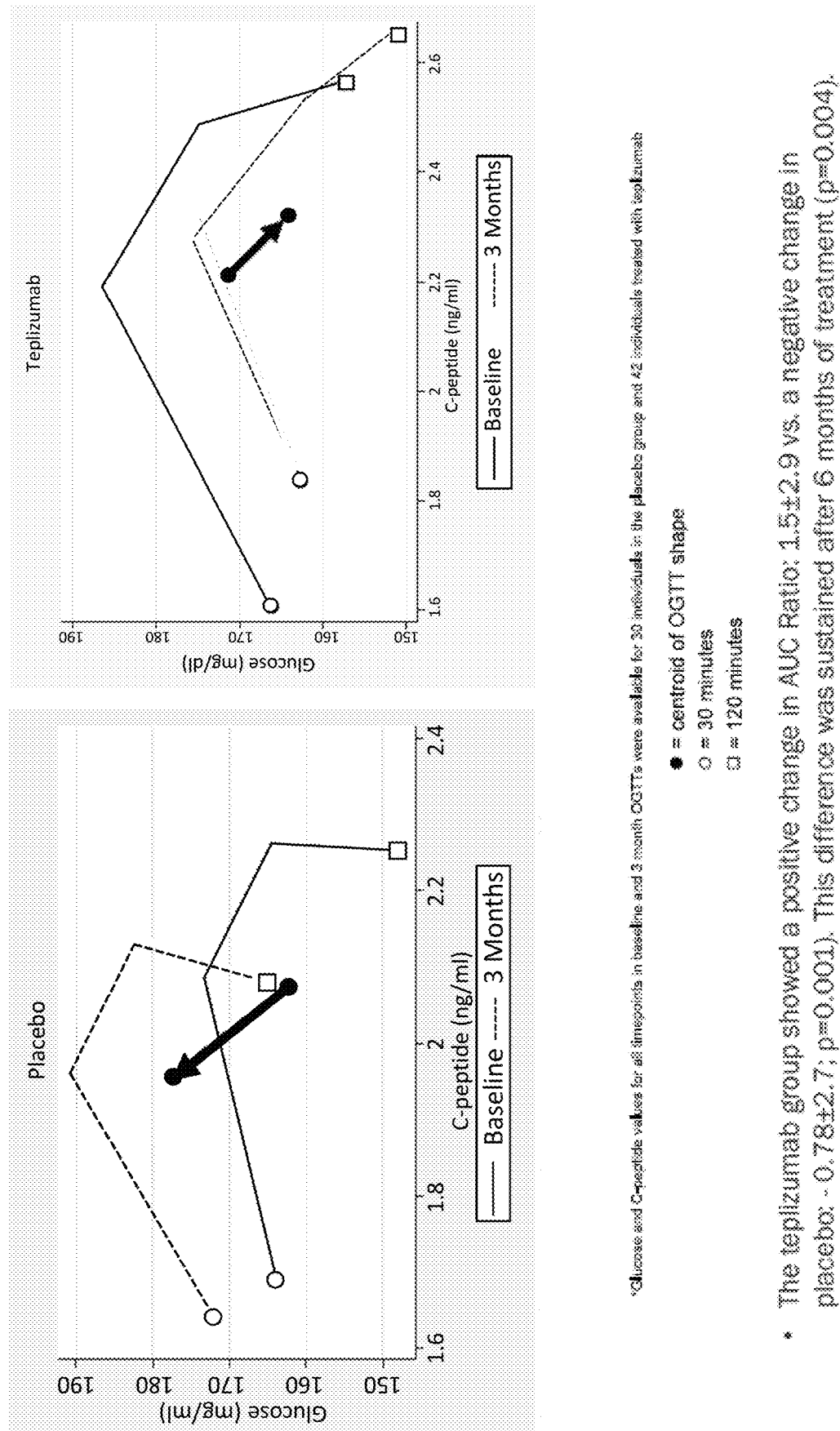
FIG. 24 shows 2D plots of mean glucose and C-peptide values for 30-120 minute OGTT timepoints show distinct patters at 3 month visit.

T cell exhaustion has been associated with reduced cytokine production following activation (39). We therefore measured intracellular cytokines after stimulation of PBMC with anti-CD3 and anti-CD28. Among the double positive CD8+ T cells the frequency of IFNγ-producing (p<0.0001, p=0.0004) and TNFα-producing cells (p<0.0001 for both) were decreased at 3 (FIGS. 11B, 11C) and 6 months respectively in the teplizumab but not placebo treated participants. In contrast, relative proportions of IFNγ and TNFα producing cells among the double positive memory CD8+ T cells remained stable in the placebo group at 3 and 6 months of follow-up. The fold decline in the frequency of the IFNγ and TNFα among the double positive CD8 memory cells between enrollment and month 3 were associated with the fold improvement in C-peptide between enrollment and month 6 (IFNγ: Pearson r=−0.29, p=0.164, TNFα: r=−0.39, p=0.056) (not shown).

Discussion

Studies of natural history cohorts have described changes in metabolic function during the progression to T1D in relatives at risk. Our successful intervention trial, with teplizumab, in the at-risk population has given us a unique opportunity to directly assess how changing immune cells can affect metabolic function and progression to the clinical diagnosis of T1D in relatives at high-risk. In this extended follow up we show that the effects of the single 14-day course of teplizumab treatment persists: The median time to diabetes in the teplizumab group was approximately 5 years compared to approximately 2 years in the placebo treated participants, with 50% of the teplizumab treated participants vs 22% of placebo treated participants not diagnosed with T1D. Eighteen percent of the teplizumab-treated participants vs 6 percent of the placebo treated participants were followed for more than 5 years and were not diagnosed. Importantly, this is the first study to show successful modulation of the progression of beta cell failure prior to the diagnosis of T1D with immune intervention.

Although the participants enrolled in the trial had not been diagnosed with T1D, teplizumab treatment improved beta cell function. The average OGTT glucose levels were lower and C-peptide responses higher with teplizumab treatment. There was improvement in total and early insulin secretion rates, which identifies a functional as well as a quantitative improvement in insulin release. The early secretion of insulin, a feature of normal beta cell function, was the most dramatically changed, indicating that the impaired "beta cell glucose sensitivity" that has been described in patients who progress to clinical diabetes was improved (34). The metabolic changes were associated with an increased frequency of TIGIT+KLRG1+ memory CD8+ T cells and a reduced secretion of cytokines (TNFα and IFNγ) that have been associated with pathology in T1D, indicating that the T cells had functional exhaustion (23, 25, 26, 37, 38).

Because the clinical trial was designed as a time-to-event protocol, the variable time in the study for each participant created a challenge in analyzing the metabolic responses during the study OGTTs. Hence, we used the average on-study C-peptide, glucose, and HbA1c AUCs which included all of the available data for each participant.

Although the time in the trial was not a significant determinant of the average C-peptide AUC, there were time-dependent metabolic effects of the drug treatment. Beta cell function was declining in the participants as they were enrolling in the TN10 trial. Indeed, in previous studies we found that the level of beta cell death was high among similarly high-risk individuals and other studies have documented beta cell dysfunction in the peridiagnosis period (35, 40, 41). This metabolic data together with the relatively short median time to diagnosis of T1D in the placebo group indicates that the screening methods utilized identified an active time of disease and individuals at very high risk for progression. Consistent with preclinical studies, the effects at this period of active disease support the concept that this intervention may be most effective when there is immune cell activation (42). The greatest increase in C-peptide occurred shortly after teplizumab treatment, followed by stabilization of beta cell function, whereas in the placebo group, beta cell function declined gradually over time. Consistent with prior reports, in those who developed clinical diabetes in both treatment arms, there was a precipitous decline in the stimulated C-peptide levels seen about 6 months prior to T1D onset (40).

Unexpectedly, we did not find a relationship between the average on-study glucose AUC and C-peptide AUC. Moreover, the outcomes of the OGTTs fluctuated even within individuals that did and did not develop T1D. Most likely this variability reflects the tenuous level of residual insulin production. Consistent with this, the OGTTs did not uniformly normalize in those who were not diagnosed with T1D. Minor changes, such as in the kinetics of insulin secretion or host factors may change the outcomes of the OGTT which are categorically classified based on levels of glycemia associated with long-term microvascular complications and not necessarily beta cell function or insulin secretion (43). These clinical outcomes are similar to the effects of anti-CD3 mAb in the NOD model of T1D, prior to the diagnosis of diabetes, in which insulin granularity was improved but beta cell mass did not recover to normal levels (44, 45). Further studies with metabolic clamps might improve our analysis of the metabolic function, but such studies were impractical in this clinical trial setting. These findings also suggest that combining teplizumab with a drug that improves beta cell function with complementary mechanisms may be valuable.

The factors that precipitated disease in the 6 months prior to clinical T1D diagnosis in both the treatment and placebo arms are not clear at this point. The similar relation between C-peptide and glucose in the two treatment arms among those who were diagnosed with T1D suggests that insulin insensitivity was not a precipitating factor for the diagnosis. Interestingly, even with progression to clinical diabetes, the decline in C-peptide tended to be less in the teplizumab vs placebo, which suggests that the effects of drug treatment on C-peptide may persist even during and potentially after the clinical diagnosis. There may be waning of the effects of the anti-CD3 antibody on immune cells which we identified previously by tracking the CD8 memory double positive cells (23). Other observations in the field show that progression to clinical diabetes is associated with acquisition of effector T cell function, but it is possible that in this setting restored effector function may involve waning of the immune effects of teplizumab or even new or regenerated pathologic T cells repopulating the repertoire after the single course of drug. The median age at the time of treatment in the TN10 study was 13.9 years, and in young children, the thymic output of T cells may be ongoing. In other studies of the long term outcomes of patients treated with teplizumab, there was an increase frequency of Programmed Cell Death Protein 1 (PD-1)+ memory CD8+ T cells in responders compared to non-responders and controls suggesting that changes in the phenotype and function of the CD8+ memory compartment may occur over time (46). Ongoing work tracking TCRs and single cell analyses will help to address these hypotheses and may suggest agents that could be used to extend the diabetes-free period possibly by blocking pathways needed for T-effector expansion (47).

There are limitations to our studies. The number of subjects was relatively small, and the study was powered to detect differences in diabetes incidence rather than changes in C-peptide AUC, insulin secretion, and immune function. Additionally, the time-to-event design of the original study had some important implications for the analyses included here. We did not have OGTT analyses for most individuals after diagnosis of T1D which limited our ability to compare OGTT data between all members of placebo and teplizumab groups over the same time period, particularly for the placebo group, which exhibited more rapid progression to diabetes. The time-to-event design also limited our ability to compare the relationship between metabolic endpoints and T1D progression, as some individuals included in the study that did not progress to diabetes may ultimately develop T1D. Furthermore, given prior results showing teplizumab treatment preserved C-peptide in patients with recent-onset T1D (19-25), positive effects on C-peptide might also be expected to occur amongst individuals that developed diabetes during this study. Participants from both arms of the trial were enrolled in the TrialNet LIFT study, which performs longitudinal metabolic testing in participants who have been diagnosed with T1D (13).

In summary, we show extended delay in progression to T1D in at-risk subjects treated with teplizumab. Teplizumab treatment changed the biologic course of the disease by enhancing beta cell function reflected by the quantitative and qualitative improvements in insulin secretion. These changes were associated with modulation of the frequency and function of memory CD8+ T cells. The pronounced early efficacy of the drug followed by stabilization of beta cell function also suggests that repeated treatment with teplizumab or the addition of other complimentary agents at key timepoints in the clinical course may be valuable to extend the delay or even prevent the diagnosis of T1D. Finally, our findings have implications for other autoimmune diseases by showing how immune intervention can change the pathobiology even prior to disease diagnosis and lead to a clinically significant outcome.

Materials and Methods

Trial Design

The design of this phase 2, randomized, placebo-controlled, double-blind trial (NCT01030861) has previously been reported (26). Institutional-review-board approval was obtained at each participating site. The participants, their parents, or both provided written informed consent or assent before trial entry. The participants were identified through the TrialNet Pathway to Prevention study (TN01) (14, 48). In that study, OGTTs were performed at approximately 6-month intervals in islet autoantibody positive individuals (including anti-glutamic acid decarboxylase 65, micro insulin, anti-islet antigen 2, anti-zinc transporter 8, and/or islet-cell antibodies), and the glucose results from these tests were used to identify eligibility for the anti-CD3 prevention trial (TN10) and were used in this data analysis. Islet autoantibody testing, HLA genotyping, and OGTT testing were performed as previously described (4, 49).

Briefly, eligibility criteria included age>=8 years at randomization, history of a relative with type 1 diabetes, positive titers for two or more islet autoantibodies, and dysglycemia on OGTT (fasting glucose 110-125 mg/dL (6.1-6.9 mmol/L), a 2-hour postprandial plasma glucose level of >=140 mg/dL (7.8 mmol/L) and <200 mg/dL (11.1 mmol/L), or an intervening postprandial glucose level at 30, 60, or 90 minutes of >200 mg/dL. For participants who did not have a hemoglobin A1c available at the baseline visit, values obtained within the 3 months before treatment were utilized.

Participants were randomly assigned to teplizumab or saline and treated with a 14-day outpatient course administered as an IV infusion in a clinical research center. Teplizumab was dosed at 51 µg/m$^2$ on day 0, 103 µg/m$^2$ on day 1, 207 µg/m$^2$ on day 2, 413 µg/m$^2$ on day 3, followed by a dose of 826 µg/m$^2$ on days 4 through 13. OGTTs were performed 3 months and 6 months after the infusions and every 6 months thereafter. Random screening glucose levels were evaluated at 3-month intervals, and an OGTT was performed if the random glucose level was >200 mg/dL (11.1 mmol/). T1D was diagnosed using ADA criteria during an OGTT but only after the diabetic OGTT was sequentially confirmed. The date of diagnosis was identified as the time of the first of the 2 diagnostic tests (50). Six participants were clinically diagnosed with T1D outside of OGTT monitoring. The original trial end date was May 2019. Participants who had not been diagnosed with T1D were transferred into the TrialNet Pathway to Prevention Natural History study (TN01) for follow up OGTT monitoring. Data from that follow up, between July 2011 and March 2020 are included in this analysis. Participants that did develop T1D were offered enrollment in TrialNet's Long Term Investigational Follow-up (LIFT) study for continued metabolic follow-up.

Metabolic Analyses

OGTT C-peptide and glucose values were tested by Northwest Lipids Research Laboratories using the TOSOH and Roche C-peptide and glucose immunoassays, respectively. OGTT results were assigned to the nearest study visit timepoint (within 3 months of the official timepoint assignment. OGTT results were classified as normal, dysglycemic, or diabetic based on above definitions used for study entry. The baseline OGTT was the study at the time or immediately prior to randomization.

Area under the curve (AUC) values for ISR, C-peptide, and glucose were calculated using the trapezoidal rule. The on-study AUC means for C-peptide, glucose, and HbA1c were calculated by multiplying the AUC means for each OGTT visit and the visit intervals in days (as the trapezoidal base) to calculate a total study AUC, and then dividing by the days from the first to the last OGTT (confirmatory diabetic OGTT if developed T1D). Insulin secretory rates (ISRs) were calculated using the Chronobiological Series Analyzer (CSA) software, which uses a 2-compartment model for hormone clearance and standard kinetic parameters for C-peptide (51-53). ISR calculations were performed using participant OGTT C-peptide and glucose values, as well as age, sex, height, and weight. The insulin secretion was divided into the amount (pmol) secreted over the 2-hour OGTT or in the first or second hour of the test.

Flow Cytometry Analysis

Peripheral blood mononuclear cells (PBMC) were processed and stored at the NIDDK repository. Cryopreserved vials of PBMC were sent to ITN Core laboratory at Benaroya Research Institute for analysis by flow cytometry with antibody panels shown in Tables 7 and 8. T-cell phenotyping was performed on thawed PBMC and the frequency of CD45RO+CD8+ T-cells that were TIGIT+KLRG1+CD57− was determined as described previously (54). Intracellular cytokine expression was measured after 6 hours with stimulation of PBMC by plate-bound anti-CD3 (1 µg/ml) and soluble anti-CD28 (10 µg/ml) in the presence of equimolar amounts of Golgi-stop. The frequency of TIGIT+KLRG1+ CD8+ memory (CD45RA−) T cells that produce IFNγ or TNFα were determined at baseline and month 3.

TABLE 7

T cell phenotype flow cytometry panel

| Markers | Format | Clone | Vendor* |
|---|---|---|---|
| CD56 | BUV395 | NCAM16.2 | BD |
| CD45RA | BUV737 | MN I | BD |
| Ki67 | BV421 | Ki-67 | BL |
| CCR7 | BV510 | G0434H7 | BL |
| CD3 | BV605 | OKT3 | BL |
| PD1 | BV650 | EH12.2H7 | BL |
| CD127 | BV711 | A019D5 | BL |
| CD-45R0 | BV786 | UCHLI | BD |
| CD4 | BB515 | RPA-T4 | BD |
| Eomes | PE | WD1928 | eBio |
| FoxP3 | PE-CF594 | 259D/C7 | BD |
| KLRG1 | PE-Vio770 | REA261 | Miltenyi |
| TIGIT | APC | MBSA43 | eBio |
| CD8 | Ax700 | SKI | BL |
| CDS7 | APC-Vio770 | REA769 | Miltenyi |
| L/D | BUV496 | | |

*BL = Biolegend, BD = Becton Dickinson, Miltenyi = Miltenyi biotech, eBio = eBioscience

TABLE 8

Intracellular cytokine staining flow cytometry panel.

| Markers | Format | Clone | Vendor* |
|---|---|---|---|
| IL-17 | BV421 | BL168 | BL |
| CD45RA | BV605 | HI100 | BL |
| GrzmB | BV510 | GB11 | BD |
| PD-1 | BV650 | EH12.2H7 | BL |
| CD3 | BUV737 | UCHT1 | BD |
| TNFa | APC | MAb11 | BL |
| CD127 | BV785 | A019D5 | BL |
| CD4 | Ax 700 | RPA-T4 | BL |
| IFNg | BV711 | B27 | BD |
| FoxP3 | PE-CF594 | 259D/C7 | BD |
| KLRG1 | FITC | SA231A2 | BL |
| TIGIT | PE-Cy7 | A15153G | BL |
| CD8 | BUV395 | RPA-T8 | BD |
| IL-2 | BB700 | MQ1-17H12 | BD |
| L/D | BUV496 | | |

*BL = Biolegend, BD = Becton Dickinson, Miltenyi = Miltenyi biotech, eBio = eBioscience Instrument standardization was performed using 8 peak rainbow calibration beads (Spherotech, Lake Forest, IL) adjusting PMT voltages for consistent 7$^{th}$ peak mean fluorescent intensities. All samples from the same subject were run on the same day, and an internal control arm from the same subject was run each week. Sample acquisition was performed as previously described on an LSR-Fortessa (BD Biosciences) with FACS Diva software and analyzed with FlowJo software version 9.5 (Tree Star, Ashland, OR) (54). The quadrants were placed based on staining controls. Gated populations with <100 events were excluded from analysis.

Statistical Analysis

The original trial was designed as a time-to-event analysis and therefore participants who were diagnosed with T1D were not followed further in that study. The impact ofteplizumab treatment on incidence of type 1 diabetes following enrollment was performed using a Cox proportional hazards model. For this analysis, metabolic parameters over the entire period of the trial included OGTT data in the visit immediately prior to and all OGTT data after study drug treatment (confirmatory diabetic OGTT for individuals diagnosed with diabetes, or last available OGTT for those remaining diabetes free). Slopes for changes in glucose and C-peptide prior to and after enrollment were calculated using linear regression analysis of available OGTT visit data for specified intervals. An impact of treatment on each endpoint was determined by fitting results to an ANCOVA model, with age, baseline value, and treatment group included as covariates. Wald tests were used to determine if covariates significantly impacted the model.

Estimated slopes for changes in the insulin secretion rates were also calculated for each subject based on changes before treatment (time points up to 6 months prior to baseline) and for after initiation of treatment (time points up to 6 months after baseline) using linear regression models as well as mixed models for repeated measures. Insulin secretion rates were calculated across the overall 2-hour interval as well as specifically for the first hour and the second hour intervals of the OGTTs. Differences in these slopes before vs. after treatment were compared using Wilcoxon signed rank tests within and across treatment arms. Differences and percent changes in these slopes before vs. after treatment were also evaluated using a generalized linear model to assess the influence of treatment arm.

Flow cytometry data were log-transformed for statistical analysis. Pearson's correlation coefficient was calculated to determine associations between fold changes in C-peptide AUC and frequency of TIGIT+KLRG1+CD8+ memory T cells. The frequency of TIGIT+KLRG1+CD8+ memory T cells producing IFNγ or TNFα were analyzed by paired t-test.

Example 2: Anti-CD3 Antibody (Teplizumab), Delays Type 1 Diabetes Onset in Stage 2 Type 1 Diabetes As shown in FIGS. 12-21, in at-risk (Stage 2) relatives of T1D patients, a single course of teplizumab (as described in Example 1) increased TIGIT+KLRG1+ exhausted CD8+ T cells correlating with delay/prevention of clinical T1D. Surprisingly, no conversion to clinical T1D was observed in subjects with >10% exhausted CD8+ T cells (% in all CD3+ T cells, i.e., top quartile of exhausted T cells) in the circulation 3 months post teplizumab treatment (p=0.005). Subjects with more TIGIT+KLRG1+CD8+ T cells 3 months following treatment with teplizumab responded the best.

These cells may express other markers of exhaustion such as PD1 and Eomes. These cells may be partly exhausted, and produce lower levels of inflammatory cytokines than in placebo-treated patients.

TIGIT+KLRG1+CD8 T Cells are not homogeneous, but instead, vary across individuals in number and function. Rather than being uniformly exhausted, TIGIT+KLRG1+ cells are a mixture of less- and more-functional populations.

We also observed a decrease in CD8+ T cells expressing the proliferation markers Ki67 and CD57 compared to placebo, consistent with the reduction of effector T cells and increase in exhausted T cells. The decrease in Ki67 and CD57 correlates with clinical response (p=0.003 and p=0.006 respectively). CD127+CD8 T cells are associated with worse outcome.

Thus, in some embodiments, teplizumab can be dosed repeatedly and used in combinations to increase the generation/maintenance of exhausted T cells and improve response and outcomes.

In some embodiments, teplizumab responsiveness can be predicted before dosing or shortly after dosing by determination of exhausted T cells.

Example 3: 2D Analysis of Glucose and C-Peptide Shows a Teplizumab Effect in Individuals at Risk for T1D 3 Months after Treatment As shown in FIGS. 22-25, in at-risk (Stage 2) relatives of T1D patients, a single course of teplizumab (as described in Example 1) increased C-peptide AUC/glucose AUC ratio for at least 6 months. At 3 months post-dosing, increase in teplizumab arm (1.5±2.9) vs. decrease in placebo (0.78±2.7; p=0.001). This difference was sustained 6 months post-treatment (p=0.004). Thus, this ratio can be used as a new early endpoint (e.g., at 3 months) for future studies of teplizumab (monotherapy re-treatment, combinations).

Teplizumab also decreased the Diabetes Prevention Trial Risk Score (DPTRS) (see Sosenko et al., Diabetes Care. 2012 July; 35(7): 1552-1555, incorporated herein by reference). This is consistent with benefit on C-peptide and glycemia: +0.56 on placebo and −0.22 in teplizumab (p=0.02). The DPTRS can also be used to help guide re-dosing in at risk individuals.

Example 4: Clinical Pharmacokinetics and Pharmacodynamics

Mechanism of Action: Teplizumab is a humanized monoclonal antibody that targets the cluster of differentiation 3 (CD3) antigen, which is co-expressed with the T-cell receptor (TCR) on the surface of T lymphocytes. Though the mechanism of action of teplizumab for the proposed indication has not been confirmed, it appears to involve weak agonistic activity on signaling via the TCR-CD3 complex, which is thought to expand regulatory T-cells and re-establish immune tolerance.

Pharmacokinetics: FIG. 26 shows plots of predicted mean teplizumab concentrations over time using a 14-day intravenous (IV) dosing regimen with a 4-day ramp-up followed by repeated doses of 826 μg/m2 on Days 5 to 14. The left panel represents a typical 60 kg male subject and the right panel represents a typical 40 kg and 90 kg male subject. Body surface area (BSA)-based dosing normalizes the exposure across body size.

The repeated IV infusions resulted in increasing serum teplizumab levels, although steady-state PK was not achieved at the end of dosing (Day 14 with this dosing regimen). The average accumulation ratio for area under the curve (AUC) between Day 5 and Day 14 was 3.4. The predicted mean (±SD) total AUC for the 14-day dosing regimen was 6421±1940 ng·day/mL with Cmax and Cmin of 826±391 and 418±225 ng/mL, respectively, on Day 14.

Distribution: The central and peripheral volume of distribution from population PK analysis was 3.4 L and 6.9 L, respectively.

Elimination: Teplizumab clearance is not dose-proportional, likely driven by its saturable binding to CD3 receptors on the T-cell surface. Teplizumab is expected to be degraded into smaller peptide fragments by catabolic pathways. The clearance of teplizumab following the 14-day dosing regimen was estimated from population PK analysis to be 2.3 L/day, with a terminal half-life of approximately 4 days.

The planned commercial drug product is manufactured in a different facility from the clinical trial product and was not used in the clinical studies submitted to support efficacy and safety. A single-dose PK bridging study was conducted in healthy volunteers that evaluated the biocomparability of the commercial drug product with the clinical trial drug product. The mean AUC0-inf for the commercial product was less than half (48.5%, 90% CI: 43.6 to 54.1) of the AUC0-inf for the product used in the primary efficacy study. The reason for this difference seems to be faster clearance of the drug from circulation rather than differences in the strength of the product, as similar concentrations were observed immediately following IV infusion (Cmax of the commercial product was 94.5% (90% CI: 84.5 to 106) of that observed in the clinical trial drug product).

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference.

REFERENCES

1. A. G. Ziegler, M. Rewers, O. Simell, T. Simell, J. Lempainen, A. Steck, C. Winkler, J. Ilonen, R. Veijola, M. Knip, Seroconversion to multiple islet autoantibodies and risk of progression to diabetes in children. *Jama* 309, 2473-2479 (2013).
2. R. A. Insel, J. L. Dunne, M. A. Atkinson, J. L. Chiang, D. Dabelea, P. A. Gottlieb, C. J. Greenbaum, K. C. Herold, J. P. Krischer, A. Lernmark, R. E. Ratner, M. J. Rewers, D. A. Schatz, J. S. Skyler, J. M. Sosenko, A. G. Ziegler, Staging presymptomatic type 1 diabetes: a scientific statement of JDRF, the Endocrine Society, and the American Diabetes Association. *Diabetes Care* 38, 1964-1974 (2015).
3. J. P. Krischer, K. F. Lynch, A. Lernmark, W. A. Hagopian, M. J. Rewers, J. X. She, J. Toppari, A. G. Ziegler, B. Akolkar, T. S. Group, Genetic and Environmental Interactions Modify the Risk of Diabetes-Related Autoimmunity by 6 Years of Age: The TEDDY Study. *Diabetes Care* 40, 1194-1202 (2017).
4. J. L. Mahon, J. M. Sosenko, L. Rafkin-Mervis, H. Krause-Steinrauf, J. M. Lachin, C. Thompson, P. J. Bingley, E. Bonifacio, J. P. Palmer, G. S. Eisenbarth, J. Wolfsdorf, J. S. Skyler, C. TrialNet Natural History, G. Type 1 Diabetes TrialNet Study, The TrialNet Natural History Study of the Development of Type 1 Diabetes: objectives, design, and initial results. *Pediatr Diabetes* 10, 97-104 (2009).
5. H. T. Siljander, R. Hermann, A. Hekkala, J. Lande, L. Tanner, P. Keskinen, J. Ilonen, O. Simell, R. Veijola, M. Knip, Insulin secretion and sensitivity in the prediction of type 1 diabetes in children with advanced beta-cell autoimmunity. *Eur J Endocrinol* 169, 479-503 (2013).
6. N. C. Foster, R. W. Beck, K. M. Miller, M. A. Clements, M. R. Rickels, L. A. DiMeglio, D. M. Maahs, W. V. Tamborlane, R. Bergenstal, E. Smith, B. A. Olson, S. K. Garg, State of Type 1 Diabetes Management and Outcomes from the T1D Exchange in 2016-2018. *Diabetes Technol Ther* 21, 66-72 (2019).
7. A. Rawshani, N. Sattar, S. Franzen, A. Rawshani, A. T. Hattersley, A. M. Svensson, B. Eliasson, S. Gudbjornsdottir, Excess mortality and cardiovascular disease in young adults with type 1 diabetes in relation to age at onset: a nationwide, register-based cohort study. *Lancet* 392, 477-486 (2018).
8. S. J. Livingstone, D. Levin, H. C. Looker, R. S. Lindsay, S. H. Wild, N. Joss, G. Leese, P. Leslie, R. J. McCrimmon, W. Metcalfe, J. A. McKnight, A. D. Morris, D. W. Pearson, J. R. Petrie, S. Philip, N. A. Sattar, J. P. Traynor, H. M. Colhoun, g. Scottish Diabetes Research Network epidemiology, R. Scottish Renal, Estimated life expectancy in a Scottish cohort with type 1 diabetes, 2008-2010. *JAMA* 313, 37-44 (2015).
9. B. Tao, M. Pietropaolo, M. Atkinson, D. Schatz, D. Taylor, Estimating the cost of type 1 diabetes in the U.S.: a propensity score matching method. *PLoS One* 5, e11501 (2010).
10. C. Evans-Molina, E. K. Sims, L. A. DiMeglio, H. M. Ismail, A. K. Steck, J. P. Palmer, J. P. Krischer, S. Geyer, P. Xu, J. M. Sosenko, G. Type 1 Diabetes TrialNet Study, beta Cell dysfunction exists more than 5 years before type 1 diabetes diagnosis. *JCI Insight* 3, (2018).
11. E. K. Sims, L. A. DiMeglio, Cause or effect? A review of clinical data demonstrating beta cell dysfunction prior to the clinical onset of type 1 diabetes. *Mol Metab* 27S, S129-S138 (2019).
12. M. K. Koskinen, O. Helminen, J. Matomaki, S. Aspholm, J. Mykkanen, M. Makinen, V. Simell, M. Vähä-Mäkilä, T. Simell, J. Ilonen, Reduced β-cell function in early preclinical type 1 diabetes. *European Journal of Endocrinology* 174, 251-259 (2016).
13. P. J. Bingley, D. K. Wherrett, A. Shultz, L. E. Rafkin, M. A. Atkinson, C. J. Greenbaum, Type 1 Diabetes TrialNet: A Multifaceted Approach to Bringing Disease-Modifying Therapy to Clinical Use in Type 1 Diabetes. *Diabetes Care* 41, 653-661 (2018).
14. C. J. Greenbaum, C. Speake, J. Krischer, J. Buckner, P. A. Gottlieb, D. A. Schatz, K. C. Herold, M. A. Atkinson, Strength in Numbers: Opportunities for Enhancing the Development of Effective Treatments for Type 1 Diabetes—The TrialNet Experience. *Diabetes* 67, 1216-1225 (2018).
15. B. M. Nathan, D. Boulware, S. Geyer, M. A. Atkinson, P. Colman, R. Goland, W. Russell, J. M. Wentworth, D. M. Wilson, C. Evans-Molina, D. Wherrett, J. S. Skyler, A. Moran, J. M. Sosenko, T. Type 1 Diabetes, G. Diabetes Prevention Trial-Type 1 Study, Dysglycemia and Index60 as Prediagnostic End Points for Type 1 Diabetes Prevention Trials. *Diabetes Care* 40, 1494-1499 (2017).
16. J. M. Sosenko, J. P. Palmer, L. Rafkin-Mervis, J. P. Krischer, D. Cuthbertson, J. Mahon, C. J. Greenbaum, C. C. Cowie, J. S. Skyler, G. Diabetes Prevention Trial-Type 16. 1 Study, Incident dysglycemia and progression to type 1 diabetes among participants in the Diabetes Prevention Trial-Type 1. *Diabetes Care* 32, 1603-1607 (2009).
17. J. P. Palmer, C-peptide in the natural history of type 1 diabetes. *Diabetes Metab Res Rev* 25, 325-328 (2009).
18. C. J. Greenbaum, A. M. Anderson, L. M. Dolan, E. J. Mayer-Davis, D. Dabelea, G. Imperatore, S. Marcovina, C. Pihoker, S. S. Group, Preservation of beta-cell function in autoantibody-positive youth with diabetes. *Diabetes Care* 32, 1839-1844 (2009).
19. W. Hagopian, R. J. Ferry, Jr., N. Sherry, D. Carlin, E. Bonvini, S. Johnson, K. E. Stein, S. Koenig, A. G. Daifotis, K. C. Herold, J. Ludvigsson, I. Protege Trial, Teplizumab preserves C-peptide in recent-onset type 1 diabetes: two-year results from the randomized, placebo-controlled Protege trial. *Diabetes* 62, 3901-3908 (2013).
20. K. C. Herold, S. E. Gitelman, M. R. Ehlers, P. A. Gottlieb, C. J. Greenbaum, W. Hagopian, K. D. Boyle, L. Keyes-Elstein, S. Aggarwal, D. Phippard, P. H. Sayre, J. McNamara, J. A. Bluestone, A. T. E. S. T. Ab, Teplizumab (anti-CD3 mAb) treatment preserves C-peptide responses in patients with new-onset type 1 diabetes in a randomized controlled trial: metabolic and immunologic features at baseline identify a subgroup of responders. *Diabetes* 62, 3766-3774 (2013).
21. K. C. Herold, W. Hagopian, J. A. Auger, E. Poumian-Ruiz, L. Taylor, D. Donaldson, S. E. Gitelman, D. M. Harlan, D. Xu, R. A. Zivin, J. A. Bluestone, Anti-CD3 monoclonal antibody in new-onset type 1 diabetes mellitus. *N Engl J Med* 346, 1692-1698. (2002).
22. B. Keymeulen, E. Vandemeulebroucke, A. G. Ziegler, C. Mathieu, L. Kaufman, G. Hale, F. Gorus, M. Goldman, M. Walter, S. Candon, L. Schandene, L. Crenier, C. De Block, J. M. Seigneurin, P. De Pauw, D. Pierard, I. Weets, P. Rebello, P. Bird, E. Berrie, M. Frewin, H. Waldmann, J. F. Bach, D. Pipeleers, L. Chatenoud, Insulin needs after CD3-antibody therapy in new-onset type 1 diabetes. *N Engl J Med* 352, 2598-2608 (2005).
23. S. A. Long, J. Thorpe, H. A. DeBerg, V. Gersuk, J. Eddy, K. M. Harris, M. Ehlers, K. C. Herold, G. T. Nepom, P. S. Linsley, Partial exhaustion of CD8 T cells and clinical response to teplizumab in new-onset type 1 diabetes. *Sci Immunol* 1, (2016).
24. N. Sherry, W. Hagopian, J. Ludvigsson, S. M. Jain, J. Wahlen, R. J. Ferry, Jr., B. Bode, S. Aronoff, C. Holland, D. Carlin, K. L. King, R. L. Wilder, S. Pillemer, E. Bonvini, S. Johnson, K. E. Stein, S. Koenig, K. C. Herold, A. G. Daifotis, I. Protege Trial, Teplizumab for treatment of type 1 diabetes (Protege study): 1-year results from a randomised, placebo-controlled trial. *Lancet* 378, 487-497 (2011).
25. J. E. Tooley, N. Vudattu, J. Choi, C. Cotsapas, L. Devine, K. Raddassi, M. R. Ehlers, J. G. McNamara, K. M. Harris, S. Kanaparthi, D. Phippard, K. C. Herold, Changes in T-cell subsets identify responders to FcR-nonbinding anti-CD3 mAb (teplizumab) in patients with type 1 diabetes. *Eur J Immunol* 46, 230-241 (2016).
26. K. C. Herold, B. N. Bundy, S. A. Long, J. A. Bluestone, L. A. DiMeglio, M. J. Dufort, S. E. Gitelman, P. A. Gottlieb, J. P. Krischer, P. S. Linsley, J. B. Marks, W. Moore, A. Moran, H. Rodriguez, W. E. Russell, D. Schatz, J. S. Skyler, E. Tsalikian, D. K. Wherrett, A. G. Ziegler, C. J. Greenbaum, G. Type 1 Diabetes TrialNet Study, An Anti-CD3 Antibody, Teplizumab, in Relatives at Risk for Type 1 Diabetes. *N Engl J Med* 381, 603-613 (2019).
27. K. Nanto-Salonen, A. Kupila, S. Simell, H. Siljander, T. Salonsaari, A. Hekkala, S. Korhonen, R. Erkkola, J. I. Sipila, L. Haavisto, Nasal insulin to prevent type 1 diabetes in children with HLA genotypes and autoantibodies conferring increased risk of disease: a double-blind, randomised controlled trial. *The Lancet* 372, 1746-1755 (2008).
28. G. Diabetes Prevention Trial—Type 1 Diabetes Study, Effects of insulin in relatives of patients with type 1 diabetes mellitus. *N Engl J Med* 346, 1685-1691 (2002).
29. G. Writing Committee for the Type 1 Diabetes TrialNet Oral Insulin Study, J. P. Krischer, D. A. Schatz, B. Bundy, J. S. Skyler, C. J. Greenbaum, Effect of Oral Insulin on Prevention of Diabetes in Relatives of Patients With Type 1 Diabetes: A Randomized Clinical Trial. *JAMA* 318, 1891-1902 (2017).
30. H. Elding Larsson, M. Lundgren, B. Jonsdottir, D. Cuthbertson, J. Krischer, A.-I. T. S. G. Di, Safety and efficacy of autoantigen-specific therapy with 2 doses of alum-formulated glutamate decarboxylase in children with multiple islet autoantibodies and risk for type 1 diabetes: A randomized clinical trial. *Pediatr Diabetes* 19, 410-419 (2018).
31. E. A. Gale, P. J. Bingley, C. L. Emmett, T. Collier, G. European Nicotinamide Diabetes Intervention Trial, European Nicotinamide Diabetes Intervention Trial (ENDIT): a randomised controlled trial of intervention before the onset of type 1 diabetes. *Lancet* 363, 925-931 (2004).
32. D. L. Eizirik, M. L. Colli, F. Ortis, The role of inflammation in insulitis and beta-cell loss in type 1 diabetes. *Nat Rev Endocrinol* 5, 219-226 (2009).
33. E. B. Tsai, N. A. Sherry, J. P. Palmer, K. C. Herold, The rise and fall of insulin secretion in type 1 diabetes mellitus. *Diabetologia* 49, 261-270 (2006).
34. E. Ferrannini, A. Mari, V. Nofrate, J. M. Sosenko, J. S. Skyler, D. P. T. S. Group, Progression to diabetes in relatives of type 1 diabetic patients: mechanisms and mode of onset. Diabetes 59, 679-685 (2010).
35. K. C. Herold, S. Usmani-Brown, T. Ghazi, J. Lebastchi, C. A. Beam, M. D. Bellin, M. Ledizet, J. M. Sosenko, J. P. Krischer, J. P. Palmer, G. Type 1 Diabetes TrialNet Study, beta cell death and dysfunction during type 1 diabetes development in at-risk individuals. *J Clin Invest* 125, 1163-1173 (2015).
36. N. A. Sherry, E. B. Tsai, K. C. Herold, Natural history of beta-cell function in type 1 diabetes. *Diabetes* 54 Suppl 2, S32-39 (2005).
37. K. C. Herold, W. Hagopian, J. A. Auger, E. Poumian-Ruiz, L. Taylor, D. Donaldson, S. E. Gitelman, D. M. Harlan, D. Xu, R. A. Zivin, J. A. Bluestone, Anti-CD3 monoclonal antibody in new-onset type 1 diabetes mellitus. *N Engl J Med* 346, 1692-1698 (2002).
38. K. C. Herold, S. E. Gitelman, U. Masharani, W. Hagopian, B. Bisikirska, D. Donaldson, K. Rother, B. Diamond, D. M. Harlan, J. A. Bluestone, A Single Course of Anti-CD3 Monoclonal Antibody hOKT3 {gamma} 1(Ala-Ala) Results in Improvement in C-Peptide Responses and Clinical Parameters for at Least 2 Years after Onset of Type 1 Diabetes. *Diabetes* 54, 1763-1769 (2005).
39. L. M. McLane, M. S. Abdel-Hakeem, E. J. Wherry, CD8 T Cell Exhaustion During Chronic Viral Infection and Cancer. *Annu Rev Immunol* 37, 457-495 (2019).
40. J. M. Sosenko, J. P. Palmer, C. J. Greenbaum, J. Mahon, C. Cowie, J. P. Krischer, H. P. Chase, N. H. White, B. Buckingham, K. C. Herold, D. Cuthbertson, J. S. Skyler, Patterns of metabolic progression to type 1 diabetes in the Diabetes Prevention Trial-Type 1. *Diabetes Care* 29, 643-649 (2006).

41. M. M. Bogun, B. N. Bundy, R. S. Goland, C. J. Greenbaum, C-Peptide Levels in Subjects Followed Longitudinally Before and After Type 1 Diabetes Diagnosis in TrialNet. *Diabetes Care* 43, 1-8 (2020).
42. L. Chatenoud, J. Primo, J. F. Bach, CD3 antibody-induced dominant self tolerance in overtly diabetic NOD mice. *J Immunol* 158, 2947-2954 (1997).
43. M. B. Davidson, A. L. Peters, D. L. Schriger, An alternative approach to the diagnosis of diabetes with a review of the literature. Diabetes Care 18, 1065-1071 (1995).
44. E. M. Akirav, M. T. Baquero, L. W. Opare-Addo, M. Akirav, E. Galvan, J. A. Kushner, D. L. Rimm, K. C. Herold, Glucose and inflammation control islet vascular density and beta-cell function in NOD mice: control of islet vasculature and vascular endothelial growth factor by glucose. *Diabetes* 60, 876-883 (2011).
45. N. A. Sherry, J. A. Kushner, M. Glandt, T. Kitamura, A. M. Brillantes, K. C. Herold, Effects of autoimmunity and immune therapy on beta-cell turnover in type 1 diabetes. *Diabetes* 55, 3238-3245 (2006).
46. A. L. Perdigoto, P. Preston-Hurlburt, P. Clark, S. A. Long, P. S. Linsley, K. M. Harris, S. E. Gitelman, C. J. Greenbaum, P. A. Gottlieb, W. Hagopian, A. Woodwyk, J. Dziura, K. C. Herold, N. Immune Tolerance, Treatment of type 1 diabetes with teplizumab: clinical and immunological follow-up after 7 years from diagnosis. *Diabetologia* 62, 655-664 (2019).
47. K. C. Herold, S. L. Bucktrout, X. Wang, B. W. Bode, S. E. Gitelman, P. A. Gottlieb, J. Hughes, T. Joh, J. B. McGill, J. H. Pettus, S. Potluri, D. Schatz, M. Shannon, C. Udata, G. Wong, M. Levisetti, B. J. Ganguly, P. D. Garzone, R. N. W. Group, Immunomodulatory activity of humanized anti-IL-7R monoclonal antibody RN168 in subjects with type 1 diabetes. *JCI Insight* 4, (2019).
48. M. Battaglia, M. S. Anderson, J. H. Buckner, S. M. Geyer, P. A. Gottlieb, T. W. H. Kay, A. Lernmark, S. Muller, A. Pugliese, B. O. Roep, C. J. Greenbaum, M. Peakman, Understanding and preventing type 1 diabetes through the unique working model of TrialNet. *Diabetologia* 60, 2139-2147 (2017).
49. L. Yu, D. C. Boulware, C. A. Beam, J. C. Hutton, J. M. Wenzlau, C. J. Greenbaum, P. J. Bingley, J. P. Krischer, J. M. Sosenko, J. S. Skyler, G. S. Eisenbarth, J. L. Mahon, G. Type 1 Diabetes TrialNet Study, Zinc transporter-8 autoantibodies improve prediction of type 1 diabetes in relatives positive for the standard biochemical autoantibodies. *Diabetes Care* 35, 1213-1218 (2012).
50. A. American Diabetes, 2. Classification and Diagnosis of Diabetes: Standards of Medical Care in Diabetes 2019. *Diabetes Care* 42, S13-S28 (2019).
51. C. Steele, W. A. Hagopian, S. Gitelman, U. Masharani, M. Cavaghan, K. I. Rother, D. Donaldson, D. M. Harlan, J. Bluestone, K. C. Herold, Insulin Secretion in Type 1 Diabetes. *Diabetes* 53, 426-433 (2004).
52. K. S. Polonsky, J. Licinio-Paixao, B. D. Given, W. Pugh, P. Rue, J. Galloway, T. Karrison, B. Frank, Use of biosynthetic human C-peptide in the measurement of insulin secretion rates in normal volunteers and type I diabetic patients. *J Clin Invest* 77, 98-105 (1986).
53. E. Van Cauter, F. Mestrez, J. Stuns, K. S. Polonsky, Estimation of insulin secretion rates from C-peptide levels. Comparison of individual and standard kinetic parameters for C-peptide clearance. *Diabetes* 41, 368-377 (1992).
54. S. A. Long, J. Thorpe, K. C. Herold, M. Ehlers, S. Sanda, N. Lim, P. S. Linsley, G. T. Nepom, K. M. Harris, Remodeling T cell compartments during anti-CD3 immunotherapy of type 1 diabetes. *Cell Immunol* 319, 3-9 (2017).

What is claimed is:

1. A method of preventing or delaying the onset of clinical type 1 diabetes (T1D), comprising:
administering a prophylactically effective amount of teplizumab to a non-diabetic subject who is at risk for T1D, wherein the prophylactically effective amount of teplizumab comprises a 10 to 14 day course of teplizumab,
wherein at three months or more after the administration of the 10 to 14 day course of teplizumab, the subject has a frequency of from about 5% to about 50% T Cell Immunoreceptor With Ig And ITIM Domains (TIGIT)+ killer cell lectin like receptor G1 (KLRG1)+ cluster of differentiation 8 (CD8)+ T-cells in all cluster of differentiation 3 (CD3)+ T-cells, indicative of successful prevention or delay of the onset of clinical T1D.

2. The method of claim 1, wherein the non-diabetic subject is a relative of a patient with T1D.

3. The method of claim 1, wherein the non-diabetic subject (1) is negative for zinc transporter 8 (ZnT8) antibodies, (2) is HLA-DR4+, and/or (3) is not HLA-DR3+.

4. The method of claim 3, wherein the non-diabetic subject has 2 or more diabetes-related autoantibodies selected from islet cell antibodies (ICA), insulin autoantibodies (IAA), and antibodies to glutamic acid decarboxylase (GAD), tyrosine phosphatase (IA-2/ICA512) or ZnT8.

5. The method of claim 3, wherein the non-diabetic subject does not have antibodies against ZnT8.

6. The method of claim 3, wherein the non-diabetic subject is HLA-DR4+ and is not HLA-DR3+.

7. The method of claim 1, wherein the non-diabetic subject has abnormal glucose tolerance on oral glucose tolerance test (OGTT).

8. The method of claim 7, wherein the abnormal glucose tolerance on OGTT is a fasting glucose level of 110-125 mg/dL, a 2 hour plasma glucose level of $\geq$140 and <200 mg/dL, or an intervening glucose level of >200 mg/dL at 30, 60, or 90 minutes on OGTT.

9. The method of claim 1, comprising administering by subcutaneous injection the 10 to 14 day course of teplizumab at a daily dose of 10-1000 micrograms/meter squared ($\mu$g/m$^2$).

10. The method of claim 1, wherein the administering of the prophylactically effective amount of teplizumab delays median time to clinical diagnosis of T1D by at least 50%, at least 80%, or by at least 90%, or at least 12 months, at least 18 months, at least 24 months, at least 36 months, at least 48 months, or at least 60 months.

11. The method of claim 1, comprising determining the frequency of TIGIT+KLRG1+CD8+ T-cells by flow cytometry.

12. The method of claim 1, comprising determining a decrease in a percentage of CD8+ T-cells expressing proliferation markers Ki67 and/or CD57.

13. The method of claim 1, comprising administering by intravenous infusion the 10 to 14 day course of teplizumab at a daily dose of 10-1000 micrograms/meter squared ($\mu$g/m$^2$).

14. The method of claim 1 comprising administering orally the 10 to 14 day course of teplizumab at a daily dose of 10-1000 micrograms/meter squared ($\mu$g/m$^2$).

15. The method of claim 1, comprising administering a daily dose of from about 5 to about 1200 $\mu$g/m$^2$ of teplizumab over a 14 day course.

16. The method of claim 1, comprising administering a 14 day course of teplizumab by IV infusion at about 51 $\mu$g/m$^2$ on day 0, about 103 µg/m² on day 1, about 207 µg/m² on day 2, and about 413 µg/m² on day 3, and one dose of about 826 µg/m² on each of days 4 to 13.

17. The method of claim 1, comprising determining the frequency of TIGIT+KLRG1+CD8+ T-cells in all the CD3+ T-cells in the non-diabetic subject prior to the administering step.

18. The method of claim 1, comprising determining the frequency of TIGIT+KLRG1+CD8+ T-cells in all the CD3+ T-cells in the non-diabetic subject after the administering step.

19. The method of claim 1, comprising determining, prior to or after said administering, the frequency of CD8+ T-cells that express CD127.

20. The method of claim 1, wherein the frequency of TIGIT+KLRG1+CD8+Ki67+ T-cells is decreased by from 30% to 70%.

21. A method of delaying the onset of clinical type 1 diabetes (T1D), comprising:
   administering a prophylactically effective amount of teplizumab to a non-diabetic subject at risk for T1D, wherein the prophylactically effective amount of teplizumab comprises a 10 to 14 day course of teplizumab, wherein at three months or more after the administration of the 10 to 14 day course of teplizumab, the subject has a frequency of about 5% to about 50% TIGIT+KLRG1+CD8+ T-cells in all CD3+ T-cells, indicative of successful delay of the onset of clinical T1D.

22. The method of claim 21, comprising administering a first 10 to 14 day course of teplizumab and administering a second 10 to 14 day course of teplizumab,
   wherein the administering of the second 10 to 14 day course of teplizumab is from 2 months to 36 months after the administering of the first course of teplizumab, and
   wherein the administering of the second 10 to 14 day course of teplizumab increases the generation or maintenance of the TIGIT+KLRG1+CD8+ T-cells.

23. A method of delaying the onset of clinical type 1 diabetes (T1D), comprising:
   administering a prophylactically effective amount of teplizumab to a non-diabetic subject at risk for T1D, wherein the prophylactically effective amount comprises a 10 to 14 day course of teplizumab; and
   measuring a frequency of TIGIT+KLRG1+CD8+ T-cells in all CD3+ T-cells in the non-diabetic subject at three months or more after the administration of the 10 to 14 day course of teplizumab,
   wherein a measured frequency of about 5% to about 50% TIGIT+KLRG1+CD8+ T-cells in all CD3+ T-cells in the non-diabetic subject at three months or more after the administering of the 10 to 14 day course of teplizumab is indicative of successful delay of the onset of clinical T1D.

* * * * *

UNITED STATES PATENT AND TRADEMARK OFFICE
CERTIFICATE OF CORRECTION

| | | |
|---|---|---|
| PATENT NO. | : 12,006,366 B2 | Page 1 of 1 |
| APPLICATION NO. | : 17/345495 | |
| DATED | : June 11, 2024 | |
| INVENTOR(S) | : Francisco Leon et al. | |

It is certified that error appears in the above-identified patent and that said Letters Patent is hereby corrected as shown below:

In the Claims

Column 42, Line 46, change "or by at least 90%, or at least 12 months" to --or at least 90%, or by at least 12 months--

Signed and Sealed this
Tenth Day of September, 2024

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 213
<212> TYPE: PRT
<213> ORGANISM: Unknown
<220> FEATURE:
<223> OTHER INFORMATION: Synthetic

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
```

```
            115                 120                 125
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 2
<211> LENGTH: 449
<212> TYPE: PRT
<213> ORGANISM: Unknown
<220> FEATURE:
<223> OTHER INFORMATION: Synthetic

<400> SEQUENCE: 2

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

-continued

```
                    260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```